US012781233B2

(12) United States Patent
Boeke et al.

(10) Patent No.: US 12,781,233 B2
(45) Date of Patent: Nov. 3, 2026

(54) **ORTHOGONAL TRANSCRIPTIONAL SWITCHES DERIVED FROM TET REPRESSOR HOMOLOGS FOR *SACCHAROMYCES CEREVISIAE***

(71) Applicant: The Johns Hopkins University, Baltimore, MD (US)

(72) Inventors: Jef D. Boeke, New York, NY (US); Shigehito Ikushima, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1703 days.

(21) Appl. No.: 16/467,890

(22) PCT Filed: Dec. 7, 2017

(86) PCT No.: PCT/US2017/065067
§ 371 (c)(1),
(2) Date: Jun. 7, 2019

(87) PCT Pub. No.: WO2018/106892
PCT Pub. Date: Jun. 14, 2018

(65) Prior Publication Data

US 2019/0338294 A1 Nov. 7, 2019

Related U.S. Application Data

(60) Provisional application No. 62/431,170, filed on Dec. 7, 2016.

(51) Int. Cl.
*C12N 15/63* (2006.01)
*C12N 15/52* (2006.01)
*C12N 15/81* (2006.01)

(52) U.S. Cl.
CPC ............ *C12N 15/81* (2013.01); *C12N 15/52* (2013.01); *C12N 15/635* (2013.01); *C12N 2800/102* (2013.01); *C12N 2800/60* (2013.01); *C12N 2810/50* (2013.01); *C12N 2830/003* (2013.01); *C12N 2830/005* (2013.01); *C12N 2830/60* (2013.01); *C12Y 101/01001* (2013.01)

(58) Field of Classification Search
None
See application file for complete search history.

(56) References Cited

FOREIGN PATENT DOCUMENTS

WO 2015/175074 A2 11/2015

OTHER PUBLICATIONS

Bellí et al., An activator/repressor dual system allows tight tetracycline-regulated gene expression in budding yeast. Nucleic Acids Research (1998), 26: 942-94 (Year: 1998).*

Mullick et al., The cumate gene-switch: a system for regulated expression in mammalian cells. BMC Biotechnology (2006), 6: 43, doi: 10.1186/1472-6750-6-43 (Year: 2006).*

Abbas et al., Characterization of Interactions between the Transcriptional Repressor PhIF and Its Binding Site at the phIA Promoter in Pseudomonas fluorescens F113. Journal of Bacteriology (2002), 184: 3008-3016 (Year: 2002).*

Garí et al., A Set of Vectors with a Tetracycline-Regulatable Promoter System for Modulated Gene Expression in *Saccharomyces cerevisiae*. Yeast (1997), 13: 837-848 (Year: 1997).*

Stanton et al. Systematic Transfer of Prokaryotic Sensors and Circuits to Mammalian Cells. ACS Synthetic Biology (2014), 3: 880-891 (Year: 2014).*

Richardson et al., GeneDesign: Rapid, automated design of multikilobase synthetic genes. 2006 Genome Res., 16: 550-556 (Year: 2006).*

AAF20928.1, PhIF [Pseudomonas protegens], https://www.ncbi.nlm.nih.gov/protein/AAF20928.1, available Nov. 9, 2005, [retrieved Nov. 4, 2024] (Year: 2005).*

BAM 10891.1, Fusion protein of reverse tetracycline repressor protein and immediate early protein 1 activation domain, available Apr. 11, 2012, https://www.ncbi.nlm.nih.gov/protein/BAM10891.1, [retrieved Nov. 4, 2024] (Year: 2012).*

Sharp et al., Synonymous codon usage in *Saccharomyces cerevisiae*. Yeast (1991), 7: 657-678 (Year: 1991).*

Wada et al., Misdecoding of rare CGA codon by translation termination factors, eRF1/eRF3, suggests novel class of ribosome rescue pathway in *S. cerevisiae*. FEBS Journal (2019), 286: 788-802 (Year: 2019).*

Stanton et al. Systematic Transfer of Prokaryotic Sensors and Circuits to Mammalian Cells. ACS Synthetic Biology (2014), 3: 880-891, and Supplemental material (Year: 2014).*

Michaelis et al., Cohesins: chromosomal proteins that prevent premature separation of sister chromatids. Cell (1997), 91: 35-45 (Year: 1997).*

Plasmid #40942, pAT222 https://www.addgene.org/40942/, first available in 2011, [retrieved Jan. 6, 2026] (Year: 2011).*

AF207529.2, Pseudomonas fluorescence PhIA (phIA), PhIF (phIF), PhIG, (phIG, and PhIH (phIH) genes, complete cds, https://www.ncbi.nlm.nih.gov/nuccore/AF207529.2, [retrieved Jan. 2, 2026] (Year: 2005).*

Lanza et al., A condition-specific codon optimization approach for improved heterologous gene expression in *Saccharomyces cerevisiae*. BMC Systems Biology (2014), 8: 33, pp. 1-10 and Supplemental Material (Year: 2014).*

Elena et al., Expression of codon optimized genes in microbial systems: current industrial applications and perspectives. Frontiers in Microbiology (2014), 5(21): 1-8 (Year: 2014).*

Stanton, et al. "Systematic transfer of prokaryotic sensors and ciucuits to mammalian cells," ACS Synth Biol. Nov. 20, 2014 (Nov. 20, 2014), vol. 3, pp. 880-891, entire document.

(Continued)

*Primary Examiner* — Catherine Konopka
(74) *Attorney, Agent, or Firm* — Fox Rothschild LLP

(57) ABSTRACT

The invention features compositions and methods for identifying orthogonal transcriptional switches derived from Tet repressor homologs for *Saccharomyces cerevishiae* regulated by 2,4-diacetylphloroglucinol (DAPG) and other ligands.

14 Claims, 7 Drawing Sheets

Specification includes a Sequence Listing.

(56) References Cited

OTHER PUBLICATIONS

Kushima et al. "New Orthogonal Transcriptional Switches Derived from Tet Repressor Homologues for *Saccharomyces cerevisiae* Regulated by 2,4-Diacetylphloroglucinol and Other Ligands," ACS Synth Biol. Dec. 22, 2016 (Dec. 22, 2016), vol. 6, pp. 497-506, entire document.
Abbas et al. "Characterization of interactions between the transcriptional repressor PhIF and its binding site at the PhIA promoter in Pseudomonas Fluorescens F113," J Bacteriol. Jun. 16, 2002 (Jun. 16, 2002), vol. 184, pp. 3008-3016, entire document.
Schnider-Keel, et al. "Autoinduction of 2,4-diacetylphlorogluucinol biosynthesis in the biocontrol agent Pseudomonas fluorescens CHA0 and repression by the bacterial metabolites salicylate and pyoluteorin" J Bacteriol, Mar. 1, 2000 (Mar. 1, 2000), vol. 182, p. 1215-12225, entire document.
International Search Report dated Mar. 20, 2018—PCT/US2017/065067.

* cited by examiner

SEQUENCE LISTING

<160> NUMBER OF SEQ ID NOS: 36

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1
tccacaatca attgcgagaa gc 22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 2
catttgttgg aggaaagttg tcc 23

<210> SEQ ID NO 3
<211> LENGTH: 40
<212> TYPE: DNA
<213> ORGANISM: Pseudomonas sp.

<400> SEQUENCE: 3
tatgtatgat acgaaacgta ccgtatcgtt aaggtagcgt 40

<210> SEQ ID NO 4
<211> LENGTH: 47
<212> TYPE: DNA
<213> ORGANISM: Streptomyces virginiae

<400> SEQUENCE: 4
tgtcacttgt acatcgtata actctcatat acgttgtaga acagttc 47

<210> SEQ ID NO 5
<211> LENGTH: 79
<212> TYPE: DNA
<213> ORGANISM: Bacillus subtilis

<400> SEQUENCE: 5
ctttctccta caattatata gaacggtcta gacaaatgaa tgataatata tagactggtc 60
taaattggag gaagcgata 79

<210> SEQ ID NO 6
<211> LENGTH: 28
<212> TYPE: DNA
<213> ORGANISM: Staphylococcus epidermidis

<400> SEQUENCE: 6
acaacctaac taacgaaagg taggtgaa 28

<210> SEQ ID NO 7
<211> LENGTH: 55
<212> TYPE: DNA
<213> ORGANISM: Mycobacterium tuberculosis

<400> SEQUENCE: 7
gtgtcgatag tgtcgacatc tcgttgacgg cctcgacatt acgttgatag cgtgg 55

<210> SEQ ID NO 8
<211> LENGTH: 35
<212> TYPE: DNA
<213> ORGANISM: Pseudomonas putida

<400> SEQUENCE: 8
aagaaagaaa caaaccaacc tgtctgtatt atctc 35

<210> SEQ ID NO 9
<211> LENGTH: 729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
atggctagaa ccccatctcg atcttctatc ggttctttgc gatctccaca cacccacaag 60
gctatcttga cctctaccat cgaaatcttg aaggaatgtg gttactctgg tttgtctatc 120
gaatctgttg ctagaagagc tggtgcttct aagccaacca tctacagatg gtggaccaac 180
aaggctgctt tgatcgctga agtttacgaa aacgaatctg aacaagttag aaagttccca 240
gacttgggtt ctttcaaggc tgacttggac ttcttgttga gaaacttgtg gaaggtttgg 300
agagaaacca tctgtggtga ggctttcaga tgtgttatcg ctgaagctca attggaccca 360
gctaccttga cccaattgaa ggaccaattc atggaaagaa gaagagaaat gccaaagaag 420
ttggttgaaa acgctatctc taacggtgaa ttgccaaagg acaccaacag agaattgttg 480
ttggacatga tcttcggttt ctgttggtac agattgttga ccgaacaatt gaccgttgaa 540
caagacatcg aagagttcac cttcttgttg atcaacggtg tttgtccagg aacccaaaga 600
gggccggccg acgctttgga cgacttcgac ttggacatgt tgcctgcaga tgcacttgat 660
gattttgatc ttgatatgct tccagcagac gcattggatg actttgacct tgacatgctt 720
cctggttga 729

<210> SEQ ID NO 10
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Met Ala Arg Thr Pro Ser Arg Ser Ser Ile Gly Ser Leu Arg Ser Pro
1 5 10 15

His Thr His Lys Ala Ile Leu Thr Ser Thr Ile Glu Ile Leu Lys Glu
20 25 30

Cys Gly Tyr Ser Gly Leu Ser Ile Glu Ser Val Ala Arg Arg Ala Gly
35 40 45

Ala Ser Lys Pro Thr Ile Tyr Arg Trp Trp Thr Asn Lys Ala Ala Leu
50 55 60

Ile Ala Glu Val Tyr Glu Asn Glu Ser Glu Gln Val Arg Lys Phe Pro
65 70 75 80

Asp Leu Gly Ser Phe Lys Ala Asp Leu Asp Phe Leu Leu Arg Asn Leu
85 90 95

Trp Lys Val Trp Arg Glu Thr Ile Cys Gly Glu Ala Phe Arg Cys Val
100 105 110

Ile Ala Glu Ala Gln Leu Asp Pro Ala Thr Leu Thr Gln Leu Lys Asp
115 120 125

Gln Phe Met Glu Arg Arg Arg Glu Met Pro Lys Lys Leu Val Glu Asn
130 135 140

Ala Ile Ser Asn Gly Glu Leu Pro Lys Asp Thr Asn Arg Glu Leu Leu
145 150 155 160

Leu Asp Met Ile Phe Gly Phe Cys Trp Tyr Arg Leu Leu Thr Glu Gln
165 170 175

Leu Thr Val Glu Gln Asp Ile Glu Glu Phe Thr Phe Leu Leu Ile Asn
180 185 190

Gly Val Cys Pro Gly Thr Gln Arg Gly Pro Ala Asp Ala Leu Asp Asp
195 200 205

Phe Asp Leu Asp Met Leu Pro Ala Asp Ala Leu Asp Asp Phe Asp Leu
210 215 220

Asp Met Leu Pro Ala Asp Ala Leu Asp Asp Phe Asp Leu Asp Met Leu
225 230 235 240

Pro Gly

<210> SEQ ID NO 11
<211> LENGTH: 624
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
atgccaaaga agaagagaaa ggttgctaga accccatctc gatcttctat cggttctttg 60
cgatctccac acacccacaa ggctatcttg acctctacca tcgaaatctt gaaggaatgt 120
ggttactctg gtttgtctat cgaatctgtt gctagaagag ctggtgcttc taagccaacc 180
atctacagat ggtggaccaa caaggctgct ttgatcgctg aagtttacga aaacgaatct 240
gaacaagtta gaaagttccc agacttgggt tctttcaagg ctgacttgga cttcttgttg 300
agaaacttgt ggaaggtttg gagagaaacc atctgtggtg aggctttcag atgtgttatc 360
gctgaagctc aattggaccc agctaccttg acccaattga aggaccaatt catggaaaga 420
agaagagaaa tgccaaagaa gttggttgaa aacgctatct ctaacggtga attgccaaag 480
gacaccaaca gagaattgtt gttggacatg atcttcggtt tctgttggta cagattgttg 540
accgaacaat tgaccgttga acaagacatc gaagagttca ccttcttgtt gatcaacggt 600
gtttgtccag gaacccaaag atga 624

<210> SEQ ID NO 12
<211> LENGTH: 207
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 12

Met Pro Lys Lys Lys Arg Lys Val Ala Arg Thr Pro Ser Arg Ser Ser
1 5 10 15

Ile Gly Ser Leu Arg Ser Pro His Thr His Lys Ala Ile Leu Thr Ser
20 25 30

Thr Ile Glu Ile Leu Lys Glu Cys Gly Tyr Ser Gly Leu Ser Ile Glu
35 40 45

```
Ser Val Ala Arg Arg Ala Gly Ala Ser Lys Pro Thr Ile Tyr Arg Trp
    50                  55                  60

Trp Thr Asn Lys Ala Ala Leu Ile Ala Glu Val Tyr Glu Asn Glu Ser
65                  70                  75                  80

Glu Gln Val Arg Lys Phe Pro Asp Leu Gly Ser Phe Lys Ala Asp Leu
                85                  90                  95

Asp Phe Leu Leu Arg Asn Leu Trp Lys Val Trp Arg Glu Thr Ile Cys
            100                 105                 110

Gly Glu Ala Phe Arg Cys Val Ile Ala Glu Ala Gln Leu Asp Pro Ala
        115                 120                 125

Thr Leu Thr Gln Leu Lys Asp Gln Phe Met Glu Arg Arg Arg Glu Met
    130                 135                 140

Pro Lys Lys Leu Val Glu Asn Ala Ile Ser Asn Gly Glu Leu Pro Lys
145                 150                 155                 160

Asp Thr Asn Arg Glu Leu Leu Leu Asp Met Ile Phe Gly Phe Cys Trp
                165                 170                 175

Tyr Arg Leu Leu Thr Glu Gln Leu Thr Val Glu Gln Asp Ile Glu Glu
            180                 185                 190

Phe Thr Phe Leu Leu Ile Asn Gly Val Cys Pro Gly Thr Gln Arg
        195                 200                 205
```

<210> SEQ ID NO 13
<211> LENGTH: 653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
cacttctaaa taagcgaatt tcttatgatt tatgattttt attattaaat aagttataaa     60

aaaaataagt gtatacaaat tttaaagtga ctcttaggtt ttaaaacgaa aattcttgtt    120

cttgagtaac tctttcctgt aggtcaggtt gctttctcag gtatagcatg aggtcgctct    180

tattgaccac acctctaccg gcaggccggc ccggtatgta tgatacgaaa cgtaccgtat    240

cgttaaggta gcgttatgta tgatacgaaa cgtaccgtat cgttaaggta gcgttatgta    300

tgatacgaaa cgtaccgtat cgttaaggta gcgttatgta tgatacgaaa cgtaccgtat    360

cgttaaggta gcgttatgta tgatacgaaa cgtaccgtat cgttaaggta gcgttatgta    420

tgatacgaaa cgtaccgtat cgttaaggta gcgttatgta tgatacgaaa cgtaccgtat    480

cgttaaggta gcgtcccggg ccggcctatg gcatgcatgt gctctgtatg tatataaaac    540

tcttgttttc ttcttttctc taaatattct ttccttatac attaggtcct ttgtagcata    600

aattactata cttctataga cacgcaaaca caaatacaca cactaaatta ata           653
```

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14

```
atgatacgaa acgtaccgta tcgttaaggt                                      30
```

<210> SEQ ID NO 15

<211> LENGTH: 823
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
taaagtccaa tgctagtaga gaagggggt aacacccctc cgcgctcttt tccgattttt 60
ttctaaaccg tggaatattt cggatatcct tttgttgttt ccgggtgtac aatatggact 120
tcctcttttc tggcaaccaa acccatacat cgggattcct ataatacctt cgttggtcac 180
cctaacatgt aggtggcgga ggggagatat acaatagaac agataccaga caagacataa 240
tgggctaaac aagactacac caattacact gcctcattga tggtggtaca taacgaacta 300
atactgtagc cctagacttg atagccatca tcatatcgaa gtttcactac ccttttttcca 360 tttgccatct attgaagtaa taataggcgc atgcaacttc ttttcttttt ttttcttttc 420
tctctccccc gttgttgtct caccatatcc gcaatgacaa aaaaatgatg gaagacacta 480
aaggaaaaaa ttaacgacaa agacagcacc aacagatgtc gttgttccag agctgatgag 540
gggtatctcg aagcacacga aactttttcc ttccttcatt cacgcacact actctctaat 600
gagcaacggt atacggcctt ccttccagtt acttgaattt gaaataaaaa aaagtttgct 660
gtcttgctat caagtataaa tagacctgca attatgtatg atacgaaacg taccgtatcg 720
ttaaggtagc gtatgatacg aaacgtaccg tatcgttaag gtagcgtctt tcttccttgt 780
ttctttttct gcaggtcgac tctagaggat ccccgggtat taa 823

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
atgatacgaa acgtaccgta tcgttaaggt agcgt 35

<210> SEQ ID NO 17
<211> LENGTH: 762
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
atgccaaaga agaagagaaa ggtaatgtct ccaaagagaa gaactcaagc tgaaagagct 60
atggaaactc aaggtaagtt gatcgctgct gctttgggtg ttttgagaga aaagggttac 120
gctggtttca gaatcgctga cgttccaggt gctgctggtg tttctagagg tgctcaatct 180
caccacttcc caaccaagtt ggaattgttg ttggctacct tcgaatggtt gtacgaacaa 240
atcaccgaaa gatctagagc tagattggct aagttgaagc cagaagacga cgttatccaa 300
caaatgttgg acgacgctgc tgaattcttc ttggacgacg acttctctat ctctttggac 360
ttgatcgttg ctgctgaccg cgatcctgct ttgagagaag gtatccaaag aaccgttgaa 420
agaaacagat tcgttgttga agacatgtgg ttgggtgttt tggtttctag aggtttgtct 480
cgcgacgacg ctgaagacat cttgtggttg atcttcaact ctgttagagg tttggctgtt 540
agatctttgt ggcaaaagga caaggaaaga ttcgaaagag ttagaaactc taccttggaa 600
atcgctagag aaagatacgc taagttcaag agggggccgg ccgacgcttt ggacgacttc 660
gacttggaca tgttgcctgc agatgcactt gatgattttg atcttgatat gcttccagca 720
gacgcattgg atgactttga ccttgacatg cttcctggtt ga 762

<210> SEQ ID NO 18
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Met Pro Lys Lys Lys Arg Lys Val Met Ser Pro Lys Arg Arg Thr Gln
1 5 10 15

Ala Glu Arg Ala Met Glu Thr Gln Gly Lys Leu Ile Ala Ala Ala Leu
20 25 30

Gly Val Leu Arg Glu Lys Gly Tyr Ala Gly Phe Arg Ile Ala Asp Val
35 40 45

Pro Gly Ala Ala Gly Val Ser Arg Gly Ala Gln Ser His His Phe Pro
50 55 60

Thr Lys Leu Glu Leu Leu Leu Ala Thr Phe Glu Trp Leu Tyr Glu Gln
65 70 75 80

Ile Thr Glu Arg Ser Arg Ala Arg Leu Ala Lys Leu Lys Pro Glu Asp
85 90 95

Asp Val Ile Gln Gln Met Leu Asp Asp Ala Ala Glu Phe Phe Leu Asp
100 105 110

Asp Asp Phe Ser Ile Ser Leu Asp Leu Ile Val Ala Ala Asp Arg Asp
115 120 125

Pro Ala Leu Arg Glu Gly Ile Gln Arg Thr Val Glu Arg Asn Arg Phe
130 135 140

Val Val Glu Asp Met Trp Leu Gly Val Leu Val Ser Arg Gly Leu Ser
145 150 155 160

Arg Asp Asp Ala Glu Asp Ile Leu Trp Leu Ile Phe Asn Ser Val Arg
165 170 175

Gly Leu Ala Val Arg Ser Leu Trp Gln Lys Asp Lys Glu Arg Phe Glu
180 185 190

Arg Val Arg Asn Ser Thr Leu Glu Ile Ala Arg Glu Arg Tyr Ala Lys
195 200 205

Phe Lys Arg Gly Pro Ala Asp Ala Leu Asp Asp Phe Asp Leu Asp Met
210 215 220

Leu Pro Ala Asp Ala Leu Asp Asp Phe Asp Leu Asp Met Leu Pro Ala
225 230 235 240

Asp Ala Leu Asp Asp Phe Asp Leu Asp Met Leu Pro Gly
245 250

<210> SEQ ID NO 19
<211> LENGTH: 564
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
cacttctaaa taagcgaatt tcttatgatt tatgattttt attattaaat aagttataaa 60
aaaaataagt gtatacaaat tttaaagtga ctcttaggtt ttaaaacgaa aattcttgtt 120
cttgagtaac tctttcctgt aggtcaggtt gctttctcag gtatagcatg aggtcgctct 180
tattgaccac acctctaccg gcaaggtaag aaagaaacaa accaacctgt ctgtattatc 240
tcaagaaaga aacaaaccaa cctgtctgta ttatctcaag aaagaaacaa accaacctgt 300
ctgtattatc tcaagaaaga aacaaaccaa cctgtctgta ttatctcaag aaagaaacaa 360
accaacctgt ctgtattatc tcaagaaaga aacaaaccaa cctgtctgta ttatctcaat 420
ggcatgcatg tgctctgtat gtatataaaa ctcttgtttt cttcttttct ctaaatattc 480
tttccttata cattaggtcc tttgtagcat aaattactat acttctatag acacgcaaac 540
acaaatacac acactaaatt aata 564

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
agaaacaaac caacctgtct gtatta 26

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
aacaaacaga caatctggtc tgtttgta 28

<210> SEQ ID NO 22
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22
atgagtagat tggacaagtc taaggttatc aactctgctt tggaattgtt gaacgaagtt 60
ggtatcgaag gtttgaccac cagaaagttg gctcaaaagt tgggtgttga acaaccaacc 120
ttgtactggc acgttaagaa caagagagct ttgttggacg ctttggctat cgaaatgttg 180
gacagacacc acacccactt ctgtccattg gaaggtgaat cttggcaaga cttcttgaga 240
aacaacgcta agtctttcag atgtgctttg ctctctcacc gcgacggtgc taaggttcac 300
ttgggaacca gaccaaccga aaagcaatac gaaaccttgg aaaaccaatt ggctttcttg 360
tgtcaacaag gtttctcttt ggaaaacgct ttgtacgctt tgtctgctgt tggtcacttc 420
accttgggtt gtgttttgga agaccaagaa caccaagttg ctaaggaaga aagagaaacc 480
ccaaccaccg actctatgcc accattgctc agacaagcta tcgaattgtt cgaccaccaa 540
ggtgctgaac cagctttctt gttcggtttg gaattgatca tctgtggttt ggaaaagcaa 600
ttgaagtgtg aatctggtgg gccggccgac gctttggacg acttcgactt ggacatgttg 660
ccagctgacg ctttggacga cttcgacttg gacatgttgc cagctgacgc tttggacgac 720
ttcgacttgg acatgttgcc aggttga 747

<210> SEQ ID NO 23
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Met Ser Arg Leu Asp Lys Ser Lys Val Ile Asn Ser Ala Leu Glu Leu
1 5 10 15

Leu Asn Glu Val Gly Ile Glu Gly Leu Thr Thr Arg Lys Leu Ala Gln
20 25 30

Lys Leu Gly Val Glu Gln Pro Thr Leu Tyr Trp His Val Lys Asn Lys
35 40 45

Arg Ala Leu Leu Asp Ala Leu Ala Ile Glu Met Leu Asp Arg His His
50 55 60

Thr His Phe Cys Pro Leu Glu Gly Glu Ser Trp Gln Asp Phe Leu Arg
65 70 75 80

Asn Asn Ala Lys Ser Phe Arg Cys Ala Leu Leu Ser His Arg Asp Gly
85 90 95

Ala Lys Val His Leu Gly Thr Arg Pro Thr Glu Lys Gln Tyr Glu Thr
100 105 110

Leu Glu Asn Gln Leu Ala Phe Leu Cys Gln Gln Gly Phe Ser Leu Glu
115 120 125

Asn Ala Leu Tyr Ala Leu Ser Ala Val Gly His Phe Thr Leu Gly Cys
130 135 140

Val Leu Glu Asp Gln Glu His Gln Val Ala Lys Glu Glu Arg Glu Thr
145 150 155 160

Pro Thr Thr Asp Ser Met Pro Pro Leu Leu Arg Gln Ala Ile Glu Leu
165 170 175

Phe Asp His Gln Gly Ala Glu Pro Ala Phe Leu Phe Gly Leu Glu Leu
180 185 190

Ile Ile Cys Gly Leu Glu Lys Gln Leu Lys Cys Glu Ser Gly Gly Pro
195 200 205

Ala Asp Ala Leu Asp Asp Phe Asp Leu Asp Met Leu Pro Ala Asp Ala
210 215 220

Leu Asp Asp Phe Asp Leu Asp Met Leu Pro Ala Asp Ala Leu Asp Asp
225 230 235 240

Phe Asp Leu Asp Met Leu Pro Gly
245

<210> SEQ ID NO 24
<211> LENGTH: 667
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24
cacttctaaa taagcgaatt tcttatgatt tatgattttt attattaaat aagttataaa 60
aaaaataagt gtatacaaat tttaaagtga ctcttaggtt ttaaaacgaa aattcttgtt 120
cttgagtaac tctttcctgt aggtcaggtt gctttctcag gtatagcatg aggtcgctct 180
tattgaccac acctctaccg gcaggccggc ccgggtcgag tttaccactc cctatcagtg 240
atagagaaaa gtgaaagtcg agtttaccac tccctatcag tgatagagaa aagtgaaagt 300
cgagtttacc actccctatc agtgatagag aaaagtgaaa gtcgagttta ccactcccta 360
tcagtgatag agaaaagtga aagtcgagtt taccactccc tatcagtgat agagaaaagt 420
gaaagtcgag tttaccactc cctatcagtg atagagaaaa gtgaaagtcg agtttaccac 480
tccctatcag tgatagagaa aagtgaaacc cgggccggcc tatggcatgc atgtgctctg 540
tatgtatata aaactcttgt tttcttcttt tctctaaata ttctttcctt atacattagg 600
tcctttgtag cataaattac tatacttcta tagacacgca aacacaaata cacacactaa 660
attaata 667

<210> SEQ ID NO 25
<211> LENGTH: 711
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25
atggacatca agcaatcttt gttgcacgct gctatgagat tgttgtctgc taagggtcgc 60
gacggtgcta ccatgcgacc aatctgtgct gaagttggtg ttaccccacc aaccttgtac 120
caccactacg gtgacttgca aggtttgcac aaggctgcta tcgacgaaac ctacagacaa 180
gttgctgaag cttaccacgg tggtaccgaa gaaagaggtc cattgaaggg tatccgcgac 240
ggttgggcta ccttcttgca attcgcttac tctgaaccaa acatgtgtag aatgttggtt 300
caacacatca tggctggtga accaccatct atggttgctg acaccttgag aggtgttgct 360
gacgacttgg ctcaattcca cgctcaaggt agattgacct tcccaccaag agaagctgct 420
caattgttgt ggatgggtgc tttgggtgct ttgacctacg ctttgtctag agaaggtgct 480
ggttacaccc aagacttggc tttgcaaaag gctaagttgg acatcacctt ggttgctttg 540
ttcaacatcg aagaagaagg gccggccgac gctttggacg acttcgactt ggacatgttg 600
cctgcagatg cacttgatga ttttgatctt gatatgcttc cagcagacgc attggatgac 660
tttgaccttg acatgcttcc tggtatgcca aagaagaaga gaaaggtatg a 711

<210> SEQ ID NO 26
<211> LENGTH: 236
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

Met Asp Ile Lys Gln Ser Leu Leu His Ala Ala Met Arg Leu Leu Ser
1 5 10 15

Ala Lys Gly Arg Asp Gly Ala Thr Met Arg Pro Ile Cys Ala Glu Val
20 25 30

Gly Val Thr Pro Pro Thr Leu Tyr His His Tyr Gly Asp Leu Gln Gly
35 40 45

Leu His Lys Ala Ala Ile Asp Glu Thr Tyr Arg Gln Val Ala Glu Ala
50 55 60

Tyr His Gly Gly Thr Glu Glu Arg Gly Pro Leu Lys Gly Ile Arg Asp
65 70 75 80

```
Gly Trp Ala Thr Phe Leu Gln Phe Ala Tyr Ser Glu Pro Asn Met Cys
                85                  90                  95

Arg Met Leu Val Gln His Ile Met Ala Gly Glu Pro Pro Ser Met Val
            100                 105                 110

Ala Asp Thr Leu Arg Gly Val Ala Asp Asp Leu Ala Gln Phe His Ala
        115                 120                 125

Gln Gly Arg Leu Thr Phe Pro Pro Arg Glu Ala Ala Gln Leu Leu Trp
    130                 135                 140

Met Gly Ala Leu Gly Ala Leu Thr Tyr Ala Leu Ser Arg Glu Gly Ala
145                 150                 155                 160

Gly Tyr Thr Gln Asp Leu Ala Leu Gln Lys Ala Lys Leu Asp Ile Thr
                165                 170                 175

Leu Val Ala Leu Phe Asn Ile Glu Glu Glu Gly Pro Ala Asp Ala Leu
            180                 185                 190

Asp Asp Phe Asp Leu Asp Met Leu Pro Ala Asp Ala Leu Asp Asp Phe
        195                 200                 205

Asp Leu Asp Met Leu Pro Ala Asp Ala Leu Asp Asp Phe Asp Leu Asp
    210                 215                 220

Met Leu Pro Gly Met Pro Lys Lys Lys Arg Lys Val
225                 230                 235
```

```
<210> SEQ ID NO 27
<211> LENGTH: 577
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

cacttctaaa taagcgaatt tcttatgatt tatgattttt attattaaat aagttataaa     60

aaaaataagt gtatacaaat tttaaagtga ctcttaggtt ttaaaacgaa aattcttgtt    120

cttgagtaac tctttcctgt aggtcaggtt gctttctcag gtatagcatg aggtcgctct    180

tattgaccac acctctaccg gcaaggtcag gctctatatc tgcgatatac tgagcatatc    240

ccccccaggc tctatatctg cgatatactg agcatatccc ccccaggctc tatatctgcg    300

atatactgag catatccccc ccaggctcta tatctgcgat atactgagca tatcccccca    360

ggctctatat ctgcgatata ctgagcatat ccccccaggc tctatatctg cgatatactg    420

agcatatccc aatggcatgc atgtgctctg tatgtatata aaactcttgt tttcttcttt    480

tctctaaata ttctttcctt atacattagg tcctttgtag cataaattac tatacttcta    540

tagacacgca aacacaaata cacacactaa attaata                             577


<210> SEQ ID NO 28
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

atgagtagat tggacaagtc taaggttatc aacggtgctt tggaattgtt gaacggtgtt     60

ggtatcgaag gtttgaccac cagaaagttg gctcaaaagt tgggtgttga acaaccaacc    120

ttgtactggc acgttaagaa caagagagct ttgttggacg ctttgccaat cgaaatgttg    180

gacagacacc acacccactt ctgtccattg gaaggtgaat cttggcaaga cttcttgaga    240
```

```
aacaacgcta agtctttcag atgtgctttg ctctctcacc gcgacggtgc taaggttcac    300

ttgggaacca gaccaaccga aaagcaatac gaaaccttgg aaaaccaatt ggctttcttg    360

tgtcaacaag gtttctcttt ggaaaacgct ttgtacgctt tgtctgctgt tggtcacttc    420

accttgggtt gtgttttgga agaacaagaa caccaagttg ctaaggaaga aagagaaacc    480

ccaaccaccg actctatgcc accattgctc agacaagcta tcgaattgtt cgacagacaa    540

ggtgctgaac cagctttctt gttcggtttg gaattgatca tctgtggttt ggaaaagcaa    600

ttgaagtgtg aatctggtgg gccggccgac gctttggacg acttcgactt ggacatgttg    660

ccagctgacg ctttggacga cttcgacttg gacatgttgc cagctgacgc tttggacgac    720

ttcgacttgg acatgttgcc aggttga                                        747
```

```
<210> SEQ ID NO 29
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ser Arg Leu Asp Lys Ser Lys Val Ile Asn Gly Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Ala Asp Ala Leu Asp Asp Phe Asp Leu Asp Met Leu Pro Ala Asp Ala
    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245
```

<210> SEQ ID NO 30
<211> LENGTH: 881
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
ggtctcacag tctcgatgga ttagtttctc acaggtaaca taacaaaaac caagaaaagc     60
ccgcttctga aaactacagt tgacttgtat gctaaagggc cagactaatg ggaggagaaa    120
aagaaacgaa tgtatatgct catttacact ctatatcacc atatggagga taagttgggc    180
tgagcttctg atccaattta ttctatccat tagttgctga tatgtcccac cagccaacac    240
ttgatagtat ctactcgcca ttcacttcca gcagcgccag tagggttgtt gagcttagta    300
aaaatgtgcg caccacaagc ctacatgact ccacgtcaca tgaaaccaca ccgtggggcc    360
ttgttgcgct aggaatagga tatgcgacga agacgcttct gcttagtaac cacaccacat    420
tttcaggggg tcgatctgct tgcttccttt actgtcacga gcggcccata atcgcgcttt    480
tttttaaaa ggcgcgagac agcaaacagg aagctcgggt ttcaaccttc ggagtggtcg    540
cagatctgga gactggatct ttacaataca gtaaggcaag ccaccatctg cttcttaggt    600
gcatgcgacg gtatccacgt gcagaacaac atagtctgaa gaagggggg aggagcatgt    660
tcattctctg tagcagtaag agcttggtga taatgaccaa aactggagtc tcgaaatcat    720
ataaatagac aatatatttt cacacaatga gatttgtagt acagttctat tctctctctt    780
gcataaataa gaaattcatc aagaacttgg tttgatattt caccaacaca cacaaaaaac    840
agtacttcac taaatttaca cacaaaacaa aatgagagac c                        881
```

<210> SEQ ID NO 31
<211> LENGTH: 792
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
ggtctcacag tgagcttggc ccattgcata cgttgtatcc atatcataat atgtacattt     60
atattggctc atgtccaaca ttaccgccat gttgacattg attattgact agttattaat    120
agtaatcaat tacggggtca ttagttcata gcccatatat ggagttccgc gttacataac    180
ttacggtaaa tggcccgcct ggctgaccgc ccaacgaccc ccgcccattg acgtcaataa    240
tgacgtatgt tcccatagta acgccaatag ggactttcca ttgacgtcaa tgggtggagt    300
atttacggta aactgcccac ttggcagtac atcaagtgta tcatatgcca agtacgcccc    360
ctattgacgt caatgacggt aaatggcccg cctggcatta tgcccagtac atgaccttat    420
gggactttcc tacttggcag tacatctacg tattagtcat cgctattacc atggtgatgc    480
ggttttggca gtacatcaat gggcgtggat agcggtttga ctcacgggga tttccaagtc    540
tccaccccat tgacgtcaat gggagtttgt tttggcacca aaatcaacgg gactttccaa    600
aatgtcgtaa caactccgcc ccattgacgc aaatgggcgg taggcgtgta cggtgggagg    660
tctatataag cagagctcgt ttagtgaacc gtcagatcgc ctgtagacgc catccacgct    720
gttttgacct ccatagaaga caccgggacc gatccagcct ccgcggcccg aattaattca    780
taatgagaga cc                                                        792
```

<210> SEQ ID NO 32
<211> LENGTH: 725
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
ggtctcgtga gactcctttt acttcggttg tgaaagaaag ttgacattat cgatttgggt 60
gacacggtga ttgaaaaagc aacgaccagt attatacctc tttttttat tattcagttt 120 atatttttgc aagtgatctt aagcatttct acacaaactt atgccaacgt gaccatttat 180
tattttatat agcaaaaaaa aatgaggggc cttgcagaac aattgttgcg agtttctaat 240
aacaagcacg tagaatattg gccatttaat ttttctcttc aatttataga atggttgtgt 300
tagtgacaaa aagaatattc ttccccgcca ggactcgaac ctggaatctc ctggttcgta 360
gccagacgcc gtgaccattg ggccacgagg aacaagaata taaagatctc tgagggcaag 420
gtatgcctat gtcgcaataa aatgtttgtt cctgcgcaaa agtaaagttc tattaatata 480
caactacaca gttatcggtt cacactattc gatagttgta aaaaccattt tgataaagat 540
ataacaaggc gtttattaag gacatttttg ctacaagtcg tgaagtattg attgtaggcg 600
atcgttggta actttctcca tatcggaata ttcaatattg aactcacccc tcccttgcga 660
taagctcctt agcttattgg tgtaggtggt aatttccctt agtggcactt tcgcttttcg 720
agacc 725

<210> SEQ ID NO 33
<211> LENGTH: 748
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33
ggtctcgtga gtcgccagtg ccatgtttct gccttcgacc ggaccttttt aagtacgata 60
aatatccttt tataaatata tagtctaaaa tatccattaa tactgtgctc aatcaatcgt 120
gttagatgat ttagtttttt ccaaatcgtt attatagtgc agaagtagta tacataaagg 180
catatgcatg cgatttggaa gtaacgctcg ccgtagacaa gtaagaatgc ctgctgtctt 240
gagaaccagg tccaaagaat cctctataga gcagaagcct gcttccagaa ctagaacgag 300
atcaagaagg ggcaagcgtg gtcgtgacga tgatgatgat gacgacgatg aggaaagcga 360
tgatgcatac gatgaagtag gtaatgacta tgacgagtat gcttcaagag cgaagctggc 420
caccaatagg cccttcgaaa tagtcgcggg actgcctgct agtgtggagc tgcccaacta 480
taactcttcg cttactcatc cgcaatcaat taaaaattct ggggtgcttt acgactctct 540
ggtcagttcc agaagaacct gggttcaggg tgagatgttt gaactgtatt ggcgaagacc 600
taagaaaatt gttagtgaat ctaccccagc agcgacggag agtccaacat ctggaacgat 660
tcctttgatt cgagataaga tgcagaaaat gtgcgattgt gtaatgagtg gaggtcctca 720
cacgttcaaa gttagacttt tggagacc 748

<210> SEQ ID NO 34
<211> LENGTH: 573
<212> TYPE: DNA
<213> ORGANISM: Artificial Sequence -continued

```
<220> FEATURE:
<223> OTHER INFORMATION: Description of Artificial Sequence: Synthetic
      polynucleotide

<400> SEQUENCE: 34

ggtctcatga gaaaagacac acatgcgagc tttcgaacct cagatgctaa tattacgtgt     60

tatatatacc aaactttata aaatgacata gatattttat gctgtgatag ctttcctgtt    120

atggagaagc tcttcttatt ccccctgtca actttcatac tcttgtagaa tttcctttat    180

gataggttta tcgcttacga atttagactt tgatgtgatg ggtttggcac ctgttctttt    240

tccacaacct ttgcgtgcct catcaatagc gtttgatctg tcgggaaatt tgtatttgta    300

gagtgcatcc ttgcacattg tatagaccca attacgctct tctaacaggt tcacgaacga    360

ttttatttca ggaacagagc cgattgtact tttgaacct ataatgatca gcttggattt    420

ggcccttgtc atggcaacat tgactcttct tagctctttc agcagcgctc ctccatttaa    480

ttgagaattt cttctaacca tggaaataat aatgcacttt ttgtcacgac cttgaaactg    540

atcagcagtc aagatctcta gcttttagag acc                                 573


<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

atgccaaaga agaagagaaa ggtt                                            24


<210> SEQ ID NO 36
<211> LENGTH: 18
<212> TYPE: DNA
<213> ORGANISM: Mycobacterium sp.

<400> SEQUENCE: 36

aagatgaccg gtcacctt                                                   18
```

ORTHOGONAL TRANSCRIPTIONAL SWITCHES DERIVED FROM TET REPRESSOR HOMOLOGS FOR *SACCHAROMYCES CEREVISIAE*

RELATED APPLICATIONS

The present application is a 35 U.S.C. § U.S. national entry of International Application PCT/US2017/065067, filed Dec. 7, 2017, which claims the benefit of U.S. Provisional Application 62/431,170 filed on Dec. 7, 2016. The entire contents of these applications are incorporated herein by reference in their entirety.

GOVERNMENT LICENSE RIGHTS

This invention was made with government support under grant number N66001-12-C-4020 awarded by the Defense Advanced Research Projects Agency. The government has certain rights in the invention.

FIELD OF THE INVENTION

This invention relates generally to the field of yeast genetics.

BACKGROUND OF THE INVENTION

The yeast *Saccharomyces cerevisiae* is the premiere eukaryote for biotechnology, and the first to be sequenced. The organism benefits from the powerful genetic tools available to reveal gene functions, such as various mutant libraries, including the gene knockout collection and the overexpression collection that utilizes the intrinsic GAL1 promoter (GAL1pr) as a means to individually express genes at a high level. However, the popular GAL1pr has some potential disadvantages because it a) requires a high concentration of galactose to induce expression, b) leads to slow growth relative to glucose medium, and c) may affect fundamental metabolism in a manner unrelated to the overexpressed gene product. Furthermore, being able to regulate different pathways independently in the same cell requires a series of distinct orthogonal promoter systems, each activated or repressed by its own ligand. As such, prior to the invention described herein, there was a pressing need to develop a palette of diverse chemically regulated promoters.

SUMMARY OF THE INVENTION

The invention is based, at least in part, on the surprising identification of orthogonal transcriptional switches derived from Tet repressor homologs for *Saccharomyces cerevisiae* regulated by 2,4-diacetylphloroglucinol (DAPG) and other ligands. Accordingly, described herein is a unique system regulated by DAPG, cumic acid, and other ligands, which systems are orthogonal (i.e., no cross-talk) to previously described Tet and camphor regulated systems.

Provided herein is a system for regulating gene expression in yeast comprising a repressible gene expression construct (e.g., plasmid) comprising a regulator binding sequence and a target gene sequence, wherein the regulator binding sequence comprises a phlO nucleic acid sequence; and a transcriptional activator expression construct (e.g., plasmid) comprising a phlF nucleic acid sequence, wherein the transcriptional activator binds to the regulator binding sequence in the absence of 2,4-diacetylphloroglucinol (DAPG) and wherein binding of the transcriptional activator to the regulator binding sequence is inhibited in the presence of DAPG.

In some cases, binding of the regulator binding sequence to the transcriptional activator in the absence of DAPG results in expression of the target gene sequence downstream from the regulator binding sequence. In this case, the repressible gene expression construct further comprises a transcription terminator sequence. For example, the transcriptional terminator sequence is located upstream of the regulator binding sequence. A person of ordinary skill in the art would recognize that the term "upstream" in this case means that the terminator sequence is placed before the regulator binding sequence. Optionally, the transcriptional terminator sequence comprises a nucleic acid sequence encoding alcohol dehydrogenase 1 (ADH1). In some cases, the regulator binding sequence comprises at least one copy of a nucleic acid sequence of phlO, wherein the sequence of phlO comprises SEQ ID NO: 3, e.g., at least two copies, at least three copies, at least four copies, at least five copies, at least six copies, at least seven copies, at least eight copies, at least nine copies, or at least ten copies of a nucleic acid sequence of phlO. In one aspect, the repressible gene expression construct further comprises a promoter downstream from the regulator binding sequence, i.e., the promoter is placed after the regulator binding sequence. Optionally, the promoter downstream from the regulator binding sequence lacks an upstream activating sequence. For example, the promoter downstream from the regulator binding sequence comprises a cytochrome c isoform 1 (CYC1) promoter.

In one aspect, the transcription enhancer expression construct comprises a nucleic acid sequence encoding PhlF operatively connected to a transcriptional activation domain to form PhlTA. Optionally, the transcriptional activation domain comprises at least one VP16 tandem repeat, e.g., at least two, at least three, at least four, at least five, at least six, at least seven, at least eight, at least nine, or at least ten VP16 tandem repeats. In some cases, the transcription enhancer expression construct further comprises a nuclear localization signal (NLS). In some cases, the NLS is derived from SV40. In one aspect, the transcription enhancer expression construct further comprises a promoter sequence comprising the human cytomegalovirus promoter (CMV).

In other cases, the binding of the regulator binding sequence to the transcriptional activator in the absence of DAPG results in inhibition of expression of the target gene sequence downstream from the regulator binding sequence. In one aspect, the regulator binding sequence comprises at least one copy of a nucleic acid sequence of phlO, wherein the sequence of phlO comprises SEQ ID NO: 3, e.g., at least two copies, at least three copies, at least four copies, at least five copies, at least six copies, at least seven copies, at least eight copies, at least nine copies, or at least ten copies of a nucleic acid sequence of phlO. Optionally, the repressible gene expression construct further comprises a promoter upstream of the regulator binding sequence. For example, the promoter upstream of the regulator binding sequence comprises an ADH1 promoter (ADH1pr). In some cases, the transcription enhancer expression construct comprises a nucleic acid sequence encoding a PhlF transcription regulator domain operatively linked to a nuclear localization signal (NLS) domain. In one aspect, the transcription enhancer expression construct further comprises a promoter sequence comprising the glyceraldehyde-3-phosphate dehydrogenase 1 promoter (TDH1pr).

Also provided is a recombinantly engineered cell comprising a repressible gene expression construct comprising a regulator binding sequence and a target gene sequence, wherein the regulator binding sequence comprises a phlO nucleic acid sequence; and a transcriptional activator expression construct comprising a phlF nucleic acid sequence. In some cases, the presence of DAPG inhibits expression of the target gene sequence. In other cases, the presence of DAPG induces expression of the target gene sequence. For example, the cell comprises a *Saccharomyces cerevisiae* cell.

Transcription enhancer expression constructs comprising a nucleic acid sequence encoding a PhlF transcription regulator domain operatively linked to a transcriptional activation domain to form phlTA is also provided. Described herein are recombinantly expressed transcriptional enhancers comprising a PhlF transcription regulator domain and a transcriptional activator domain, wherein the transcriptional activator domain comprises VP16.

An exemplary nucleic acid sequence for the transcription enhancer expression construct for the DAPG-OFF system (PhlTA; PhlF-VP16 in pSIB337) is provided below (1-600, PhlF; 601-726, VP16; 727-729, stop codon; SEQ ID NO: 9):

```
atggctagaaccccatctcgatcttctatcggttctttgcgatctccaca
cacccacaaggctatcttgacctctaccatcgaaatcttgaaggaatgtg
gttactctggtttgtctatcgaatctgttgctagaagagctggtgcttct
aagccaaccatctacagatggtggaccaacaaggctgctttgatcgctga
agtttacgaaaacgaatctgaacaagttagaaagttcccagacttgggtt
ctttcaaggctgacttggacttcttgttgagaaacttgtggaaggtttgg
agagaaaccatctgtggtgaggctttcagatgtgttatcgctgaagctca
attggacccagctaccttgacccaattgaaggaccaattcatggaaagaa
gaagagaaatgccaaagaagttggttgaaaacgctatctctaacggtgaa
ttgccaaaggacaccaacagagaattgttgaggacatgatcttcggtttc
tgttggtacagattgttgaccgaacaattgaccgttgaacaagacatcga
agagttcaccttcttgttgatcaacggtgtttgtccaggaacccaaagag
ggccggccgacgctttggacgacttcgacttggacatgttgcctgcagat
gcacttgatgattttgatcttgatatgcttccagcagacgcattggatga
ctttgaccttgacatgcttcctggttga
```

An exemplary amino acid sequence for the transcription enhancer expression construct for the DAPG-OFF system (PhlTA; PhlF-VP16 in pSIB337) is provided below (SEQ ID NO: 10):

```
MARTPSRSSIGSLRSPHTHKAILTSTIEILKECGYSGLSIESVARRAGAS
KPTIYRWWTNKAALIAEVYENESEQVRKFPDLGSFKADLDFLLRNLWKVW
RETICGEAFRCVIAEAQLDPATLTQLKDQFMERRREMPKKLVENAISNGE
LPKDTNRELLLDMIFGFCWYRLLTEQLTVEQDIEEFTFLLINGVCPGTQR
GPADALDDFDLDMLPADALDDFDLDMLPADALDDFDLDMLPG
```

Optionally, the recombinantly expressed transcriptional enhancers further comprise an NLS domain.

Also described herein are transcription enhancer expression constructs comprising a nucleic acid sequence encoding a PhlF transcription regulator domain operatively linked to a nuclear localization signal (NLS) domain.

An exemplary nucleic acid sequence for the transcription enhancer expression construct for the DAPG-ON system (NLS-PhlF in pSIB921) is provided below (1-24, NLS from SV40; 25-621, PhlF; 622-624, STOP codon; SEQ ID NO: 11):

```
atgccaaagaagaagagaaaggttgctagaaccccatctcgatcttctat
cggttctttgcgatctccacacacccacaaggctatcttgacctctacca
tcgaaatcttgaaggaatgtggttactctggtttgtctatcgaatctgtt
gctagaagagctggtgcttctaagccaaccatctacagatggtggaccaa
caaggctgctttgatcgctgaagtttacgaaaacgaatctgaacaagtta
gaaagttcccagacttgggttctttcaaggctgacttggacttcttgttg
agaaacttgtggaaggtttggagagaaaccatctgtggtgaggctttcag
atgtgttatcgctgaagctcaattggacccagctaccttgacccaattga
aggaccaattcatggaaagaagaagagaaatgccaaagaagttggttgaa
aacgctatctctaacggtgaattgccaaaggacaccaacagagaattgtt
gttggacatgatcttcggtttctgttggtacagattgttgaccgaacaat
tgaccgttgaacaagacatcgaagagttcaccttcttgttgatcaacggt
gtttgtccaggaacccaaagatga
```

An exemplary amino acid sequence for the transcription enhancer expression construct for the DAPG-ON system (NLS-PhlF in pSIB921) is provided below (SEQ ID NO: 12):

```
MPKKKRKVARTPSRSSIGSLRSPHTHKAILTSTIEILKECGYSGLSIESV
ARRAGASKPTIYRWWTNKAALIAEVYENESEQVRKFPDLGSFKADLDFLL
RNLWKVWRETICGEAFRCVIAEAQLDPATLTQLKDQFMERRREMPKKLVE
NAISNGELPKDTNRELLLDMIFGFCWYRLLTEQLTVEQDIEEFTFLLING
VCPGTQR
```

Provided are recombinantly expressed transcriptional enhancers comprising a PhlF transcription regulator domain and an NLS domain.

Also provided are repressible gene expression constructs comprising a regulator binding sequence and a target gene sequence, wherein the regulator binding sequence is capable of binding a PhlF transcriptional regulator in the absence of DAPG. In some cases, binding of the regulator binding sequence to the PhlF transcriptional regulator leads to expression of the target gene downstream from the regulator binding sequence.

An exemplary nucleic acid sequence for the repressible gene expression construct for the DAPG-OFF system (PhlPr; ADH1tr-phlF operator-CYC1pr in PSIB918) is provided below (1-203, ADH1 transcriptional terminator; 215-494, phlF operator; 507-653, CYC1 promoter; SEQ ID NO: 13):

```
cacttctaaataagcgaatttcttatgatttatgatttttattattaaat
aagttataaaaaaaataagtgtatacaaattttaaagtgactcttaggtt
ttaaaacgaaaattcttgttcttgagtaactctttcctgtaggtcaggtt
gctttctcaggtatagcatgaggtcgctcttattgaccacacctctaccg
```

-continued gcaggccggcccggtatgtatgatacgaaacgtaccgtatcgttaaggta gcgttatgtatgatacgaaacgtaccgtatcgttaaggtagcgttatgta tgatacgaaacgtaccgtatcgttaaggtagcgttatgtatgatacgaaa cgtaccgtatcgttaaggtagcgttatgtatgatacgaaacgtaccgtat cgttaaggtagcgttatgtatgatacgaaacgtaccgtatcgttaaggta gcgttatgtatgatacgaaacgtaccgtatcgttaaggtagcgtcccggg ccggcctatggcatgcatgtgctctgtatgtatataaaactcttgttttc ttcttttctctaaatattctttccttatacattaggtcctttgtagcata aattactatacttctatagacacgcaaacacaaatacacacactaaatta ata An exemplary regulator binding sequence (core) bound by PhlTA (PhlF-VP16) placed between the terminator and the UAS-less promoter (e.g., ADH1tr and CYC1pr) is provided below (SEQ ID NO: 14):

atgatacgaaacgtaccgtatcgttaaggt

In other cases, binding of the regulator binding sequence to the PhlF transcriptional regulator leads to inhibition of expression of the target gene downstream from the regulator binding sequence.

An exemplary nucleic acid sequence for the repressible gene expression construct for the DAPG-ON system (ADH-phO2 in pSIB924; ADH1pr-phlF operator double) is provided below (SEQ ID NO: 15):

taaagtccaatgctagtagagaagggggtaacacccctccgcgctcttt tccgatttttttctaaaccgtggaatatttcggatatccttttgttgttt ccgggtgtacaatatggacttcctcttttctggcaaccaaacccatacat cgggattcctataataccttcgttggtcaccctaacatgtaggtggcgga ggggagatatacaatagaacagataccagacaagacataatgggctaaac aagactacaccaattacactgcctcattgatggtggtacataacgaacta atactgtagccctagacttgatagccatcatcatatcgaagtttcactac cctttttccatttgccatctattgaagtaataataggcgcatgcaacttc ttttcttttttttttcttttttctctctcccccgttgttgtctcaccatatc cgcaatgacaaaaaaatgatggaagacactaaaggaaaaaattaacgaca aagacagcaccaacagatgtcgttgttccagagctgatgaggggtatctc gaagcacacgaaactttttccttccttcattcacgcacactactctctaa tgagcaacggtatacggccttccttccagttacttgaatttgaaataaaa aaaagtttgctgtcttgctatcaagtataaatagacctgcaattatgtat gatacgaaacgtaccgtatcgttaaggtagcgtatgatacgaaacgtacc gtatcgttaaggtagcgtctttcttccttgtttctttttctgcaggtcga ctctagaggatccccgggtattaa In one aspect, the regulator binding sequence (core and its flanking region; SEQ ID NO: 16) is doubled in SEQ ID NO: 15, i.e., SEQ ID NO: 15 (positions 693-732) contains double copies of SEQ ID NO: 16. SEQ ID NO: 16 is set forth below:

atgatacgaaacgtaccgtatcgttaaggtagcgt

In one aspect, SEQ ID NO: 15 (amino acid positions 693-732) contains double copies of the regulator binding sequence (core and its flanking region) SEQ ID NO: 16.

Systems for expression control of at least two peptide molecules comprise a first peptide molecule expressed under control of a first repressible promoter; and a second peptide molecule expressed under control of a transcriptional activator comprising a PhlF transcription regulator domain and a transcriptional activation domain, wherein the at least two peptide molecules are capable of being expressed in a eukaryotic cell. For example, the system is expressed in an *S. cerevisiae* cell.

Systems for regulating gene expression in yeast comprise a repressible gene expression construct (e.g., plasmid) comprising a regulator binding sequence and a target gene sequence, wherein the regulator binding sequence is capable of binding a CymR transcriptional regulator; and a transcriptional activator expression construct (e.g., plasmid) comprising a cymR nucleic acid sequence, wherein the transcriptional activator binds to the regulator binding sequence in the absence of p-comate and wherein transcriptional activator binding to the regulator binding sequence is inhibited in the presence of p-cumate.

An exemplary nucleic acid sequence for the transactivator construct for the cumate-OFF system (cymTA in pSIB470; NLS-CymR-VP16) is provided below (1-24, NLS(SV40); 25-633, CymR; 634-759, VP16; 760-762, Stop codon; SEQ ID NO: 17):

atgccaaagaagaagagaaaggtaatgtctccaaagagaagaactcaagc tgaaagagctatggaaactcaaggtaagttgatcgctgctgctttgggtg ttttgagagaaaagggttacgctggtttcagaatcgctgacgttccaggt gctgctggtgtttctagaggtgctcaatctcaccacttcccaaccaagtt ggaattgttgttggctaccttcgaatggttgtacgaacaaatcaccgaaa gatctagagctagattggctaagttgaagccagaagacgacgttatccaa caaatgttggacgacgctgctgaattcttcttggacgacgacttctctat ctctttggacttgatcgttgctgctgaccgcgatcctgctttgagagaag gtatccaaagaaccgttgaaagaaacagattcgttgttgaagacatgtgg ttgggtgttttggtttctagaggtttgtctcgcgacgacgctgaagacat cttgtggttgatcttcaactctgttagaggtttggctgttagatctttgt ggcaaaaggacaaggaaagattcgaaagagttagaaactctaccttggaa atcgctagagaaagatacgctaagttcaagagggggccggccgacgcttt ggacgacttcgacttggacatgttgcctgcagatgcacttgatgattttg atcttgatatgcttccagcagacgcattggatgactttgaccttgacatg cttcctggttga An exemplary amino acid sequence for the transactivator construct for the cumate-OFF system (cymTA in pSIB470; NLS-CymR-VP16) is provided below (SEQ ID NO: 18):

```
MPKKKRKVMSPKRRTQAERAMETQGKLIAAALGVLREKGYAGFRIADVPG

AAGVSRGAQSHHFPTKLELLLATFEWLYEQITERSRARLAKLKPEDDVIQ

QMLDDAAEFFLDDDFSISLDLIVAADRDPALREGIQRTVERNRFVVEDMW

LGVLVSRGLSRDDAEDILWLIFNSVRGLAVRSLWQKDKERFERVRNSTLE

IARERYAKFKRGPADALDDFDLDMLPADALDDFDLDMLPADALDDFDLDM

LPG
```

An exemplary nucleic acid sequence for the promoter construct for the cumate-OFF system (cymPR; ADH1tr-cymR operator-CYC1pr) is provided below (1-203, ADH1 transcriptional terminator; 208-417, label=cymR operator; 419-564, CYC1 promoter; SEQ ID NO: 19):

```
cacttctaaataagcgaatttcttatgatttatgatttttattattaaat

aagttataaaaaaaataagtgtatacaaattttaaagtgactcttaggtt

ttaaaacgaaaattcttgttcttgagtaactctttcctgtaggtcaggtt

gctttctcaggtatagcatgaggtcgctcttattgaccacacctctaccg

gcaaggtaagaaagaaacaaaccaacctgtctgtattatctcaagaaaga

aacaaaccaacctgtctgtattatctcaagaaagaaacaaaccaacctgt

ctgtattatctcaagaaagaaacaaaccaacctgtctgtattatctcaag

aaagaaacaaaccaacctgtctgtattatctcaagaaagaaacaaaccaa

cctgtctgtattatctcaatggcatgcatgtgctctgtatgtatataaaa

ctcttgttttcttcttttctctaaatattctttccttatacattaggtcc

tttgtagcataaattactatacttctatagacacgcaaacacaaatacac

acactaaattaata
```

Exemplary regulator binding nucleic acid sequences are provided below (Mullick et al., 2006 BMC Biotechnology, 6:43, incorporated herein by reference):

```
                                   (SEQ ID NO: 20)
AGAAACAAACCAACCTGTCTGTATTA

                                   (SEQ ID NO: 21)
AACAAACAGACAATCTGGTCTGTTTGTA.
```

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%. An alteration may be a change in sequence relative to a reference sequence or a change in expression level, activity, or epigenetic marker.

By "agent" is meant any small molecule chemical compound, antibody, nucleic acid molecule, or polypeptide, or fragments thereof.

By "binding to" a molecule is meant having a physicochemical affinity for that molecule.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

By "control" or "reference" is meant a standard of comparison. As used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection, the amount and measurement of the change can vary. Determination of statistical significance is within the ability of those skilled in the art, e.g., the number of standard deviations from the mean that constitute a positive result.

As used herein, "detecting" and "detection" are understood that an assay performed for identification of a specific analyte in a sample, e.g., an antigen in a sample or the level of an antigen in a sample. The amount of analyte or activity detected in the sample can be none or below the level of detection of the assay or method.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "polynucleotide" or "nucleic acid" as used herein designates mRNA, RNA, cRNA, cDNA or DNA. As used herein, a "nucleic acid encoding a polypeptide" is understood as any possible nucleic acid that upon (transcription and) translation would result in a polypeptide of the desired sequence. The degeneracy of the nucleic acid code is well understood. Further, it is well known that various organisms have preferred codon usage, etc. Determination of a nucleic acid sequence to encode any polypeptide is well within the ability of those of skill in the art.

As used herein, "isolated" or "purified" when used in reference to a polypeptide means that a polypeptide or protein has been removed from its normal physiological environment (e.g., protein isolated from plasma or tissue, optionally bound to another protein) or is synthesized in a non-natural environment (e.g., artificially synthesized in an in vitro translation system or using chemical synthesis).

Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. An isolated virus or viral vector is a virus that is removed from the cells, typically in culture, in which the virus was produced.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

As used herein, "kits" are understood to contain at least one non-standard laboratory reagent for use in the methods of the invention in appropriate packaging, optionally containing instructions for use. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

The term "gene" refers to a segment of deoxyribonucleic acid that encodes a polypeptide including the upstream and downstream regulatory sequences. Specifically, the term gene includes the promoter region upstream of the gene.

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

"Obtaining" is understood herein as manufacturing, purchasing, or otherwise coming into possession of.

As used herein, "operably linked" is understood as joined, preferably by a covalent linkage, e.g., joining an amino-terminus of one peptide, e.g., expressing an enzyme, to a carboxy terminus of another peptide, e.g., expressing a signal sequence to target the protein to a specific cellular compartment; joining a promoter sequence with a protein coding sequence, in a manner that the two or more components that are operably linked either retain their original activity, or gain an activity upon joining such that the activity of the operably linked portions can be assayed and have detectable activity, e.g., enzymatic activity, protein expression activity.

The term "promoter" or "promoter region" refers to a minimal sequence sufficient to direct transcription or to render promoter-dependent gene expression that is controllable for cell-type specific or tissue-specific gene expression, or is inducible by external signals or agents. Promoters may be located in the 5' or 3' regions of the gene. In general, a promoter includes, at least, 50, 75, 100, 125, 150, 175, 200, 250, 300, 400, 500, 750, 1000, 1500, or 2000 nucleotides upstream of a given coding sequence. One of skill in the art will appreciate that a promoter location may vary outside these parameters for some genes, and also that some genes may comprise more than one promoter (e.g., multiple tissue specific promoters).

As used herein, "plurality" is understood to mean more than one. For example, a plurality refers to at least two, three, four, five, or more.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments). Optionally the peptide further includes one or more modifications such as modified peptide bonds, i.e., peptide isosteres, and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins, Structure and Molecular Properties, 2nd ed., T. E. Creighton, W.H. Freeman and Company, New York (1993); Posttranslational Covalent Modification of Proteins, B. C. Johnson, ed., Academic Press, New York, pgs. 1-12 (1983); Seifter et al., Meth. Enzymol 182:626-646 (1990); Rattan et al., Ann. N.Y. Acad. Sci. 663:48-62 (1992)).

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The term "reduce" or "increase" is meant to alter negatively or positively, respectively, by at least 5%. An alteration may be by 5%, 10%, 25%, 30%, 50%, 75%, or even by 100%.

A "sample" as used herein refers to a biological material that is isolated from its environment (e.g., blood or tissue from an animal, cells, or conditioned media from tissue culture) and is suspected of containing, or known to contain an analyte, such as a protein. A sample can also be a partially purified fraction of a tissue or bodily fluid. A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

A "subject" as used herein refers to an organism. In certain embodiments, the organism is an animal. In certain embodiments, the subject is a living organism. In certain embodiments, the subject is a cadaver organism. In certain preferred embodiments, the subject is a mammal, including, but not limited to, a human or non-human mammal. In certain embodiments, the subject is a domesticated mammal or a primate including a non-human primate. Examples of subjects include humans, monkeys, dogs, cats, mice, rats, cows, horses, goats, and sheep. A human subject may also be referred to as a patient.

A "subject sample" can be a sample obtained from any subject, typically a blood or serum sample, however the method contemplates the use of any body fluid or tissue from a subject. The sample may be obtained, for example, for diagnosis of a specific individual for the presence or absence of a particular disease or condition.

Ranges provided herein are understood to be shorthand for all of the values within the range.

By "reduces" is meant a negative alteration of at least 5%, 10%, 25%, 50%, 75%, or 100%.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, at least 70%, at least 75%, more preferably 80% or 85%, and more preferably 90%, 95% or even 99% identical to the amino acid or nucleic acid sequence used for comparison.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Unless specifically stated or obvious from context, as used herein, the term "or" is understood to be inclusive. Unless specifically stated or obvious from context, as used herein, the terms "a", "an", and "the" are understood to be singular or plural.

The term "vector" is used to describe a nucleic acid molecule capable of expressing a desired peptide or protein construct in a given organism. A recombinant "vector" brings together various elements of the peptide or protein to be expressed, which provides the properties described in this application. In general, vectors used in recombinant DNA techniques arc referred to as "plasmids" or double stranded DNA molecules that arc capable of replicating and utilize the cellular machinery of their host to express their particular target peptide or protein. In some instances, plasmids are used to incorporate a desired gene sequence in a particular site of a chromosome of a eukaryotic cell, such as a *S. cerevisiae* cell.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is a schematic diagram of DAPG (PhlF)-OFF system using GFP as a reporter. The transactivator PhlTA, consisting of PhlF and VP16 binds to the phlO (phlF operator) region of promoter phlPr (=ADH1tr-phlO-CYC1pr) in the absence of DAPG. This results in steady expression of gfp. FIG. 1B-FIG. 1D shows flow cytometric analyses in which FITC-A shows the intensity of GFP fluorescence. Strain BY4741 is wild type lacking a gfp gene, and DapG-TA is a BY4741-based strain that carries gfp gene under control of the DAPG-switch. FIG. 1B is a graph showing BY4741 in SC and Strain DapG-TA in SC (solid line). FIG. 1C is a graph showing DapG-TA in SC and with (solid line) and without 12 μM DAPG (broken line). FIG. 1D is a graph showing DapG-TA in SC and with (solid line) and without 48 μM of DAPG (broken line). The broken lines in FIG. 1C and FIG. 1D are the same. FIG. 1E is a line graph showing time course of GFP fluorescence. The y-axis is the mean fluorescence values out of 10,000 counts. Red circles and blue squares represent DapG-TA cells grown in the absence or presence of 48-μM DAPG, respectively. Green triangles show BY4741 grown without DAPG. The plotted values are averages from four independent experiments, and the error bars reflect standard deviations that are not visible because of their small size.

DETAILED DESCRIPTION

Figure 1:
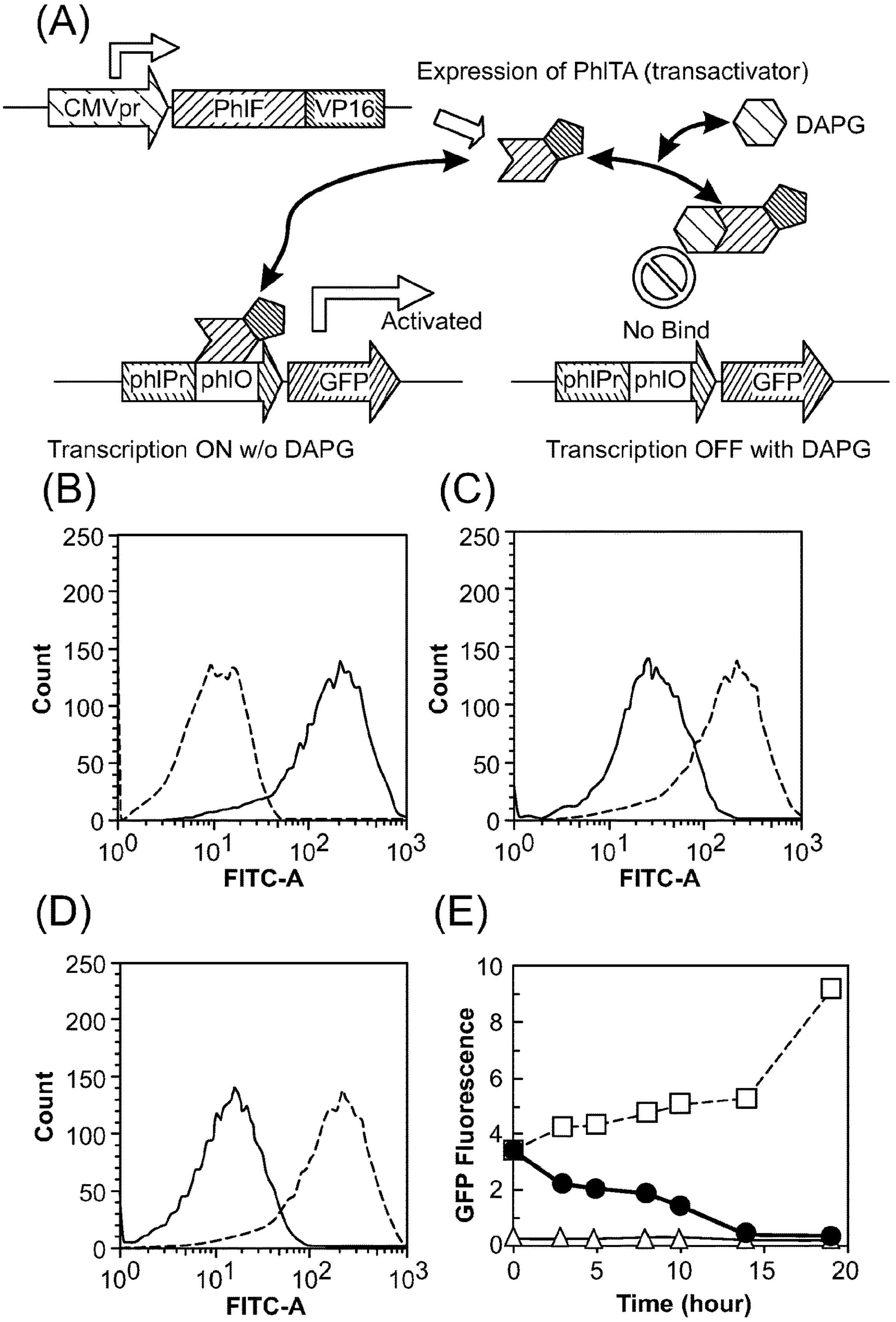
FIG. 1A-FIG. 1E is a series of schematics and graphs showing the characteristics of the DAPG-Off switch.

The invention is based, at least in part, on the surprising identification of a unique promoter regulated by DAPG, cumic acid, and other ligands, which are orthogonal (i.e., no cross talk) to previously described Tet and camphor regulated systems. Accordingly, described herein are orthogonal transcriptional switches derived from Tet repressor homologs for *Saccharomyces cerevisiae* regulated by 2,4-diacetylphloroglucinol (DAPG) and other ligands.

The yeast *Saccharomyces cerevisiae* is the premiere eukaryote for biotechnology, and the first to be sequenced (Goffeau et al., 1996 Science, (274)546: 563-567). More recently, the first synthetic eukaryotic chromosomes and chromosome fragments of *S. cerevisiae* chromosome synIXR, semi-synVIL, synIII were built through a synthetic yeast genome project, Sc2.0 (Annaluru et al., 2014 Science, 344: 55-58; Dymond et al., 2011 Nature, 477: 471-476). The organism benefits from the powerful genetic tools available to reveal gene functions, such as various mutant libraries, including the gene knockout collection (Giaever et al., 2002 Nature, 418: 387-391) and the overexpression collection that utilizes the intrinsic GAL1 promoter (GAL1pr) as a means to individually express genes at a high level (Gelperin et al., 2005 Genes Dev, 19: 2816-2826). However, the popular GAL1pr has some potential disadvantages because it a) requires a high concentration of galactose to induce expression, b) leads to slow growth relative to glucose medium, and c) may affect fundamental metabolism in a manner unrelated to the overexpressed gene product. Furthermore, being able to regulate different pathways independently in the same cell requires a series of distinct orthogonal promoter systems, each activated or repressed by its own ligand. Thus, as described herein, it is highly desirable to have a palette of diverse chemically regulated promoters.

Another option for regulated expression of genes of interest is to use a synthetic promoter comprised of functional units from other species. The Tet-Off® and Tet-On® systems are among the most popular expression switches that take advantage of the synthetic promoter. The Tet system is originally from *Escherichia coli*, in which the transcriptional regulator TetR binds to its operator sequence (tetO) only in the absence of its ligands, such as tetracycline and doxycycline (Ramos et al., 2005 Microbiol. Mol. Biol. Rev., 69:326-356). Notably, the Tet system can be applied to various species, such as mammalian cells and yeast (Gari et al., 1997 Yeast, 13:837-848; Lewandoski, M. 2001 Nat. Rev. Genet., 2:743-755; Urlinger et al., 2000 Proceedings of the National Academy of Sciences U.S.A., 97:7963-7968). With respect to the key component TetR, there are a vast number of TetR homologs in bacteria and metagenomic samples (Ramos et al., 2005 Microbiol. Mol. Biol. Rev., 69:326-356; Stanton et al., 2014 Nat. Chem. Biol., 10:99-105), some of which have well-known operators and ligands. Recently, it was reported that one of the TetR homologs *Pseudomonas putida* CamR was utilized for the development of the camphor-Off switch in yeast, analogous to the Tet-Off® switch (Ikushima et al., 2015 G3 (Bethesda) 5, 1983-1990). Camphor, the ligand for CamR, prevents binding between CamR and its operator (camO), resulting in camphor-dependent expression of reporter genes under the control of the camO-containing promoter. Moreover, camphor was found to have little impact on yeast growth. On the other hand, an IPTG-On switch is available, and exploits another *E. coli* repressor, Lad, in yeast (Grilly et al., 2007 Mol. Syst. Biol., 3:127). Using this system, a reporter gene was activated only in the presence of the Lad ligand IPTG (Isopropyl β-D-1-thiogalactopyranoside).

Similar to the research in yeast, TetR homologs have been developed as switches in heterologous organisms other than yeast. One of them is a 2,4-diacetylphloroglucinol (DAPG)-based switch using phlF gene in bacteria and mammalian cells (Stanton et al., 2014 ACS Synth. Biol., 3: 880-891). The transcriptional repressor PhlF from *Pseudomonas fluorescens* and related species, known to be a distant homolog of TetR, regulates expression of the DAPG biosynthetic gene phlA in a DAPG-dependent manner (Abbas et al., 2002 J Bacteriol., 184: 3008-3016; Ramette et al., 2011 Appl. Microbiol., 34: 180-188; Schnider-Keel et al., 2000 J Bacteriol, 182: 1215-1225). Besides, other TetR homologs, namely EthR and CymR, have been applied as expression switches in heterologous organisms other than yeast (Eaton, R. W. 1997 J Bacteriol, 179: 3171-3180; Mullick et al., 2006 BMC Biotechnol., 6: 43; Weber et al., 2008 Proceedings of the National Academy of Sciences U.S.A., 105: 9994-9998; Kaczmarczyk et al., 2013 Appl. Environ. Microbiol., 79: 6795-6802).

As described in detail below, TetR homologs were engineered to develop expression switches in yeast. Specifically, described herein are well-behaved switches that depend on DAPG (both off and on) and p-cumate (off). In particular, DAPG showed little effect on yeast growth at working concentrations for the system. Also described herein is the possibility and challenges of developing additional ligand-regulated TetR homolog-based expression switches in yeast.

Accordingly, described herein is the development of tightly regulated expression switches in yeast, by engineering distant homologs of *Escherichia coli* TetR, including the transcriptional regulator PhlF from *Pseudomonas* and others. Previous studies demonstrated that the PhlF protein bound its operator sequence (phlO) in the absence of 2,4-diacetylphloroglucinol (DAPG) but dissociated from phlO in the presence of DAPG. Thus, described in detail below is the development of a DAPG-Off system in which expression of a gene preceded by the phlO-embedded promoter was activated by a fusion of PhlF to a multimerized viral activator protein (VP16) domain in a DAPG-free environment but repressed when DAPG was added to growth medium. In addition, a DAPG-On system with the opposite behavior of the DAPG-Off system was constructed, i.e., DAPG triggers the expression of a reporter gene. Exposure of DAPG to yeast cells did not cause any serious deleterious effect on yeast physiology in terms of growth. Efforts to engineer additional Tet repressor homologs were partially successful and a known mammalian switch, the p-cumate switch based on CymR from *Pseudomonas*, was found to function in yeast. Orthogonality between the TetR (doxycycline), CamR (D-camphor), PhlF (DAPG), and CymR (p-cumate)-based Off switches was demonstrated by evaluating all 4 ligands against suitably engineered yeast strains. This study expands the toolbox of "On-" and "Off-" switches for yeast biotechnology.

Kits

The invention provides kits. In one embodiment, the kit includes one or more of the plasmids/constructs described herein, along with any of the ligands described herein, e.g., DAPG. In some embodiments, the kit comprises a sterile container; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1: Materials and Methods

The following materials and methods were utilized in the examples described herein.

Media

Yeast strains were cultured in YPD or SD-based medium supplemented with needed nutrients. SC is a fully supplemented medium of SD, and SC lacking three components, such as leucine, histidine, and adenine, is referred to as SC-Leu-His-Ade. The following drugs added to yeast media were purchased from Santa Cruz Biotechnology (Dallas, TX); 2,4-diacetylphloroglucinol (DAPG), coumesterol, and gentamicin. The drugs virginiamycin 51, quercetin, 2-benzyl acetate, D-camphor, and G418, were bought from Sigma-Aldrich (St. Louis, MO). Doxycycline, p-cumate (p-isopropylbenzoate), and fisetin were purchased from Clontech laboratories (Mountain View, CA), System Biosciences (Mountain View, CA), and Fisher Scientific (Pittsburgh, PA), respectively.

*Escherichia coli* cells were grown in Luria Broth (LB) medium. Carbenicillin (Sigma-Aldrich), kanamycin (Sigma-Aldrich), chloramphenicol (Sigma-Aldrich), or zeocin (Life Technologies, Carlsbad, CA) were used to select bacterial strains that had drug-resistant genes at final concentrations of 75 μg/ml, 50 μg/ml, 20 μg/ml, and 25 μg/ml respectively. Agar was added to 2% for petri plates.

Plasmids

The TOP10 strain of *E. coli* ($F^-$ mcAΔ(mrr-hsdRMS-mcrBC) Φ80lacZΔM15 ΔlacX74 recA1 araD139 Δ(araleu) 7697 galUgalKrpsL (StrR) endA1 nupG) was used for the construction and amplification of plasmids. In this study, plasmids were constructed with previously described methods (Ikushima et al., 2015 G3 (Bethesda) 5, 1983-1990; Agmon et al., 2015 ACS Synth. Biol., 4: 853-859; Mitchell et al., 2013 ACS Synth. Biol., 2: 473-477). The yeast GoldenGate (yGG) assembly method enabled "one-pot" plasmid construction because restriction enzymes and DNA ligase could be combined in a single reaction. The Type IIS restriction enzymes BsaI and BsmBI, were used to yield nonpalindromic sticky ends that ligate with one another in a predetermined order and directionality. The standard overhangs flanked by outward facing BsaI sites of the rfp gene were CAGT or TTTT in acceptor vectors unless otherwise described (Agmon et al., 2015 ACS Synth. Biol., 4: 853-859).

Plasmids used in the study are shown in Table 1. In addition to yGG plasmids of pSIB055, pSIB604, pLM270, and pSIB233 (Ikushima et al., 2015 G3 (Bethesda) 5, 1983-1990; Agmon et al., 2015 ACS Synth. Biol., 4: 853-859), three yGG acceptor vectors were newly constructed as follows. Vectors pSIB230 and pSIB270 are convertible plasmids that can be used as either a centromeric plasmid or an integrative plasmid directed into yeast chromosomes VI or XI. Each has a yeast selection marker of KlURA3 and LEU2, respectively. Plasmid pSIB024 is a centromeric acceptor vector that confers phenotypes of uracil prototrophy (URA3) and resistance to G418. In the yGG assembly, the plasmids above were used with the following yGG components: two promoters, TDH1pr and CMVpr from human cytomegalovirus; three coding sequences (CDS), gfp, ADE2, and the rfp gene that turned the host *E. coli* cells bright red; two terminators, STR1tr and GSH1tr. All these parts were described previously (Ikushima et al., 2015 G3 (Bethesda) 5, 1983-1990).

TABLE 1

Plasmids used in this study

| Plasmid | Origin | Description |
|---|---|---|
| pSIB055[a)] | AV | cam$^r$, HIS3, integrative (targetChVI), rfp |
| pSIB604[a)] | AV | amp$^r$, LEU2, integrative (YKL162c), rfp |
| pLM270[a)] | AV | amp$^r$, 2μ, LEU2, rfp |
| pSIB233[b)] | AV | amp$^r$, KlURA3, centromeric/integrative (YKL162c), rfp |
| pSIB230 | AV | amp$^r$, Sphis5, centromeric/integrative (targetChVI), rfp |
| pSIB270 | AV | amp$^r$, LEU2, integrative (YKL162c), rfp |
| pSIB024 | AV | amp$^r$, kanMX/URA3, centromeric, rfp |
| pSIB918 | pSIB604 | amp$^r$, LEU2, integrative (YKL162c), phlPr (=ADH1tr-phlF operator-CYC1pr)-rfp (BsmBI, overhang of AATG/TGAG)-GSH1tr, CMVpr-phlTA (=phlF-VP16)-STR1tr |
| pSIB927 | pSIB918 | amp$^r$, LEU2, integrative (YKL162c), phlPr (=ADH1tr-phlF operator-CYC1pr)-gfp-GSH1tr, CMVpr-phlTA (=phlF-VP16)-STR1tr |
| pSIB883 | pSIB230 | amp$^r$, Sphis5, centromeric/integrative (targetChVI), phlPr (=ADH1tr-phlF operator-CYC1pr)-ADE2-GSH1tr |
| pSIB337 | pSIB233 | amp$^r$, KlURA3, centromeric/integrative (YKL162c), CMVpr-phlTA (=phlF-VP16)-STR1tr |
| pSIB833 | pSIB230 | amp$^r$, Sphis5, centromeric/integrative (targetChVI), ADHphO1 (=ADH1pr-phlF operator single)-ADE2-GSH1tr |
| pSIB924 | pSIB230 | amp$^r$, Sphis5, centromeric/integrative (targetChVI), ADHphO2 (=ADH1pr-phlF operator double)-ADE2-GSH1tr |
| pSIB921 | pSIB270 | amp$^r$, LEU2, integrative (YKL162c), TDH1pr-NLS-phlF-STR1tr |
| pSIB726 | pLM270 | amp$^r$, LEU2, 2μ, TDH1pr-NLS-phlF-STR1tr |
| pSIB170 | pSIB055 | cam$^r$, HIS3, integrative (targetChVI), varPr (=ADH1tr-varR operator-CYC1pr)-gfp-GSH1tr |
| pSIB145 | pSIB024 | amp$^r$, kanMX/URA3, centromeric, CMVpr-varTA (=varR-VP16)-STR1tr |
| pSIB084 | pSIB055 | cam$^r$, HIS3, integrative (targetChVI), lmrPr (=ADH1tr-lmrA/yxaF operator-CYC1pr)-gfp-GSH1tr |
| pSIB133 | pSIB024 | amp$^r$, kanMX/URA3, centromeric, CMVpr-lmrTAv1 (=lmrA-VP16)-STR1tr |
| pSIB220 | pSIB024 | amp$^r$, kanMX/URA3, centromeric, CMVpr-lmrTAv2 (=NLS-lmrA-VP16)-STR1tr |
| pSIB166 | pSIB055 | cam$^r$, HIS3, integrative (targetChVI), icaPr (=ADH1tr-icaR operator-CYC1pr)-gfp-GSH1tr |
| pSIB222 | pSIB024 | amp$^r$, kanMX/URA3, centromeric, CMVpr-icaTA (=icaR-VP16)-STR1tr |
| pSIB454 | pSIB230 | amp$^r$, Sphis5, centromeric/integrative (targetChVI), ethPr (=ADH1tr-ethR operator-CYC1pr)-gfp-GSH1tr |
| pSIB750 | pSIB233 | amp$^r$, KlURA3, centromeric/integrative (YKL162c), CMVpr-ethTA(=NLS-ethR-VP16)-STR1tr |
| pSIB531 | pSIB233 | amp$^r$, KlURA3, centromeric/integrative (YKL162c), CMVpr-yxaTA (=NLS-yxaF-VP16-NLS)-STR1tr |
| pSIB431 | pSIB230 | amp$^r$, Sphis5, centromeric/integrative (targetChVI), dhaPr (=ADH1tr-dhaR operator-CYC1pr)-gfp-GSH1tr |
| pSIB503 | pSIB233 | amp$^r$, KlURA3, centromeric/integrative (YKL162c), CMVpr-dhaTA(=dhaR-VP16-NLS)-STR1tr |

TABLE 1-continued

| Plasmids used in this study | | |
|---|---|---|
| Plasmid | Origin | Description |
| pSIB803 | pSIB230 | amp$^r$, Sphis5, centromeric/integrative (targetChVI), cymPr (=ADH1tr-cymR operator-CYC1pr)-gfp-GSH1tr |
| pSIB470 | pSIB233 | amp$^r$, KlURA3, centromeric/integrative (YKL162c), CMVpr-cymTA(=NLS-cymR-VP16)-STR1tr |

Notes.
Asterisks show sources: [a)]Agmon et al. (2015); [b)] Ikushima et al. (2015). The other plasmids were constructed in this study (see Materials and methods).
Abbreviations:
AV, acceptor vector;
targetChVI: an intergenic region between GAT1/YFL021w and PAU5/YFL020c;
cam$^r$, chloramphenicol resistant gene;
amp$^r$, ampicillin resistant gene;
KlURA3, Kluyveromyces lactis URA3;
Sphis5, *Schizosaccharomyces pombe* his5.

In particular, a specialized acceptor vector pSIB918, which is "yGG-ready" for putting any gene under the control of the DAPG-Off system in an integrated state at YKL162c gene with a single transformation, was constructed as follows. First, the rfp gene in the acceptor vector pSIB604 was replaced with the CMVpr, phlTA CDS, and the STR1tr. The resultant plasmid harbored a pair of BsmBI sites at the 5'-side of the CMVpr part to accommodate a second transcription unit cassette, and three DNA fragments, phlPr, rfp, and GSH1tr were ligated in the BsmBI gap to generate pSIB918. Plasmid pSIB927 was built by replacing rfp of pSIB918 with the gfp gene.

A plasmid, pSIB883 was constructed by inserting phlPr, ADE2, and GSH1tr in yGG acceptor vector pSIB230. In order to build pSIB337, the rfp gene in pSIB233 was replaced with the CMVpr, CDS for phlTA, and the STR1tr.

The three parts, a promoter ADHphlO$_1$, ADE2, and GSH1tr, were cloned as a transcription unit into pSIB230 to yield pSIB833. A related plasmid, pSIB924, contains the promoter ADHphlO$_2$ instead of ADHphlO$_1$ of pSIB833. The 2μ plasmid pSIB628 was used as an acceptor vector to build pSIB726, harboring a transcriptional unit consisting of TDH1pr, a nuclear localization signal (NLS)-fused PhlF and the STR1tr.

Two other sets of plasmids were constructed. One set has a promoter corresponding to each of the tetR-homologs' operator in a minimal promoter fragment fused to gfp as a reporter. The other is a group of vectors that constitutively express a transactivator consisting of the TetR homolog and VP16. The DNA sequences for TetR homologs were codon-optimized using GeneDesign (Richardson et al., 2006 Genome Res., 16, 550-556) for expression in yeast.

Yeast Strains

Yeast strains are listed in Table 2. Strain BY-ADE was constructed by transforming ade2-deficient BY11204 with a PCR fragment containing the wild-type ADE2 amplified with primers SI-589 (5'-TCCACAATCAAT-TGCGAGAAGC (SEQ ID NO: 1)) and SI-590 (5'-CAT-TTGTTGGAGGAAAGTTGTCC (SEQ ID NO: 2)) using BY4741 genomic DNA as template, followed by selection of an adenine prototrophic phenotype. The other transformations to integrate the expression cassettes were conducted using DNA fragments prepared from the aforementioned pSIB-series of plasmids, previously digested with NotI.

TABLE 2

| Yeast strains used in this study | | |
|---|---|---|
| Strain | Another name | Genotype |
| BY4741[a)] | | MATa his3Δ1 leu2Δ0 met15Δ0 ura3Δ0 |
| DapG-TA | SIY1001 | BY4741 ykl162c::pSIB927 (LEU2, phlPr-gfp, phlTA) |
| BY11204[a)] | | MATa leu2Δ1 his3Δ200 lys2Δ0 ura3-167 met15Δ0 ade2Δ::hisG |
| BY-ADE | SIY0979 | BY11204 ade2Δ::hisG::ADE2 |
| phlA-TA | SIY0987 | BY11204 targetChVI::pSIB883 (Sphis5, phlPr-ADE2)ykl162c::pSIB337 (KlURA3, phlTA) |
| phlA-EmV | SIY0990 | BY11204 targetChVI::pSIB883 (Sphis5, phlPr-ADE2)ykl162c::pSIB233 (KlURA3) |
| varG-TA | SIY0155 | BY4741 targetChVI::pSIB170 (HIS3, varPr-gfp) pSIB145 (kanMX/URA3, CEN, varTA) |
| lmr/yxaG-lmrTAv1 | SIY0083 | BY4741 targetChVI::pSIB084 (HIS3, lmr/yxaPr-gfp) pSIB133 (kanMX/URA3, CEN, lmrTAv1) |
| lmr/yxaG-lmrTAv2 | SIY0256 | BY4741 targetChVI::pSIB084 (HIS3, lmr/yxaPr-gfp) pSIB220 (kanMX/URA3, CEN, lmrTAv2) |
| icaG-TA | SIY0261 | BY4741 targetChVI::pSIB166 (HIS3, icaPr-gfp) pSIB222 (kanMX/URA3, CEN, icaTA) |
| ethG-TA | SIY0743 | BY4741 targetChVI::pSIB454 (Sphis5, ethPr-gfp) ykl162c::pSIB750 (KlURA3, ethTA) |
| lmr/yxaG-yxaTA | SIY0050 | BY4741 targetChVI::pSIB084 (HIS3, lmr/yxaPr-gfp) ykl162c::pSIB531(KlURA3+, yxaTA) |
| dhaG-TA | SIY0525 | BY4741 targetChVI::pSIB431 (Sphis5, dhaPr-gfp) ykl162c::pSIB503 (KlURA3, dhaTA) |
| cymG-TA | SIY0809 | BY4741 targetChVI::pSIB803 (Sphis5, cymPr-gfp) ykl162c::pSIB470 (KlURA3, cymTA) |
| BY4742[a)] | | MATa his3Δ1 leu2Δ0 lys2Δ0 ura3Δ0 |
| TetOffG[b)] | SIY0555 | BY4742 targetChVI::pSIB527 (Sphis5, tetPr-gfp, tTA) |
| camG-TA[b)] | SIY0733 | BY4741 targetChVI::pSIB426 (Sphis5, camPr-gfp)ykl162c::pSIB619 (KlURA3, camTA) |
| AphO1-2μPhlF | SIY1018 | BY11204 targetChVI::pSIB833 (Sphis5, ADHphO1-ADE2) pSIB726 (2μ, LEU2, phlF) |
| AphO1-2μEmv | SIY1016 | BY11204 targetChVI::pSIB833 (Sphis5, ADHphO1-ADE2) pLM270 (2μ, LEU2) |
| AphO2-2μPhlF | SIY1026 | BY11204 targetChVI::pSIB924 (Sphis5, ADHphO2-ADE2) pSIB726 (2μ, LEU2, phlF) |
| AphO2-2μEmv | SIY1024 | BY11204 targetChVI::pSIB924 (Sphis5, ADHphO2-ADE2) pLM270 (2μ, LEU2) |

Notes.
Footnotes show sources: [a)]Agmon et al. (2015); [b)]Ikushima et al. (2015). The other strains were constructed in this study.

Flow Cytometry

Cellular fluorescence from GFP was determined by flow-cytometric analysis with a previously described method (Ikushima et al., 2015 G3 (Bethesda) 5, 1983-1990).

Example 2: Construction of a PhlF-Based Transcriptional Regulator and a phlF Operator-Embedded Promoter for the DAPG-Off System One of the TetR homologs, a PhlF-based transcriptional activator, named phlTA, was constructed by fusing *Pseudomonas* PhlF (GenBank AAF20928.1) to three tandem repeats of a VP16 transcriptional activation domain derived from herpes simplex virus Type 1 (Baron et al., 1997 Nucleic Acids Res., 25: 2723-2729). Here, the CMVpr from human cytomegalovirus was used to drive the appropriate level of phlTA expression.

The promoter used for phlF-dependent expression of a reporter gene was built by embedding seven repeats of the phlF operator sequence (phlO) between the alcohol dehydrogenase ADH1 terminator and a CYC1 (cytochrome c) promoter from which the endogenous UAS (upstream activating sequence) had been removed. The resulting promoter was named phlPr, the architecture of which was analogous to a promoter used in yeast Tet- and Camphor-Off systems (Gari et al., 1997 Yeast, 13: 837-848; Ikushima et al., 2015 G3 (Bethesda) 5, 1983-1990. The unit of the phlF operator used was 5'-TATGTATGATACGAAACGTACCGTATCGTTAAGGTAGCGT (SEQ ID NO: 3; Abbas et al., 2002 J Bacteriol., 184: 3008-3016).

As described herein, the PhlF-derived transcriptional activator, phlTA, binds phlPr to activate transcription of a reporter gene only in the absence of DAPG, the ligand of PhlF, and DAPG ligand binding is predicted to eliminate reporter expression in the presence of DAPG (FIG. 1A).

Example 3: Performance of the DAPG-Off Switch with a GFP Reporter

The performance of the DAPG-Off system was examined using GFP as a reporter. A yeast transformant, DapG-TA (SIY1001), which had phlTA and the phlPr-gfp reporter, was constructed by integrating plasmid pSIB918 in BY4741 (Table 1 and Table 2). The DapG-TA strain showed significant expression of GFP in the absence of DAPG, unlike control strain BY4741 (FIG. 1B). In addition, the GFP fluorescence of the DapG-TA was higher than that of the BY4741 control strain (background) in the presence of 12-μM DAPG, but decreased to the same level as BY4741 at 48-μM DAPG (FIG. 1B-FIG. 1D). These data indicated that the expression of the reporter GFP was regulated in a DAPG-dependent manner, consistent with predictions. Furthermore, the DapG-TA strain was then used to evaluate the kinetics of the DAPG-Off switch. The intensity of GFP showed an increase over a 19-h period in the absence of DAPG, whereas the fluorescence reduced to background levels over 14-h of culture in the presence of 48 μM DAPG (FIG. 1E). This duration of GFP expression is consistent with a half-life of GFP protein in yeast (around 7 h) and suggests transcriptional shutoff is rapid. Moreover, in terms of overall promoter strength, the GFP fluorescence of DapG-TA at 19 h in SC is approximately 13% of the intensity a TDH1pr-gfp and 8-fold higher than KEX2pr-gfp. Thus the DAPG-Off switch should be useful to regulate gene expression for practical, middle-strength expression.

Figure 2:
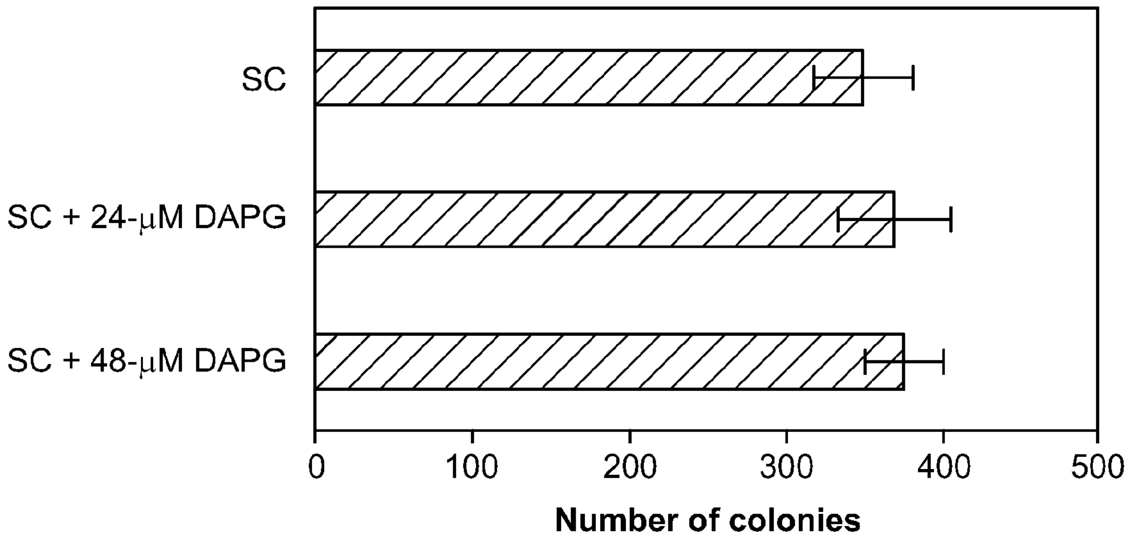
FIG. 2 is a bar graph showing the effects of DAPG on plating efficiency of BY4741. Yeast strain BY4741 overnight culture in SC medium was diluted 25,000-fold, and 100 μl was spread on SC, and SC containing 24-μM or 48 μM of DAPG. The number of colonies formed was counted after 2 days. The values were means and standard deviations calculated from three experiments.
Figure 3:
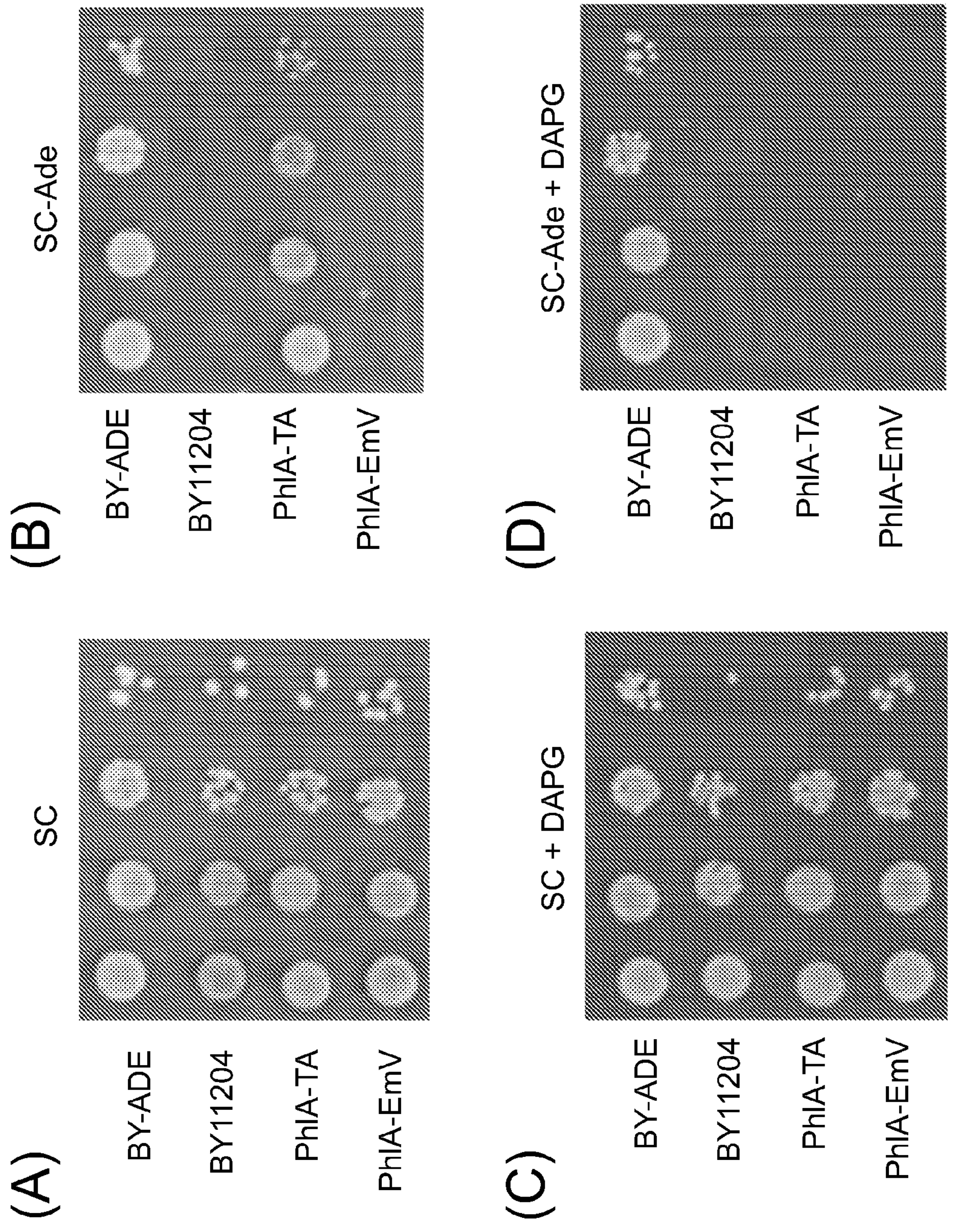
FIG. 3A-FIG. 3D is a series of photographs showing the evaluation of the DAPG-Off system using the ADE2 gene (CDS) as a reporter. Cells were cultured for 2 days at 30° C. in SC (FIG. 3A), SC-Ade (FIG. 3B), SC with 24 μM of DAPG (FIG. 3C), and SC-Ade with 24-DAPG (FIG. 3D). Cells were diluted 10-fold stepwise across each row.

With regards to effects of DAPG on growth, the results presented herein showed that there was little difference in the number of colonies formed in three media types: (a) SC with 24-μM (5-μg/ml) DAPG; (b) SC with 48-μM (10-μg/ml) DAPG; (c) SC without DAPG (FIG. 2). However, previous work suggests that 10-μg/ml DAPG did not inhibit growth of BY4741 (Kwak et al., 2011 Appl. Environ. Microbiol., 77: 1770-1776), whereas cells of this background did show sensitivity to higher concentrations (Troppens et al., 2013 FEMS Yeast Res., 13: 322-334).

Example 4: DAPG-Off System with an ADE2 Reporter

A second reporter gene was used to further assess the performance of the DAPG-Off switch. Here, it was examined whether the ADE2 gene under the control of phlPr complements the adenine-auxotrophy of strain BY11204 in a DAPG-dependent manner (FIG. 3A-FIG. 3D). The BY11204-based yeast transformant phlA-EmV (phlA Empty vector), which had the phlPr-ADE2 reporter gene but not phlTA, showed solid growth on SC medium, but failed to grow in SC-Ade medium, irrespective of DAPG concentration. On the other hand, the phlA-TA strain, harboring both phlPr-ADE2 and phlTA showed proliferation in a DAPG-free SC-Ade medium. In contrast, the strain did not grow on SC-Ade medium containing 24 μM DAPG. Similarly to the GFP reporter (FIG. 1B-FIG. 1E), the DAPG-Off switch enabled very tight regulation of the reporter gene phlPr-ADE2. Moreover, no revertants appeared on SC-Ade agar plates on plating of $2.3\times10^5$ cells, consistent with a genetically stable DAPG-Off system.

Example 5: Construction of Off-Switches Using Other TetR Homologs

This study assessed other TetR homologs' ligands and operators previously reported (Table 3): varR (Namwat et al., 2001 J. Bacteriol., 183: 2025-2031), lmrA (Yoshida et al., 2004 J. Bacteriol., 186: 5640-5648; Hirooka et al., 2007 J. Bacteriol., 189: 5170-5182), icaR (Jeng et al., Nucleic Acids Res., 36: 1567-1577), yxaF (Yoshida et al., 2004 J. Bacteriol., 186: 5640-5648; Hirooka et al., 2007 J. Bacteriol., 189: 5170-5182), dhaR (Poelarends et al., 2000 J. Bacteriol., 182: 2191-2199), ethR (Weber et al., 2008 Proceedings of the National Academy of Sciences U.S.A., 105: 9994-9998), and cymR (Eaton, R. W. 1997 J Bacteriol, 179: 3171-3180; Mullick et al., 2006 BMC Biotechnol., 6: 43; Kaczmarczyk et al., 2013 Appl. Environ. Microbiol., 79: 6795-6802). The scheme to evaluate the switch candidates was similar to the DAPG-Off switch. A transcriptional activation domain of VP16 was added to the TetR homologs (transactivator), and operator sequences of them were interposed between the ADH1 terminator and UAS-less CYC1 promoter, followed by the gfp reporter. First, it was observed that all strains which had only the gfp reporter did not express GFP; the strains were then transformed with plasmids to express the corresponding transactivators and expression was evaluated.

TABLE 3

Yeast off-switch candidates evaluated in this study

| Switch candidate (Strain) | TetR homolog (Accession) | NLS | Operator | Species | Drug (Concentration) | Expression of GFP w/o drug | Expression of GFP with drug |
|---|---|---|---|---|---|---|---|
| Var-Off (varG-TA) | VarR (BAB32408) | w/o | varR operator[a)] | *Streptomyces virginae* | Virginiamycin S1 (2 mM) | On | On |
| Lmr-Offv1 (lmr/yxaG-lmrTAv1) | LmrA (NP_388150) | w/o | lmrA/yxaF operator[b)] | *Bacillus subtilis* | Quercetin, Fisetin, Coumesterol | Off | ND |
| Lmr-Offv2 (lmr/yxaG-lmrTAv2) | LmrA (NP_388150) | N-end | lmrA/yxaF operator[b)] | *Bacillus subtilis* | Quercetin (0.13 μM), Fisetin (0.19 μM), Coumesterol (0.22 μM) | On | On |
| lcaR-Off (icaG-TA) | IcaR (AAN17770.1) | N-end | icaR operator[c)] | *Staphylococcus epidermidis* | Gentamicin (10 mM) | On | On |
| Eth-Off (ethG-TA) | EthR (NP_218372) | N-end | EthR operator[d)] | *Mycobacterium tuberculosis* | 2-Benzyl acetate (0.01%) | On | On |
| Yxa-Off (lmr/yxaG-yxaTA) | YxaF (BAA21585) | N, C-ends | lmrA/yxaF operator[b)] | *Bacillus subtilis* | Quercetin, Fisetin, Coumesterol) | Off | ND |
| Dha-Off (dhaG-TA) | DhaR (CAB65288) | N-end | dhaR operator[e)] | *Mycobacterium* sp. GP1 | 1-Chlorobutane | Off | ND |
| Cumate-Off (cymG-TA) | CymR (AAB62296) | N-end | cymR operator[f)] | *Pseudomonas putida* | p-Cumate (150 μM) | On | Off |

Notes.
[a)] TGTCACTTGTACATCGTATAACTCTCATATACGTTGTAGAACAGTTC (SEQ ID NO: 4) (4 repeats)
[b)] CTTTCTCCTACAATTATATAGAACGGTCTAGACAAATGAATGATAATATATAGACTGGTCTAAATTGGAGGAAGCGATA (SEQ ID NO: 5)(3 repeats)
[c)] ACAACCTAACTAACGAAAGGTAGGTGAA (SEQ ID NO: 6) (6 repeats)
[d)] GTGTCGATAGTGTCGACATCTCGTTGACGGCCTCGACATTACGTTGATAGCGTGG (SEQ ID NO: 7) (5 repeats)
[e)] AAGATGACCGGTCACCTT (7 repeats)
[f)] AAGAAAGAAACAAACCAACCTGTCTGTATTATCTC (SEQ ID NO: 8)(6 repeats)
Abbreviations: ND, Not determined.

*Streptomyces virginiae* antibiotic resistance regulator VarR tagged with VP16 induced strong GFP expression both in the absence and presence of the ligand virginiamycin S. This result suggested the hybrid transactivator is active, but virginiamycin may not be stably taken up in yeast cells. On the other hand, expressing a transactivator based on LmrA and VP16 gave rise to no gfp activity in the presence or absence of ligand. Since the fusion protein must enter the nucleus for expression in yeast, a nuclear localization signal (NLS) from SV40 (Kalderon et al., 1984 Cell, 39: 499-509) was added to LmrTA, resulting in strong expression of GFP; however, as in the case of VarR-TA, it was not ligand (quercetin)-responsive. Differently from TetR and PhlF in the Tet- and DAPG-Off systems, these results show that some TetR homologs require an NLS in order to activate transcription while others do not. The TetR homologs IcaR and EthR also showed solid ligand-independent GFP fluorescence with gentamicin and 2-benzyl acetate respectively. EthR was previously reported as a useful switch in mammalian cells (Weber et al., 2008 Proceedings of the National Academy of Sciences U.S.A., 105: 9994-9998), but tight regulation of the switch could not be achieved in yeast. The reason behind residual gfp expression in the presence of the ligands remains unclear, but the amount of ligand able to penetrate yeast cell envelopes may not be sufficient to thoroughly prevent transactivator from binding to the operators. Potentially, the use of pdr5 mutants or other drug-sensitized strains might confer responsiveness to such switches. By contrast, YxaF and DhaR did not confer detectable GFP expression even in the absence of their ligands, even though a NLS was appended. Possible reasons are that either amount of the transactivator expression, or alternatively, the affinity between the transactivators and the operator sequences chosen might be insufficient to induce reporter expression. Finally, CymR, a repressor involved in the p-cymene catabolic pathway in *Pseudomonas putida* did result in the expected expression profile of the relevant GFP reporter with p-cumate. Thus, one additional off-switch was obtained for yeast; the strain with the appropriate reporter and activator is called CymG-TA.

Example 6: Orthogonality of the Yeast Off-Switches

Figure 4A:
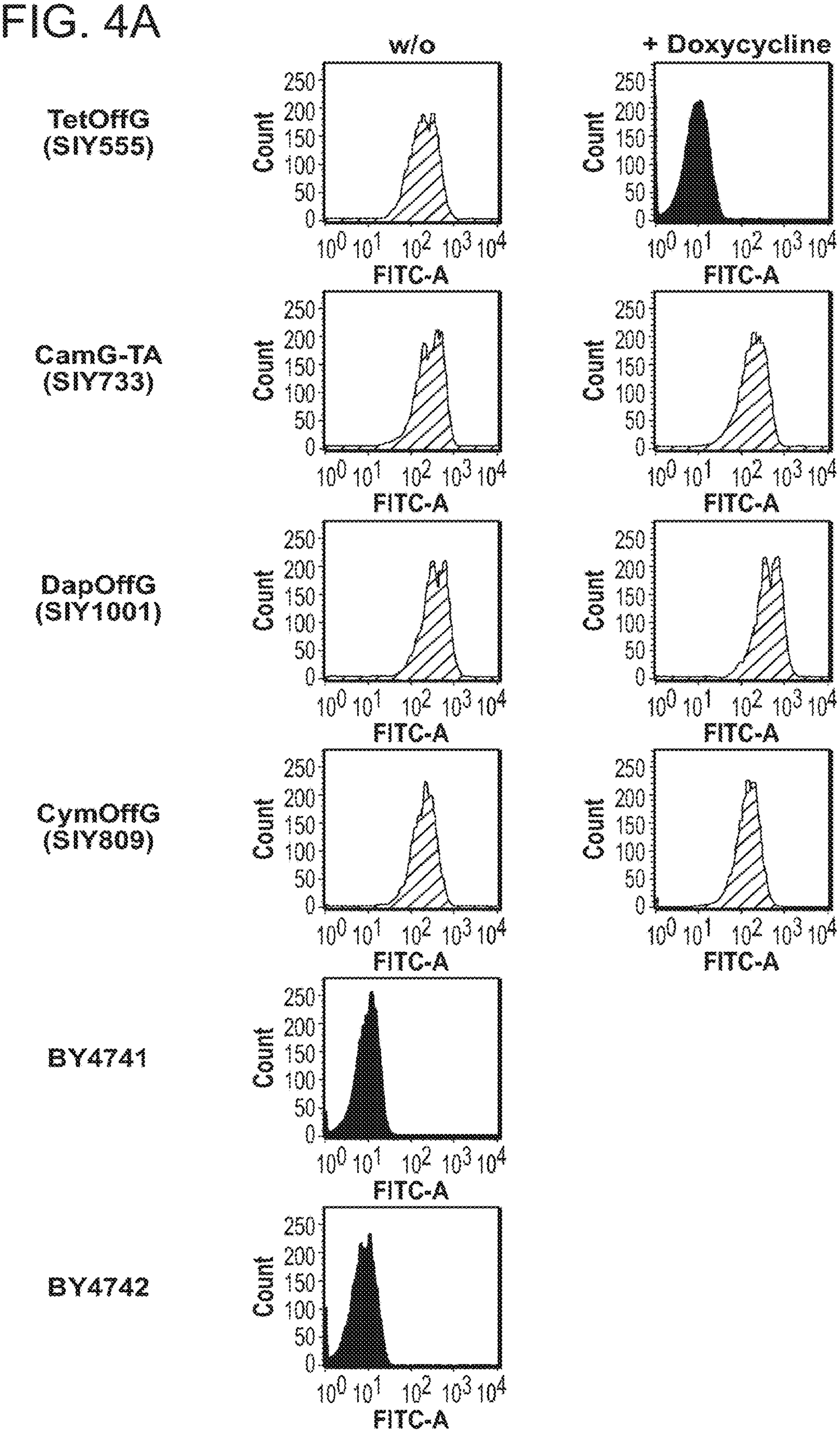
FIG. 4 is a series of graphs showing evaluation of four orthogonal systems (the Tet-Off®, Camphor-Off, DAPG-Off, and Cumate-Off switches). The gfp gene was used as a reporter, and fluorescence was evaluated in SC medium, SC with 25-μM doxycycline, SC with 25-μM D-camphor, SC with 48-μM DAPG, and SC with 150-μM p-cumate across each column.
Figure 4B:
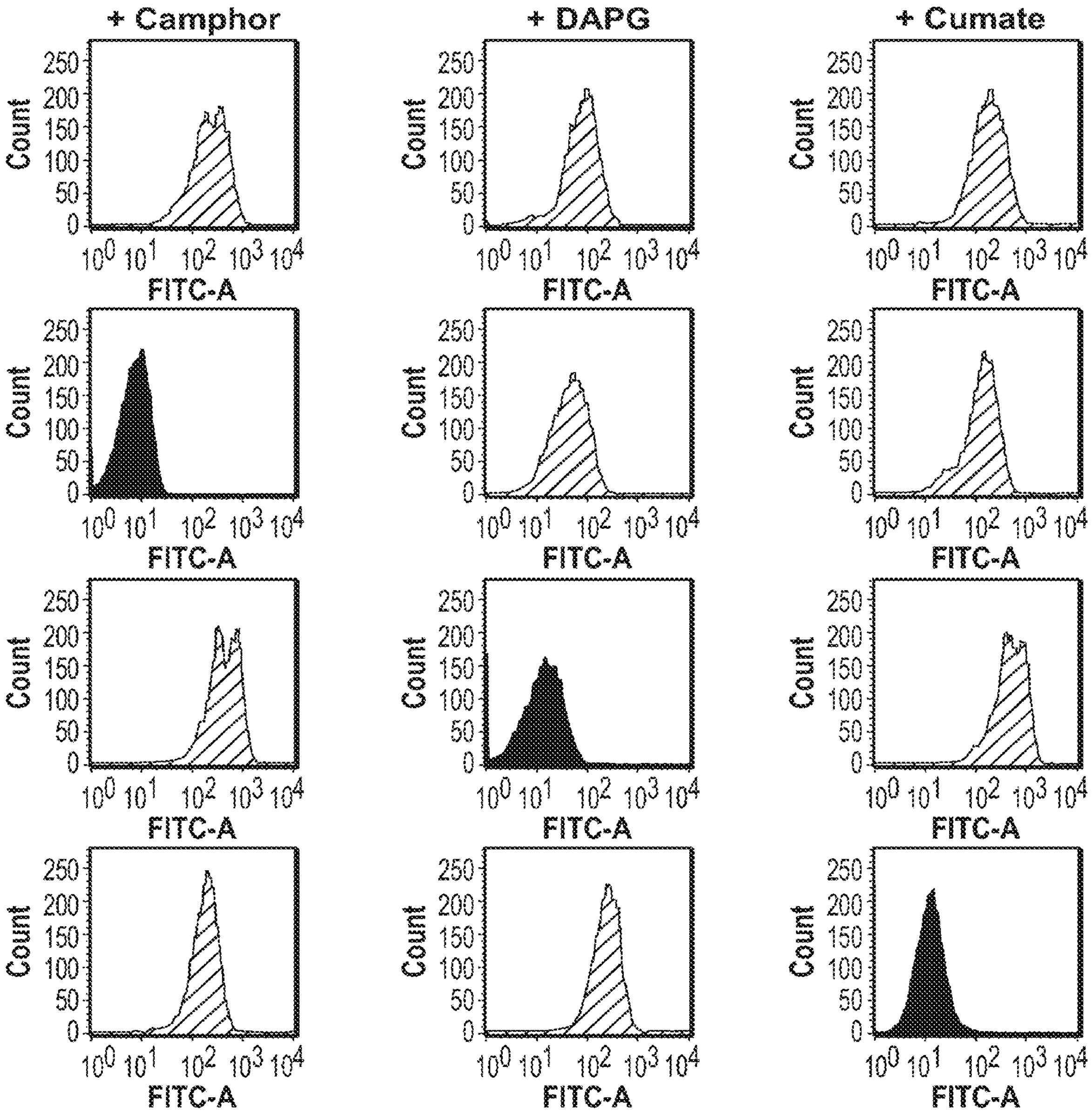

A series of switches anticipated for use together must be evaluated for orthogonality to maximize their utility. Thereby, four switches of the Tet-Off®, Camphor-Off, DAPG-Off, and Cumate-Off systems were evaluated. When four strains that contained the switches independently were cultured in the absence and presence of the four ligands (doxycycline, camphor, DAPG, cumate), the intensity of reporter GFP fluorescence decreased to the background level only in the presence of the appropriate ligands, whereas in the presence of the inappropriate ligands, a strong GFP signal was observed, similar to that observed in the absence of any ligands (FIG. 4). An exception to this trend was that cells with the Tet or Cam system showed lowered GFP fluorescence in the DAPG medium. Thus, DAPG may have slightly reduced orthogonality, but the GFP signal can also certainly be affected by other factors, such as growth phase (FIG. 1E). In short, the results suggest that the four switches are useful to construct complex biological circuits in which multiple reporter genes are regulated separately in a single strain. Indeed, this is the case for the Tet and Cam systems independently regulated in the same strain (Ikushima et al., 2015 G3 (Bethesda) 5, 1983-1990).

Example 7: Construction of Two Components for the DAPG-on System

Figure 5:
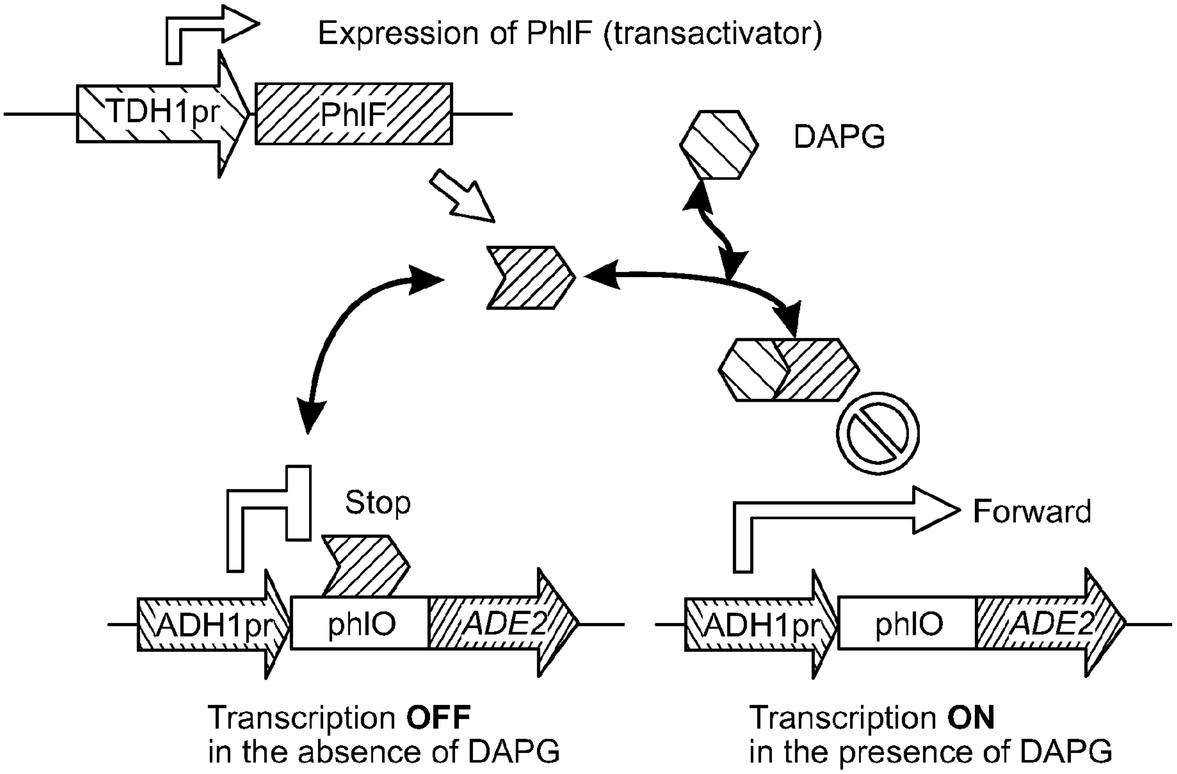
FIG. 5 is a schematic diagram of the DAPG-On switch using the ADE2 gene as a reporter (Abbreviation: phlO, phlF operator sequence).
Figure 6:
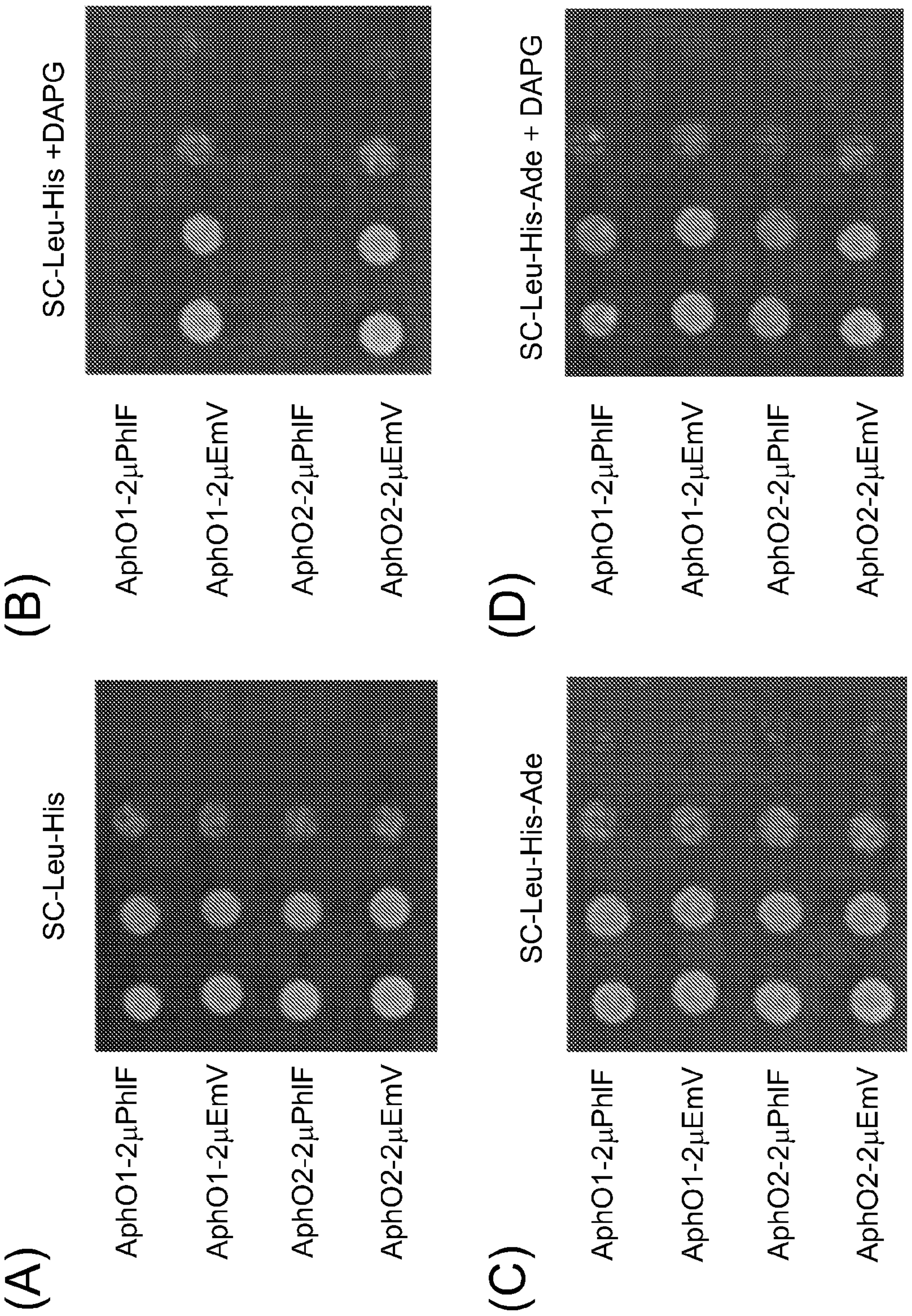
FIG. 6A-FIG. 6D is a series of photographs showing spot analysis using an ADE2 reporter under control of the DAPG-On system. Cells were cultured for 1 day at 30° C. in SC-Leu-His (FIG. 6A), SC-Leu-His-Ade (FIG. 6B), SC-Leu-His with 24-μM DAPG (FIG. 6C), and SC-Leu-His-Ade with 24-μM DAPG (FIG. 6D). The cells were diluted 10-fold stepwise across each row.

Next, On-switches that make it possible to induce expression of a gene of interest by ligand treatment were developed. In particular, a DAPG-On system based on the native transcriptional regulator and a phlO-containing promoter was developed. Here, a single and double repeat of phlO sequences were embedded downstream of the ADH1 promoter (ADH1pr) to build $ADHphlO_1$ and $ADHphlO_2$, leading to constitutive reporter expression in the absence of the transcriptional regulator. The two promoters were analogous in design to the ADHi promoter, which carries a single copy of the lac operator downstream of the ADH1pr (Grilly et al., 2007 Mol. Syst. Biol., 3: 127). Next, a transcriptional regulator consisting of NLS and PhlF was constructed. As shown in FIG. 5, this binds to the ADH1phlO promoter and sterically blocks transcription. The reporter gene expresses only in the presence of DAPG and the NLS-PhlF protein (FIG. 5).

Example 8: DAPG-on System with an ADE2 Reporter

The performance of the DAPG-On system was assessed using ADE2 as a reporter in the ade2Δ BY11204 strain. When PhlF was not expressed in a strain that had the ADHphlOx-ADE2 cassette, the strain, named AphOx-2μEmV, grew in adenine-deficient medium irrespective of DAPG addition as well as in adenine-containing medium (FIG. 6A-FIG. 6D). On the other hand, strain AphOx-2μPhlF, which carried multiple copies of PhlF in addition to the ADHphlOx-ADE2 cassette, hardly grew at all on DAPG-free SC-Ade medium, consistent with binding of PhlF to phlO (phlF operator sequence) preventing expression of the ADHphlOx-driven ADE2 gene. However, both strains AphOx-2μPhlF showed vigorous growth on a SC-Ade medium in the presence of 5 μM DAPG. These results suggest that DAPG released PhlF from the phlO region and led to expression of ADE2. With regard to the genetic stability of the DAPG-On system, the reversion frequencies to adenine-prototrophic ($Ade^+$) clones were $9.4\times10^{-6}$ and $1.2\times10^{-6}$ for strains AphO1-2μPhlF and AphO2-2μPhlF respectively. The stability is enhanced further by increasing the copy number of phlO downstream of ADH1pr, since there was an 8-fold difference in reversion frequency between the two strains. These results suggest that the DAPG-On system is useful for regulating expression of a gene of interest with the opposite logic of the DAPG-Off system.

Perspectives

Expression switches that can be regulated with small compounds are widely used in biology-related studies. The Tet-Off and -On systems are among the most popular switches because of their advantages, e.g., tight regulation and ease of handling, but the number of such ligand regulated switches is very limited. Thus, more and better switches would enable more options to control gene expression.

Described herein is the assessment of seven TetR homologs to develop transcription switches in yeast, resulting in switches based on two TetR homologs, PhlF and CymR. They were named DAPG-Off, DAPG-On, and Cumate-Off switches in which DAPG or p-cumate prevented or triggered the expression of a reporter gene such as gfp and ADE2 at a concentration. As described herein, the Cumate-Off switch is further evaluated for reversion and performance with an auxotrophic reporter. However, most importantly, the two switches showed robust orthogonality to other useful switches such as the Tet- and camphor switches. These switches expand the repertoire of regulated gene expression in yeast (Table 4). On the other hand, this study did not yield controllable switches in the case of five other TetR homologs including EthR, which has been shown to work as a switch in mammalian cells. Thus, not all TetR homologs are directly applicable for use as a high performing expression switch in yeast.

TABLE 4

Useful On and Off switch reagents for end users

| Plasmid | yGG-use | Description | Restriction enzyme site (overhang of top/end-sides) |
|---|---|---|---|
| | | <DAPG-Off system> | |
| pSIB918 | AV | $amp^r$, LEU2, integrative (YKL162c), phlPr (=ADH1tr-phlF operator-CYC1pr)-rfp-GSH1tr, CMVpr-phlTA (=phlF-VP16)-STR1tr | BsmBI (AATG/TGAG) |
| pSIB289 | Transactivator | $kan^r$, phlTA (=phlF-VP16) | BsmBI (AATG/TGAG) |
| pSIB153 | Promoter with operator | $kan^r$, phlPr (=ADH1tr-phlF operator-CYC1pr) | BsaI (CAGT/AATG) |
| | | <Tet-Off system> | |
| pSIB498 | AV | $amp^r$, Sphis5, integrative (targetChVI), CMVpr-tTA(=tetR-VP16)-STR1tr, tetPr (=ADH1tr-tetR operator-CYC1pr)-rfp-GSH1tr | BsmBI (AATG/TGAG) |
| pSIB009 | Transactivator | $amp^r$, tTA (=tetR-VP16) | BsaI (AATG/TGAG) |
| pSIB022 | Promoter with operator | $kan^r$, tetOPr (=ADH1tr-tetO operator-CYC1pr) | BsaI (CAGT/AATG) |

TABLE 4-continued

Useful On and Off switch reagents for end users

| Plasmid | yGG-use | Description | Restriction enzyme site (overhang of top/end-sides) |
|---|---|---|---|
| | | <Camphor-Off system> | |
| pSIB859 | AV | amp$^r$, KlURA3, integrative (HO), TDH1pr-camTA (=camR-VP16-NLS)-STR1tr, camPr (=ADH1tr-camR operator-CYC1pr)-rfp-SOL3tr | BsmBI (AATG/TGAG) |
| pSIB477 | Transactivator | kan$^r$, camTA (=camR-VP16-NLS) | BsmBI (AATG/TGAG) |
| pSIB396 | Promoter with operator | kan$^r$, camPr (=ADH1tr-camR operator-CYC1pr) | BsaI (CAGT/AATG) |
| | | <Cumate-Off system> | |
| pSIB665 | Transactivator | kan$^r$, cymTA (=NLS-cymR-VP16) | BsaI (AATG/TGAG) |
| pSIB795 | Promoter with operator | kan$^r$, cymPr (=ADH1tr-cymR operator-CYC1pr) | BsaI (CAGT/AATG) |
| | | <DAPG-On system> | |
| pSIB199 | Transactivator | kan$^r$, NLS-phlF | BsaI (AATG/TGAG) |
| pSIB916 | Promoter with operator | kan$^r$, ADHphO2 (=ADH1pr-phlF operator double) | BsaI (CAGT/AATG) |
| | | <Tet-On system> | |
| pSIB499 | AV | amp$^r$, Sphis5, integrative (targetChVI), CMVpr-rtTA(=mutated tetR-VP16)-STR1tr, tetPr (=ADH1tr-tetR operator-CYC1pr)-rfp-GSH1tr | BsmBI (AATG/TGAG) |
| pSIB010 | Transactivator | amp$^r$, rtTA (=muated tetR-VP16) | BsaI (AATG/TGAG) |
| pSIB022 | See above (Tet-Off) | — | — |
| | | [Common parts for yGG] | |
| pSIB027 | Promoter | kan$^r$, TDH1 promoter (=TDH1pr) | BsaI (CAGT/AATG) |
| pSIB237 | Promoter | kan$^r$, CMV promoter (mutated to be BsmBI-free) (=CMVpr) | BsaI (CAGT/AATG) |
| pSIB031 | Terminator | kan$^r$, GSH1 terminator (=GSH1pr) | BsaI (TGAG/TTTT) |
| pSIB206 | Terminator | kan$^r$, STR1 terminator (mutated to be BsmBI-free) (=STR1tr) | BsaI (TGAG/TTTT) |
| pSIB639 | Terminator | kan$^r$, SOL3 terminator (=SOL3tr) | BsaI (TGAG/TTTT) |

Notes.
Plasmids except for pSIB918 were not listed in Table 1, but details on the plasmids are described in "Supporting information".
Abbreviations:
AV, acceptor vector;
targetChVI: an intergenic region between GAT1/YFL021w and PAU5/YFL020c;
amp$^r$, ampicillin resistant gene;
kanr$^r$, kanamycin resistant gene.

In the development of the DAPG-On switch, it was speculated that a DAPG-On switch could be constructed by mutating phlTA, fusion of PhlF and triple repeats of VP16, because the transactivators of the Tet-On and Cumate-On switches (named rev-tTA) could be isolated from multiple missense mutants of the transactivators used in the Tet-Off and Cumate-Off systems, VP16-tethered TetR or CymR, respectively. In fact, it was confirmed that the Tet-On switch a transactivator based on the 5-amino acid residue TetR variant named rtTA-M2 (Urlinger et al., 2000 Proceedings of the National Academy of Sciences U.S.A., 97: 7963-7968) showed doxycycline-dependent GFP expression in the opposite manner to the Tet-Off system in yeast. However, such a mutant with opposite behavior to the DAPG-Off system was not isolated. In this study, another way to develop the DAPG-On system was developed in which the binding of PhlF to the operator could sterically prevent the transcription of a reporter gene, resulting in relatively tight regulation of the ADE2 reporter (FIG. 6A-FIG. 6D). This strategy is effective for developing additional On-switches in yeast.

As an alternative strategy, other sources are identified for constructing a Compound-On switch. Notably, in natural environments, there is another type of TetR homolog that binds to an operator preferentially in the presence of a specific ligand. As described herein, those proteins are made use of as a kind of "natural" rev-tTA. Many quorum-sensing (QS) molecules that function as transcriptional regulators are known (Safari et al., 2014 Appl. Microbiol. Biotechnol., 98: 3401-3412). Interestingly, the binding of a TetR homolog, such as LuxR and TraR, to an operator sequence is triggered with a QS molecule. Prior to the invention described herein, a functional switch has not been obtained using the QS-related transactivators. However, a QS molecule-On switch is constructed from a number of QS-related TetR homologs. Additional transcriptional switches are developed using TetR homologs as a great tool in biotechnology.

An additional description of plasmids listed in Table 4 is provided below.

DAPG-Off System: pSIB918, pSIB289, and pSIB153

All three plasmids were constructed in this study: pSIB918 was referred to in Table 1. pSIB289 and pSIB153 were used to build pSIB918. The sequences for the DAPG-Off system are provided above.

Tet-Off System: pSIB498, pSIB009, and pSIB022

Plasmids pSIB009 and pSIB022 provided elements of the "transactivator" and "operator-embedded promoter" to construct pSIB498, and all three plasmids were prepared previously but the names were not mentioned as such (Ikushima et al., 2015 G3 (Bethesda), Vol. 5 (10), 1983-1990, incorporated herein by reference). In particular, pSIB498 is the most generally useful yeast GoldenGate-ready acceptor vector carrying the Tet-Off switch. Plasmid pSIB527 shown in the article was constructed by replacing rfp gene of pSIB498 with gfp gene.

An exemplary nucleic acid sequence for tTA (tetR-VP16) in pSIB498 for the Tet-Off system is provided below (1-618, label=TetR; 619-744, VP16; 745-747, Stop codon; SEQ ID NO: 22):

```
atgagtagattggacaagtctaaggttatcaactctgctttggaattgag
aacgaagttggtatcgaaggtttgaccaccagaaagttggctcaaaagtt
gggtgttgaacaaccaaccttgtactggcacgttaagaacaagagagctt
tgaggacgctttggctatcgaaatgttggacagacaccacacccacttct
gtccattggaaggtgaatcttggcaagacttcttgagaaacaacgctaag
tctttcagatgtgctttgctctctcaccgcgacggtgctaaggttcactt
gggaaccagaccaaccgaaaagcaatacgaaaccttggaaaaccaattgg
ctttcttgtgtcaacaaggtttctctttggaaaacgctttgtacgctttg
tctgctgaggtcacttcaccttgggttgtgttttggaagaccaagaacac
caagttgctaaggaagaaagagaaaccccaaccaccgactctatgccacc
attgctcagacaagctatcgaattgttcgaccaccaaggtgctgaaccag
ctttcttgttcggtttggaattgatcatctgtggtttggaaaagcaattg
aagtgtgaatctggtgggccggccgacgctttggacgacttcgacttgga
catgttgccagctgacgctttggacgacttcgacttggacatgttgccag
ctgacgctttggacgacttcgacttggacatgttgccaggttga
```

An exemplary amino acid sequence for tTA (tetR-VP16) in pSIB498 for the Tet-Off system is provided below (SEQ ID NO: 23):

```
MSRLDKSKVINSALELLNEVGIEGLTTRKLAQKLGVEQPTLYWHVKNKRA
LLDALAIEMLDRHHTHFCPLEGESWQDFLRNNAKSFRCALLSHRDGAKVH
LGTRPTEKQYETLENQLAFLCQQGFSLENALYALSAVGHFTLGCVLEDQE
HQVAKEERETPTTDSMPPLLRQAIELFDHQGAEPAFLFGLELIICGLEKQ
LKCESGGPADALDDFDLDMLPADALDDFDLDMLPADALDDFDLDMLPG
```

An exemplary nucleic acid sequence for tetOpr (ADH1tr-tetO operator-CYC1pr) in pSIB498 for the Tet-Off system is provided below (1-203, ADH1 transcriptional terminator; 216-508, tetR operator; 521-667, CYC1 promoter; SEQ ID NO: 24):

```
cacttctaaataagcgaatttcttatgatttatgatttttattattaaat
aagttataaaaaaaataagtgtatacaaattttaaagtgactcttaggtt
ttaaaacgaaaattcttgttcttgagtaactctttcctgtaggtcaggtt
gctttctcaggtatagcatgaggtcgctcttattgaccacacctctaccg
gcaggccggcccgggtcgagtttaccactccctatcagtgatagagaaaa
gtgaaagtcgagtttaccactccctatcagtgatagagaaaagtgaaagt
cgagtttaccactccctatcagtgatagagaaaagtgaaagtcgagttta
ccactccctatcagtgatagagaaaagtgaaagtcgagtttaccactccc
tatcagtgatagagaaaagtgaaagtcgagtttaccactccctatcagtg
atagagaaaagtgaaagtcgagtttaccactccctatcagtgatagagaa
```

-continued

```
aagtgaaacccgggccggcctatggcatgcatgtgctctgtatgtatata
aaactcttgttttcttcttttctctaaatattctttccttatacattagg
tcctttgtagcataaattactatacttctatagacacgcaaacacaaata
cacacactaaattaata
```

Camphor-Off System: pSIB859, pSIB477, and pSIB396

As was the case with the Tet-Off switch plasmids above, pSIB477 and pSIB396 provided elements of "transactivator" and "operator-embedded promoter" parts for pSIB859, and all the three plasmids were prepared previously (Ikushima et al., 2015 G3 (Bethesda), Vol. 5 (10), 1983-1990, incorporated herein by reference). Particularly, pSIB859 is the most generally useful yeast GoldenGate-ready acceptor vector carrying the Camphor-Off switch. Accordingly, this plasmid was used to construct pSIB872 described herein.

An exemplary nucleic acid sequence for camTA (camR-VP16-NLS) in pSIB859 for the Camphor-Off system is provided below (1-558, CamR (*Pseudomonas putida*); 559-684, VP16; 685-708, NLS (SV40); 709-711, Stop codon; SEQ ID NO: 25):

```
atggacatcaagcaatctttgttgcacgctgctatgagattgttgtctgc
taagggtcgcgacggtgctaccatgcgaccaatctgtgctgaagttggtg
ttaccccaccaaccttgtaccaccactacggtgacttgcaaggtttgcac
aaggctgctatcgacgaaacctacagacaagttgctgaagcttaccacgg
tggtaccgaagaaagaggtccattgaagggtatccgcgacggttgggcta
ccttcttgcaattcgcttactctgaaccaaacatgtgtagaatgttggtt
caacacatcatggctggtgaaccaccatctatggttgctgacaccttgag
aggtgttgctgacgacttggctcaattccacgctcaaggtagattgacct
tcccaccaagagaagctgctcaattgttgtggatgggtgctttgggtgct
ttgacctacgctttgtctagagaaggtgctggttacacccaagacttggc
tttgcaaaaggctaagttggacatcaccttggttgctttgttcaacatcg
aagaagaagggccggccgacgctttggacgacttcgacttggacatgttg
cctgcagatgcacttgatgattttgatcttgatatgcttccagcagacgc
attggatgactttgaccttgacatgcttcctggtatgccaaagaagaaga
gaaaggtatga
```

An exemplary amino acid sequence for camTA (camR-VP16-NLS) in pSIB859 for the Camphor-Off system is provided below (SEQ ID NO: 26):

```
MDIKQSLLHAAMRLLSAKGRDGATMRPICAEVGVTPPTLYHHYGDLQGLH
KAAIDETYRQVAEAYHGGTEERGPLKGIRDGWATFLQFAYSEPNMCRMLV
QHIMAGEPPSMVADTLRGVADDLAQFHAQGRLTFPPREAAQLLWMGALGA
LTYALSREGAGYTQDLALQKAKLDITLVALFNIEEEGPADALDDFDLDML
PADALDDFDLDMLPADALDDFDLDMLPGMPKKKRKV
```

An exemplary nucleic acid sequence for camPR (ADH1tr-camR operator-CYC1pr) for the Camphor-Off system is provided below (1-203, ADH1 transcriptional terminator; 208-430, camR operator; 432-574, CYC1 promoter; SEQ ID NO: 27):

```
cacttctaaataagcgaatttcttatgatttatgatttttattattaaat

aagttataaaaaaaataagtgtatacaaattttaaagtgactcttaggtt

ttaaaacgaaaattcttgttcttgagtaactctttcctgtaggtcaggtt

gctttctcaggtatagcatgaggtcgctcttattgaccacacctctaccg

gcaaggtcaggctctatatctgcgatatactgagcatatcccccccaggc

tctatatctgcgatatactgagcatatcccccccaggctctatatctgcg

atatactgagcatatcccccccaggctctatatctgcgatatactgagca

tatcccccccaggctctatatctgcgatatactgagcatatccccccaggc

tctatatctgcgatatactgagcatatcccaatggcatgcatgtgctctg

tatgtatataaaactcttgttttcttcttttctctaaatattctttcctt

atacattaggtcctttgtagcataaattactatacttctatagacacgca

aacacaaatacacacactaaattaata
```

Cumate-Off System: pSIB665 and pSIB795

Plasmids pSIB665 and pSIB795 were constructed herein. They provided the "transactivator" and "operator-embedded promoter" parts for pSIB470 and pSIB803, respectively.

DAPG-on System: pSIB199 and pSIB916

Plasmids pSIB199 and pSIB916 were constructed herein. They provided "transactivator" and "operator-embedded promoter" parts for pSIB470 and pSIB803, respectively.

Tet-on System: pSIB499, pSIB010, and pSIB022

Plasmids pSIB010 and pSIB022 provided "transactivator" and "operator-embedded promoter" parts for pSIB499. Specifically, pSIB499 is the most generally useful yeast GoldenGate-ready acceptor vector specialized for the Tet-On system in which the transactivator is the TetR variant with alteration of 5-amino acids (S12G E19G A56P D148E H179R), known as "rtTA-M2" (Urlinger et al., 2000 *Proc. Natl. Acad. Sci. USA*, Vol. 97 (14), 7963-7968, incorporated herein by reference).

The rtTA acts in the opposite manner against tTA of the Tet-Off system. The present study yielded BY4741-derived transformants with a plasmid that harbored gfp gene in the position of rfp of pSIB499. Only background GFP fluorescence was observed in the absence of doxycycline, while GFP significantly expressed in the presence of more than 10-μM doxycycline.

An exemplary nucleic acid sequence for rtTA (tetR mutant-VP16) in pSIB499 for the Tet-On system is provided below (1-618, mutated TetR; 619-744, VP16; 745-747, Stop codon; SEQ ID NO: 28):

```
atgagtagattggacaagtctaaggttatcaacggtgctttggaattgtt

gaacggtgttggtatcgaaggtttgaccaccagaaagttggctcaaaagt

tgggtgttgaacaaccaaccttgtactggcacgttaagaacaagagagct

ttgttggacgctttgccaatcgaaatgttggacagacaccacacccactt

ctgtccattggaaggtgaatcttggcaagacttcttgagaaacaacgcta

agtctttcagatgtgctttgctctctcaccgcgacggtgctaaggttcac

ttgggaaccagaccaaccgaaaagcaatacgaaaccttggaaaaccaatt

ggctttcttgtgtcaacaaggtttctctttggaaaacgctttgtacgctt

tgtctgctgttggtcacttcaccttgggttgtgttttggaagaacaagaa
```

-continued

```
caccaagttgctaaggaagaaagagaaaccccaaccaccgactctatgcc

accattgctcagacaagctatcgaattgttcgacagacaaggtgctgaac

cagctttcttgttcggtttggaattgatcatctgtggtttggaaaagcaa

ttgaagtgtgaatctggtgggccggccgacgctttggacgacttcgactt

ggacatgttgccagctgacgctttggacgacttcgacttggacatgagcc

agctgacgctttggacgacttcgacttggacatgttgccaggttga
```

An exemplary amino acid sequence for rtTA (tetR-VP16) in pSIB499 for the Tet-On system is provided below (SEQ ID NO: 29):

```
MSRLDKSKVINGALELLNGVGIEGLTTRKLAQKLGVEQPTLYWHVKNKRA

LLDALPIEMLDRHHTHFCPLEGESWQDFLRNNAKSFRCALLSHRDGAKVH

LGTRPTEKQYETLENQLAFLCQQGFSLENALYALSAVGHFTLGCVLEEQE

HQVAKEERETPTTDSMPPLLRQAIELFDRQGAEPAFLFGLELIICGLEKQ

LKCESGGPADALDDFDLDMLPADALDDFDLDMLPADALDDFDLDMLPG
```

The tetOpr (ADH1tr-teto operator CYC1pr) in pSI499 is identical to tetOpr (ADH1tr-tetO operator-CYC1pr) in pSIB498 above.

Common parts for yGG include the following. An exemplary nucleic acid sequence for yGG-TDH1pr in pSIB027 is provided below (12-871, TDH1 promoter; SEQ ID NO: 30):

```
ggtctcacagtctcgatggattagtttctcacaggtaacataacaaaaac

caagaaaagcccgcttctgaaaactacagttgacttgtatgctaaagggc

cagactaatgggaggagaaaaagaaacgaatgtatatgctcatttacact

ctatatcaccatatggaggataagttgggctgagcttctgatccaattta

ttctatccattagttgctgatatgtcccaccagccaacacttgatagtat

ctactcgccattcacttccagcagcgccagtagggttgttgagcttagta

aaaatgtgcgcaccacaagcctacatgactccacgtcacatgaaaccaca

ccgtggggccttgttgcgctaggaataggatatgcgacgaagacgcttct

gcttagtaaccacaccacattttcaggggtcgatctgcttgcttccttt

actgtcacgagcggcccataatcgcgclattattaaaaggcgcgagacag

caaacaggaagctcgggittcaaccttcggagtggtcgcagatctggaga

ctggatctttacaatacagtaaggcaagccaccatctgcttcttaggtgc

atgcgacggtatccacgtgcagaacaacatagtctgaagaagggggggag

gagcatgttcattctctgtagcagtaagagcttggtgataatgaccaaaa

ctggagtctcgaaatcatataaatagacaatatatttcacacaatgaga

tttgtagtacagttctattctctctcttgcataaataagaaattcatcaa

gaacttggtttgatatttcaccaacacacacaaaaaacagtacttcacta

aatttacacacaaaacaaaatgagagacc
```

An exemplary nucleic acid sequence for yGG-mutated CMVpr in pSIB237 is provided below (12-781, mutated CMV promoter; SEQ ID NO: 31):

ggtctcacagtgagcttggcccattgcatacgttgtatccatatcataat
atgtacatttatattggctcatgtccaacattaccgccatgttgacattg
attattgactagttattaatagtaatcaattacggggtcattagttcata
gcccatatatggagttccgcgttacataacttacggtaaatggcccgcct
ggctgaccgcccaacgacccccgcccattgacgtcaataatgacgtatgt
tcccatagtaacgccaatagggactttccattgacgtcaatgggtggagt
atttacggtaaactgcccacttggcagtacatcaagtgtatcatatgcca
agtacgccccctattgacgtcaatgacggtaaatggcccgcctggcatta
tgcccagtacatgaccttatgggactacctacttggcagtacatctacgt
attagtcatcgctattaccatggtgatgcggttaggcagtacatcaatgg
gcgtggatagcggtttgactcacggggatttccaagtctccaccccattg
acgtcaatgggagtttgttaggcaccaaaatcaacgggactttccaaaat
gtcgtaacaactccgccccattgacgcaaatgggcggtaggcgtgtacgg
tgggaggtctatataagcagagctcgtttagtgaaccgtcagatcgcctg
tagacgccatccacgctgttttgacctccatagaagacaccgggaccgat
ccagcctccgcggcccgaattaattcataatgagagacc An exemplary nucleic acid sequence for yGG-ScGSH1tr in pSIB031 is provided below (12-718, GSH1 terminator; SEQ ID NO: 32):

ggtctcgtgagactccttttacttcggttgtgaaagaaagttgacattat
cgatttgggtgacacggtgattgaaaaagcaacgaccagtattatacctc
ttttttttattattcagtttatatttttgcaagtgatcttaagcatttct
acacaaacttatgccaacgtgaccatttattattttatatagcaaaaaaa
aatgaggggccttgcagaacaattgttgcgagtttctaataacaagcacg
tagaatattggccatttaatttttctcttcaatttatagaatggttgtgt
tagtgacaaaaagaatattcttccccgccaggactcgaacctggaatctc
ctggttcgtagccagacgccgtgaccattgggccacgaggaacaagaata
taaagatctctgagggcaaggtatgcctatgtcgcaataaaatgtttgtt
cctgcgcaaaagtaaagttctattaatatacaactacacagttatcggtt
cacactattcgatagttgtaaaaaccattttgataaagatataacaaggc
gtttattaaggacatttttgctacaagtcgtgaagtattgattgtaggcg
atcgttggtaactttctccatatcggaatattcaatattgaactcacccc
tcccttgcgataagctccttagcttattggtgtaggtggtaatttccctt
agtggcactttcgcttttcgagacc An exemplary nucleic acid sequence for yGG-mutaed STR1tr in pSIB206 is provided below (12-741, mutated STR1; SEQ ID NO: 33):

ggtctcgtgagtcgccagtgccatgtttctgccttcgaccggaccattta
agtacgataaatatccattataaatatatagtctaaaatatccattaata
ctgtgctcaatcaatcgtgttagatgatttagttattccaaatcgttatt
atagtgcagaagtagtatacataaaggcatatgcatgcgatttggaagta -continued acgctcgccgtagacaagtaagaatgcctgctgtcttgagaaccaggtcc
aaagaatcctctatagagcagaagcctgcttccagaactagaacgagatc
aagaaggggcaagcgtggtcgtgacgatgatgatgatgacgacgatgagg
aaagcgatgatgcatacgatgaagtaggtaatgactatgacgagtatgct
tcaagagcgaagctggccaccaataggcccttcgaaatagtcgcgggact
gcctgctagtgtggagctgcccaactataactcttcgcttactcatccgc
aatcaattaaaaattctggggtgctttacgactctctggtcagttccaga
agaacctgggttcagggtgagatgtttgaactgtattggcgaagacctaa
gaaaattgttagtgaatctaccccagcagcgacggagagtccaacatctg
gaacgattcctttgattcgagataagatgcagaaaatgtgcgattgtgta
atgagtggaggtcctcacacgttcaaagttagacttttggagacc An exemplary nucleic acid sequence for yGG-SOL3tr in pSIB639 is provided below (12-562, SOL3 terminator; SEQ ID NO: 34):

ggtctcatgagaaaagacacacatgcgagctttcgaacctcagatgctaa
tattacgtgttatatataccaaactttataaaatgacatagatattttat
gctgtgatagctacctgttatggagaagctcttcttattccccctgtcaa
ctttcatactcttgtagaatttcctttatgataggtttatcgcttacgaa
tttagactttgatgtgatgggtttggcacctgttctttaccacaaccttt
gcgtgcctcatcaatagcgtttgatctgtcgggaaatttgtatttgtaga
gtgcatccttgcacattgtatagacccaattacgctcttctaacaggttc
acgaacgattttatttcaggaacagagccgattgtactttttgaacctat
aatgatcagcttggatttggcccttgtcatggcaacattgactcttctta
gctattcagcagcgctcctccatttaattgagaatttcttctaaccatgg
aaataataatgcactttagtcacgaccttgaaactgatcagcagtcaaga
tctctagcttttagagacc Common Parts for yGG: pSIB027, pSIB237, pSIB031, pSIB206, and pSIB639

These parts were described previously Ikushima et al., 2015 G3 (Bethesda), Vol. 5 (10), 1983-1990, incorporated herein by reference) and represent "promoter" or "terminator" parts for acceptor vectors in yeast GoldenGate assembly.

Example 9: Select Annotated Sequences

Described below are select annotated sequences for the constructs provided herein.

```
LOCUS NLS 24 bp ds-DNA linear 03-DEC-2016
DEFINITION.

ACCESSION

VERSION

SOURCE .

ORGANISM .

COMMENT

COMMENT

COMMENT         ApEinfo: methylated:1

FEATURES        Location/Qualifiers

misc_feature    1..24
                /label=NLS(SV40)
                /ApEinfo_fwdcolor="#36ff21"
                /ApEinfo_revcolor="#36ff21"
                /ApEinfo_graphicformat="arrow_data {{0 1 2 0 0 -1}{}0}
                width 5 offset 0"

ORIGIN
1 ATGCCAAAGA AGAAGAGAAA GGTT (SEQ ID NO: 35)
//
```

```
LOCUS SEQ_ID_NO_9_PhIF 729 bp ds-DNA linear 03-DEC-2016
DEFINITION .

ACCESSION

VERSION

SOURCE .

ORGANISM.

COMMENT

COMMENT

COMMENT         ApEinfo: methylated:1

FEATURES        Location/Qualifiers

misc_feature    1..600
                /label=PhIF
                /ApEinfo_fwdcolor="cyan"
                /ApEinfo_revcolor="cyan"
                /ApEinfo_graphicformat="arrow data {{0 1 2 0 0 -1}{}0}
                width 5 offset 0"

misc_feature    601..726
                /label=VP16
                /ApEinfo_fwdcolor="#2109ff"
                /ApEinfo_revcolor="#2109ff"
                /ApEinfo_graphicformat="arrow data {{0 1 2 0 0 -1}{}0}
                width 5 offset 0"

misc_feature    727..729
                /label=Stop codon
                /ApEinfo_fwdcolor="#ff8080"
                /ApEinfo_revcolor="#ff8080"
                /ApEinfo_graphicformat="arrow data {{0 1 2 0 0 -1}{}0}
                width 5 offset 0"
ORIGIN
  1             ATGGCTAGAA CCCCATCTCG ATCTTCTATC GGTTCTTTGC GATCTCCACA CACCCACAAG
```

-continued

```
 61          GCTATCTTGA CCTCTACCAT CGAAATCTTG AAGGAATGTG GTTACTCTGG TTTGTCTATC

121          GAATCTGTTG CTAGAAGAGC TGGTGCTTCT AAGCCAACCA TCTACAGATG GTGGACCAAC

181          AAGGCTGCTT TGATCGCTGA AGTTTACGAA AACGAATCTG AACAAGTTAG AAAGTTCCCA

241          GACTTGGGTT CTTTCAAGGC TGACTTGGAC TTCTTGTTGA GAAACTTGTG GAAGGTTTGG

301          AGAGAAACCA TCTGTGGTGA GGCTTTCAGA TGTGTTATCG CTGAAGCTCA ATTGGACCCA

361          GCTACCTTGA CCCAATTGAA GGACCAATTC ATGGAAAGAA GAAGAGAAAT GCCAAAGAAG

421          TTGGTTGAAA ACGCTATCTC TAACGGTGAA TTGCCAAAGG ACACCAACAG AGAATTGTTG

481          TTGGACATGA TCTTCGGTTT CTGTTGGTAC AGATTGTTGA CCGAACAATT GACCGTTGAA

541          CAAGACATCG AAGAGTTCAC CTTCTTGTTG ATCAACGGTG TTTGTCCAGG AACCCAAAGA

601          gggccggccG ACGCTTTGGA CGACTTCGAC TTGGACATGT TGCCTGCAGA TGCACTTGAT

661          GATTTTGATC TTGATATGCT TCCAGCAGAC GCATTGGATG ACTTTGACCT TGACATGCTT

721          CCTGGTTGA (SEQ ID NO: 9; PhIF-VP16 in SIB337)
//
```

```
LOCUS SIB921_G339_A63L 624 bp ds-DNA linear 02-DEC-2016
DEFINITION .

ACCESSION

VERSION

SOURCE .

ORGANISM .

COMMENT

COMMENT        ApEinfo:methylated:1

FEATURES       Location/Qualifiers

misc_feature   25..621
               /label=PhIF
               /ApEinfo_fwdcolor="cyan"
               /ApEinfo_revcolor="cyan"
               /ApEinfo_graphicformat="arrow data {{0 1 2 0 0 -1}{}0}
               width 5 offset 0"

misc_feature   622..624
               /label=STOP codon
               /ApEinfo_fwdcolor="#ff1fdd"
               /ApEinfo_revcolor="#ff1fdd"
               /ApEinfo_graphicformat="arrow data {{0 1 2 0 0 -1}{}0}
               width 5 offset 0"

misc_feature   1..24
               /label=NLS(SV40)
               /ApEinfo_fwdcolor="#36ff21"
               /ApEinfo_revcolor="#36ff21"
               /ApEinfo_graphicformat="arrow data {{0 1 2 0 0 -1}{}0}
               width 5 offset 0"

ORIGIN
  1            ATGCCAAAGA AGAAGAGAAA GGTTGCTAGA ACCCCATCTC GATCTTCTAT CGGTTCTTTG

 61            CGATCTCCAC ACACCCACAA GGCTATCTTG ACCTCTACCA TCGAAATCTT GAAGGAATGT

121            GGTTACTCTG GTTTGTCTAT CGAATCTGTT GCTAGAAGAG CTGGTGCTTC TAAGCCAACC

181            ATCTACAGAT GGTGGACCAA CAAGGCTGCT TTGATCGCTG AAGTTTACGA AAACGAATCT

241            GAACAAGTTA GAAAGTTCCC AGACTTGGGT TCTTTCAAGG CTGACTTGGA CTTCTTGTTG

301            AGAAACTTGT GGAAGGTTTG GAGAGAAACC ATCTGTGGTG AGGCTTTCAG ATGTGTTATC
```

-continued

```
361           GCTGAAGCTC AATTGGACCC AGCTACCTTG ACCCAATTGA AGGACCAATT CATGGAAAGA

421           AGAAGAGAAA TGCCAAAGAA GTTGGTTGAA AACGCTATCT CTAACGGTGA ATTGCCAAAG

481           GACACCAACA GAGAATTGTT GTTGGACATG ATCTTCGGTT TCTGTTGGTA CAGATTGTTG

541           ACCGAACAAT TGACCGTTGA ACAAGACATC GAAGAGTTCA CCTTCTTGTT GATCAACGGT

601           GTTTGTCCAG GAACCCAAAG ATGA (SEQ ID NO: 11; NLS-PhIF in SIB921)
//
```

```
LOCUS phlPr_in_pSIB918 653 bp ds-DNA circular 03-DEC-2016
DEFINITION .

ACCESSION

VERSION

SOURCE .

ORGANISM .

COMMENT

COMMENT

COMMENT      ApEinfo:methylated:1

FEATURES     Location/Qualifiers

misc_feature 220..249
             /label=core of PhIF operator
             /ApEinfo_fwdcolor="cyan"
             /ApEinfo_revcolor="cyan"
             /ApEinfo graphicformat="arrow_data {{0 1 2 0 0 -1}{}0}
             width 5 offset 0"

misc_feature 335..374
             /label=1 unit (PhIFop.core+flank)
             /ApEinfo_fwdcolor="#ffd580"
             /ApEinfo_revcolor="#ffd580"
             /ApEinfo_graphicformat="arrow_data {{0 1 2 0 0 -1}{}0}
             width 5 offset 0"

misc_feature 204..214
             /label=Adapter_FseI-XmaI
             /ApEinfo_fwdcolor="#fffbf4"
             /ApEinfo_revcolor="#fffbf4"
             /ApEinfo_graphicformat="arrow_data {{0 1 2 0 0 -1}{}0}
             width 5 offset 0"

misc_feature 255..294
             /label=1 unit (PhIFop.core+flank)(1)
             /ApEinfo_label="1 unit (PhIFop.core+flank)"
             /ApEinfo_fwdcolor="#ffd580"
             /ApEinfo_revcolor="#ffd580"
             /ApEinfo_graphicformat="arrow_data {{0 1 2 0 0 -1}{}0}
             width 5 offset 0"

misc_feature 380..409
             /label=core of PhIF operator(1)
             /ApEinfo_label="core of PhIF operator"
             /ApEinfo_fwdcolor="cyan"
             /ApEinfo_revcolor="cyan"
             /ApEinfo_graphicformat="arrow_data {{0 1 2 0 0 -1}{}0}
             width 5 offset 0"

misc_feature 375..414
             /label=1 unit (PhIFop.core+flank)(2)
             /ApEinfo_label="1 unit (PhIFop.core+flank)"
             /ApEinfo_fwdcolor="#ffd580"
             /ApEinfo_revcolor="#ffd580"
             /ApEinfo_graphicformat="arrow_data {{0 1 2 0 0 -1}{}0}
             width 5 offset 0"

misc_feature 215..254
```

-continued

```
                /label=1 unit (PhIFop.core+flank)(3)
                /ApEinfo_label="1 unit (PhIFop.core+flank)"
                /ApEinfo_fwdcolor="#ffd580"
                /ApEinfo_revcolor="#ffd580"
                /ApEinfo_graphicformat="arrow_data {{0 1 2 0 0 -1}{}0}
                width 5 offset 0"

misc_feature    420..449
                /label=core of PhIF operator(2)
                /ApEinfo_label="core of PhIF operator"
                /ApEinfo_fwdcolor="cyan"
                /ApEinfo_revcolor="cyan"
                /ApEinfo_graphicformat="arrow_data {{0 1 2 0 0 -1}{}0}
                width 5 offset 0"

misc_feature    507..653
                /label=ScCYC1 promoter
                /ApEinfo_fwdcolor="#1dff0f"
                /ApEinfo_revcolor="#1dff0f"
                /ApEinfo_graphicformat="arrow_data {{0 1 2 0 0 -1}{}0}
                width 5 offset 0"

misc_feature    260..289
                /label=core of PhIF operator(3)
                /ApEinfo_label="core of PhIF operator"
                /ApEinfo_fwdcolor="cyan"
                /ApEinfo_revcolor="cyan"
                /ApEinfo_graphicformat="arrow_data {{0 1 2 0 0 -1}{}0}
                width 5 offset 0"

misc_feature    415..454
                /label=1 unit (PhIFop.core+flank)(4)
                /ApEinfo_label="1 unit (Ph1Fop.core+flank)"
                /ApEinfo_fwdcolor="#ffd580"
                /ApEinfo_revcolor="#ffd580"
                /ApEinfo_graphicformat="arrow_data {{0 1 2 0 0 -1}{}0}
                width 5 offset 0"

misc_feature    300..329
                /label=core of PhIF operator(4)
                /ApEinfo_label="core of PhIF operator"
                /ApEinfo_fwdcolor="cyan"
                /ApEinfo_revcolor="cyan"
                /ApEinfo_graphicformat="arrow_data {{0 1 2 0 0 -1}{}0}
                width 5 offset 0"

misc_feature    295..334
                /label=1 unit (PhIFop.core+flank)(5)
                /ApEinfo_label="1 unit (PhIFop.core+flank)"
                /ApEinfo_fwdcolor="#ffd580"
                /ApEinfo_revcolor="#ffd580"
                /ApEinfo_graphicformat="arrow_data {{0 1 2 0 0 -1}{}0}
                width 5 offset 0"

misc_feature    1..203
                /label=ADH1 transcriptional terminator
                /ApEinfo_fwdcolor="#ffec1f"
                /ApEinfo_revcolor="#ffec1f"
                /ApEinfo_graphicformat="arrow_data" {{0 1 2 0 0 -1}{}0}
                width 5 offset 0"

misc_feature    455..494
                /label=1 unit (PhIFop.core+flank)(6)
                /ApEinfo_label="1 unit (PhIFop.core+flank)"
                /ApEinfo_fwdcolor="#ffd580"
                /ApEinfo_revcolor="#ffd580"
                /ApEinfo_graphicformat="arrow_data {{0 1 2 0 0 -1}{}0}
                width 5 offset 0"

misc_feature    340..369
                /label=core of PhIF operator(5)
                /ApEinfo_label="core of PhIF operator"
                /ApEinfo_fwdcolor="cyan"
                /ApEinfo_revcolor="cyan"
                /ApEinfo_graphicformat="arrow_data {{0 1 2 0 0 -1}{}0}
                width 5 offset 0"

misc_feature    460..489
                /label=core of PhIF operator(6)
```

```
               /ApEinfo_label="core of PhIF operator"
               /ApEinfo_fwdcolor="cyan"
               /ApEinfo_revcolor="cyan"
               /ApEinfo_graphicformat="arrow_data {{0 1 2 0 0 -1}{}0}
               width 5 offset 0"

misc_feature  495..506
               /label=Adapter_XmaI-FseI
               /ApEinfo_fwdcolor="#fffefb"
               /ApEinfo_revcolor="#fffefb"
               /ApEinfo_graphicformat="arrow_data {{0 1 2 0 0 -1}{}0}
               width 5 offset 0"

misc_feature  215..494
               /label=phIF operator
               /ApEinfo_fwdcolor="#ff8080"
               /ApEinfo_revcolor="#ff8080"
               /ApEinfo_graphicformat="arrow_data {{0 1 2 0 0 -1}{}0}
               width 5 offset 0"

ORIGIN
  1           cacttctaaa taagcgaatt tcttatgatt tatgattttt attattaaat aagttataaa

 61           aaaaataagt gtatacaaat tttaaagtga ctcttaggtt ttaaaacgaa aattcttgtt

121           cttgagtaac tctttcctgt aggtcaggtt gctttctcag gtatagcatg aggtcgctct

181           tattgaccac acctctaccg gcaggccggc ccggTATGTA TGATACGAAA CGTACCGTAT

241           CGTTAAGGTA GCGTTATGTA TGATACGAAA CGTACCGTAT CGTTAAGGTA GCGTTATGTA

301           TGATACGAAA CGTACCGTAT CGTTAAGGTA GCGTTATGTA TGATACGAAA CGTACCGTAT

361           CGTTAAGGTA GCGTTATGTA TGATACGAAA CGTACCGTAT CGTTAAGGTA GCGTTATGTA

421           TGATACGAAA CGTACCGTAT CGTTAAGGTA GCGTTATGTA TGATACGAAA CGTACCGTAT

481           CGTTAAGGTA GCGTcccggg ccggcctatg gcatgcatgt gctctgtatg tatataaaac

541           tcttgttttc ttcttttctc taaatattct ttccttatac attaggtcct ttgtagcata

601           aattactata cttctataga cacgcaaaca caaatacaca cactaaatta ATA
              (SEQ ID NO: 13; phlPr in pSIB918)

//
```

```
LOCUS SEQ_ID_NO_15_ADH 823 bp ds-DNA circular 03-DEC-2016
DEFINITION .

ACCESSION

VERSION

SOURCE .

ORGANISM .

COMMENT

COMMENT

COMMENT       ApEinfo:methylated:1

FEATURES      Location/Qualifiers

misc_feature  693..732
               /label=1 unit (PhIFop.core+flank)
               /ApEinfo_fwdcolor="#ffd580"
               /ApEinfo_revcolor="green"
               /ApEinfo_graphicformat="arrow_data {{0 1 2 0 0 -1}{}0}
               width 5 offset 0"

misc_feature  733..762
               /label=core of PhIF operator
               /ApEinfo_fwdcolor="cyan"
               /ApEinfo_revcolor="green"
```

-continued

```
                /ApEinfo_graphicformat="arrow_data {{0 1 2 0 0 -1}{}0}
                width 5 offset 0"

misc_feature    733..767
                /label=1 unit (PhIFop.core+flank)(1)
                /ApEinfo_label="1 unit (PhIFop.core+flank)"
                /ApEinfo_fwdcolor="#ffd580"
                /ApEinfo_revcolor="green"
                /ApEinfo_graphicformat="arrow_data {{0 1 2 0 0 -1}{}0}
                width 5 offset 0"

misc_feature    698..727
                /label=core of PhIF operator(1)
                /ApEinfo_label="core of PhIF operator"
                /ApEinfo_fwdcolor="cyan"
                /ApEinfo_revcolor="green"
                /ApEinfo_graphicformat="arrow_data {{0 1 2 0 0 -1}{}0}
                width 5 offset 0"

misc_feature    768..793
                /label=ADH1i (down)
                /ApEinfo_fwdcolor="#fff449"
                /ApEinfo_revcolor="#fff449"
                /ApEinfo_graphicformat="arrow_data {{0 1 2 0 0 -1}{}0}
                width 5 offset 0"

promoter        794..823
                /label=synthetic sequence from ADHipr
                /ApEinfo_fwdcolor="#b0ffa8"
                /ApEinfo_revcolor="#b0ffa8"
                /ApEinfo graphicformat="arrow_data {{0 1 2 0 0 -1}{}0}
                width 5 offset 0"

misc_feature    1..692
                /label=ADH1i (up)
                /ApEinfo_fwdcolor="#c7ff70"
                /ApEinfo_revcolor="#c7ff70"
                /ApEinfo_graphicformat="arrow_data {{0 1 2 0 0 -1}{}0}
                width 5 offset 0"

misc_feature    179..179
                /label=T->A (mutation)
                /ApEinfo_fwdcolor="cyan"
                /ApEinfo_revcolor="cyan"
                /ApEinfo_graphicformat="arrow_data {{0 1 2 0 0 -1}{}0}
                width 5 offset 0"

misc_feature    693..767
                /label=PhIF operator
                /ApEinfo_fwdcolor="#ff8080"
                /ApEinfo_revcolor="#ff8080"
                /ApEinfo_graphicformat="arrow_data {{0 1 2 0 0 -1}{}0}
                width 5 offset 0"

ORIGIN
  1             TAAAGTCCAA TGCTAGTAGA GAAGGGGGGT AACACCCCTC CGCGCTCTTT TCCGATTTTT

 61             TTCTAAACCG TGGAATATTT CGGATATCCT TTTGTTGTTT CCGGGTGTAC AATATGGACT

121             TCCTCTTTTC TGGCAACCAA ACCCATACAT CGGGATTCCT ATAATACCTT CGTTGGTCaC

181             CCTAACATGT AGGTGGCGGA GGGGAGATAT ACAATAGAAC AGATACCAGA CAAGACATAA

241             TGGGCTAAAC AAGACTACAC CAATTACACT GCCTCATTGA TGGTGGTACA TAACGAACTA

301             ATACTGTAGC CCTAGACTTG ATAGCCATCA TCATATCGAA GTTTCACTAC CCTTTTTCCA

361             TTTGCCATCT ATTGAAGTAA TAATAGGCGC ATGCAACTTC TTTTCTTTTT TTTTCTTTTC

421             TCTCTCCCCC GTTGTTGTCT CACCATATCC GCAATGACAA AAAAATGATG GAAGACACTA

481             AAGGAAAAAA TTAACGACAA AGACAGCACC AACAGATGTC GTTGTTCCAG AGCTGATGAG

541             GGGTATCTCG AAGCACACGA AACTTTTTCC TTCCTTCATT CACGCACACT ACTCTCTAAT

601             GAGCAACGGT ATACGGCCTT CCTTCCAGTT ACTTGAATTT GAAATAAAAA AAGTTTGCT

661             GTCTTGCTAT CAAGTATAAA TAGACCTGCA ATTATGTATG ATACGAAACG TACCGTATCG
```

```
721          TTAAGGTAGC GTATGATACG AAACGTACCG TATCGTTAAG GTAGCGTCTT TCTTCCTTGT

781          TTCTTTTTCT GCAggtcgac tctagaggat ccccgggtat taa (SEQ ID NO: 15; ADHph02 in pS1B924)

//
```

```
LOCUS SEQ_ID_NO_17_cym 762 bp ds-DNA linear 03-DEC-2016

DEFINITION .

ACCESSION

VERSION

SOURCE .

ORGANISM.

COMMENT

COMMENT

COMMENT      ApEinfo:methylated:1

FEATURES     Location/Qualifiers

misc_feature 634..759
             /label=VP16
             /ApEinfo_fwdcolor="#2109ff"
             /ApEinfo_reycolor="#2109ff'
             /ApEinfo_graphicformat="arrow_data {{0 1 2 0 0 -1}{}0}
             width 5 offset 0"

misc_feature 25..633
             /label=CymR
             /ApEinfo_fwdcolor="cyan"
             /ApEinfo_revcolor="cyan"
             /ApEinfo_graphicformat="arrow_data {{0 1 2 0 0 -1}{}0}
             width 5 offset 0"

misc_feature 1..24
             /label=NLS(SV40)
             /ApEinfo_fwdcolor="#ff7b78"
             /ApEinfo_revcolor="#ff7b78"
             /ApEinfo_graphicformat="arrow_data {{0 1 2 0 0 -1}{}0}
             width 5 offset 0"

misc_feature 760..762
             /label=Stop codon
             /ApEinfo_fwdcolor="#ff8080"
             /ApEinfo_revcolor="#ff8080"
             /ApEinfo_graphicformat="arrow_data {{0 1 2 0 0 -1}{}0}
             width 5 offset 0"

ORIGIN
  1          ATGCCAAAGA AGAAGAGAAA GGTAATGTCT CCAAAGAGAA GAACTCAAGC TGAAAGAGCT

 61          ATGGAAACTC AAGGTAAGTT GATCGCTGCT GCTTTGGGTG TTTTGAGAGA AAAGGGTTAC

121          GCTGGTTTCA GAATCGCTGA CGTTCCAGGT GCTGCTGGTG TTTCTAGAGG TGCTCAATCT

181          CACCACTTCC CAACCAAGTT GGAATTGTTG TTGGCTACCT TCGAATGGTT GTACGAACAA

241          ATCACCGAAA GATCTAGAGC TAGATTGGCT AAGTTGAAGC CAGAAGACGA CGTTATCCAA

301          CAAATGTTGG ACGACGCTGC TGAATTCTTC TTGGACGACG ACTTCTCTAT CTCTTTGGAC

361          TTGATCGTTG CTGCTGACCG CGATCCTGCT TTGAGAGAAG GTATCCAAAG AACCGTTGAA

421          AGAAACAGAT TCGTTGTTGA AGACATGTGG TTGGGTGTTT TGGTTTCTAG AGGTTTGTCT

481          CGCGACGACG CTGAAGACAT CTTGTGGTTG ATCTTCAACT CTGTTAGAGG TTTGGCTGTT

541          AGATCTTTGT GGCAAAAGGA CAAGGAAAGA TTCGAAAGAG TTAGAAACTC TACCTTGGAA

601          ATCGCTAGAG AAAGATACGC TAAGTTCAAG AGGgggccgg ccGACGCTTT GGACGACTTC
```

-continued

```
661        GACTTGGACA TGTTGCCTGC AGATGCACTT GATGATTTTG ATCTTGATAT GCTTCCAGCA

721        GACGCATTGG ATGACTTTGA CCTTGACATG CTTCCTGGTT GA (SEQ ID NO: 17; cymTA in pSIB470)

//
```

```
LOCUS SEQ_ID_NO_19_Cym 564 bp ds-DNA circular 04-DEC-2016

DEFINITION.

ACCESSION

VERSION

SOURCE .

ORGANISM.

COMMENT

COMMENT

COMMENT        ApEinfo:methylated:1

FEATURES       Location/Qualifiers

misc_feature   383..417
               /label=CymR operator P1
               /ApEinfo_fwdcolor="#83ff70"
               /ApEinfo_revcolor="#83ff70"
               /ApEinfo_graphicformat="arrow_data {{0 1 2 0 0 -1}{}0}
               width 5 offset 0"

misc_feature   204..207
               /label=acceptor
               /ApEinfo_fwdcolor="cyan"
               /ApEinfo_revcolor="green"
               /ApEinfo_graphicformat="arrow_data {{0 1 2 0 0 -1}{}0}
               width 5 offset 0"

misc_feature   348..382
               /label=CymR operator P1(1)
               /ApEinfo_label="CymR operator P1"
               /ApEinfo_fwdcolor="#83ff70"
               /ApEinfo_revcolor="#83ff70"
               /ApEinfo_graphicformat="arrow_data {{0 1 2 0 0 -1}{}0}
               width 5 offset 0"

misc_feature   388..413
               /label=binding site
               /ApEinfo_fwdcolor="#ff95f8"
               /ApEinfo_revcolor="#ff95f8"
               /ApEinfo_graphicformat="arrow_data {{0 1 2 0 0 -1}{}0}
               width 5 offset 0"

misc_feature   313..347
               /label=CymR operator P1(2)
               /ApEinfo_label="CymR operator Pl"
               /ApEinfo_fwdcolor="#83ff70"
               /ApEinfo_revcolor="#83ff70"
               /ApEinfo_graphicformat="arrow_data {{0 1 2 0 0 -1}{}0}
               width 5 offset 0"

misc_feature   278..312
               /label=CymR operator P1(3)
               /ApEinfo_label="CymR operator Pl"
               /ApEinfo_fwdcolor="#83ff70"
               /ApEinfo_revcolor="#83ff70"
               /ApEinfo_graphicformat="arrow_data {{0 1 2 0 0 -1}{}0}
               width 5 offset 0"

misc_feature   418..421
               /label=acceptor(1)
               /ApEinfo_label="acceptor"
               /ApEinfo_fwdcolor="#00ffff"
```

```
                 /ApEinfo_revcolor="green"
                 /ApEinfo_graphicformat="arrow_data {{0 1 2 0 0 -1}{}0}
                 width 5 offset 0"

misc_feature     243..277
                 /label=CymR operator P1(4)
                 /ApEinfo_label="CymR operator P1"
                 /ApEinfo_fwdcolor="#83ff70"
                 /ApEinfo_revcolor="#83ff70"
                 /ApEinfo_graphicformat="arrow_data {{0 1 2 0 0 -1}{}0}
                 width 5 offset 0"

misc_feature     208..242
                 /label=CymR operator P1(5)
                 /ApEinfo_label="CymR operator P1"
                 /ApEinfo_fwdcolor="#83ff70"
                 /ApEinfo_revcolor="#83ff70"
                 /ApEinfo_graphicformat="arrow_data {{0 1 2 0 0 -1}{}0}
                 width 5 offset 0"

misc_feature     1..203
                 /label=ADH1 transcriptional terminator
                 /ApEinfo_fwdcolor=#ffec1f"
                 /ApEinfo_revcolor="green"
                 /ApEinfo_graphicformat="arrow_data {{0 1 2 0 0 -1}{}0}
                 width 5 offset 0"

misc_feature     353..378
                 /label=binding site(1)
                 /ApEinfo_label="binding site"
                 /ApEinfo_fwdcolor="#ff95f8"
                 /ApEinfo_revcolor="#ff95f8"
                 /ApEinfo_graphicformat="arrow_data {{0 1 2 0 0 -1}{}0}
                 width 5 offset 0"

misc_feature     318..343
                 /label=binding site(2)
                 /ApEinfo_label="binding site"
                 /ApEinfo_fwdcolor="#ff95f8"
                 /ApEinfo_revcolor="#ff95f8"
                 /ApEinfo_graphicformat="arrow_data {{0 1 2 0 0 -1}{}0}
                 width 5 offset 0"

misc_feature     283..308
                 /label=binding site(3)
                 /ApEinfo_label="binding site"
                 /ApEinfo_fwdcolor="#ff95f8"
                 /ApEinfo_revcolor="#ff95f8"
                 /ApEinfo_graphicformat="arrow_data
                 width 5 offset 0"

misc_feature     419..564
                 /label=ScCYC1 promoter
                 /ApEinfo_fwdcolor="#1dff0f"
                 /ApEinfo_revcolor="green"
                 /ApEinfo_graphicformat="arrow_data {{0 1 2 0 0 -1}{}0}
                 width 5 offset 0"

misc_feature     248..273
                 /label=binding site(4)
                 /ApEinfo_label="binding site"
                 /ApEinfo_fwdcolor="#ff95f8"
                 /ApEinfo_revcolor="#ff95f8"
                 /ApEinfo_graphicformat="arrow_data {{0 1 2 0 0 -1}{}0}
                 width 5 offset 0"

misc_feature     213..238
                 /label=binding site(5)
                 /ApEinfo_label="binding site"
                 /ApEinfo_fwdcolor="#ff95f8"
                 /ApEinfo_revcolor="#ff95f8"
                 /ApEinfo_graphicformat="arrow_data {{0 1 2 0 0 -1}{}0}
                 width 5 offset 0"
```

```
misc_feature   208..417
               /label=cymR operator
               /ApEinfo_fwdcolor="#ff0000"
               /ApEinfo_revcolor="#ff0000"
               /ApEinfo_graphicformat="arrow_data {{0 1 2 0 0 -1}{}0}
               width 5 offset 0"

ORIGIN
  1            cacttctaaa taagcgaatt tcttatgatt tatgattnt attattaaat aagttataaa

 61            aaaaataagt gtatacaaat tttaaagtga ctcttaggtt ttaaaacgaa aattchgtt

121            cttgagtaac tctttcctgt aggtcaggtt gctttctcag gtatagcatg aggtcgctct

181            tattgaccac acctctaccg gcaaggtAAG AAAGAAACAA ACCAACCTGT CTGTATTATC

241            TCAAGAAAGA AACAAACCAA CCTGTCTGTA TTATCTCAAG AAAGAAACAA ACCAACCTGT

301            CTGTATTATC TCAAGAAAGA AACAAACCAA CCTGTCTGTA TTATCTCAAG AAAGAAACAA

361            ACCAACCTGT CTGTATTATC TCAAGAAAGA AACAAACCAA CCTGTCTGTA TTATCTCaat

421            ggcatgcatg tgctctgtat gtatataaaa ctcttgatt cttcttnct ctaaatattc

481            tttccttata cattaggtcc tttgtagcat aaattactat acttctatag acacgcaaac

541            acaaatacac acactaaatt aATA (SEQ ID NO: 19; CymPr in pSIB803)

//
```

```
LOCUS SEQ_ID_NO_22_Tab 747 bp ds-DNA circular 04-DEC-2016

DEFINITION.

ACCESSION

VERSION

SOURCE .

ORGANISM.

COMMENT

COMMENT

COMMENT       ApEinfo:methylated:1

FEATURES      Location/Qualifiers

misc_feature  1..618
              /label=TetR
              /ApEinfo_fwdcolor="cyan"
              /ApEinfo_revcolor="cyan"
              /ApEinfo_graphicformat="arrow_data {{0 1 2 0 0 -1}{}0}
              width 5 offset 0"

misc_feature  619..744
              /label=VP16
              /ApEinfo_fwdcolor="#ff1fdd"
              /ApEinfo_revcolor="#ff1fdd"
              /ApEinfo_graphicformat="arrow_data {{0 1 2 0 0 -1}{}0}
              width 5 offset 0"

misc_feature  745..747
              /label=Stop codon
              /ApEinfo_fwdcolor="#ff8080"
              /ApEinfo_revcolor="#ff8080"
              /ApEinfo_graphicformat="arrow_data {{0 1 2 0 0 -1}{}0}
              width 5 offset 0"

ORIGIN
  1           ATGAGTAGAT TGGACAAGTC TAAGGTTATC AACTCTGCTT TGGAATTGTT GAACGAAGTT

 61           GGTATCGAAG GTTTGACCAC CAGAAAGTTG GCTCAAAAGT TGGGTGTTGA ACAACCAACC
```

```
121         TTGTACTGGC ACGTTAAGAA CAAGAGAGCT TTGTTGGACG CTTTGGCTAT CGAAATGTTG

181         GACAGACACC ACACCCACTT CTGTCCATTG GAAGGTGAAT CTTGGCAAGA CTTCTTGAGA

241         AACAACGCTA AGTCTTTCAG ATGTGCTTTG CTCTCTCACC GCGACGGTGC TAAGGTTCAC

301         TTGGGAACCA GACCAACCGA AAAGCAATAC GAAACCTTGG AAAACCAATT GGCTTTCTTG

361         TGTCAACAAG GTTTCTCTTT GGAAAACGCT TTGTACGCTT TGTCTGCTGT TGGTCACTTC

421         ACCTTGGGTT GTGTTTTGGA AGACCAAGAA CACCAAGTTG CTAAGGAAGA AAGAGAAACC

481         CCAACCACCG ACTCTATGCC ACCATTGCTC AGACAAGCTA TCGAATTGTT CGACCACCAA

541         GGTGCTGAAC CAGCTTTCTT GTTCGGTTTG GAATTGATCA TCTGTGGTTT GGAAAAGCAA

601         TTGAAGTGTG AATCTGGTGG GCCGGCCGAC GCTTTGGACG ACTTCGACTT GGACATGTTG

661         CCAGCTGACG CTTTGGACGA CTTCGACTTG GACATGTTGC CAGCTGACGC TTTGGACGAC

721         TTCGACTTGG ACATGTTGCC AGGTTGA (SEQ ID NO: 22; Table 4 tTA (=tetR-
            VP16) in pSIB498)

//
```

```
LOCUS SEQ_ID_NO_24_Tab 667 bp ds-DNA circular 04-DEC-2016

DEFINITION .

ACCESSION

VERSION

SOURCE .

ORGANISM .

COMMENT

COMMENT

COMMENT        ApEinfo: methylated:1

FEATURES       Location/Qualifiers

misc_feature   521 . . . 667
               /label = ScCYC1 promoter
               /ApEinfo_fwdcolor = "#1dff0f"
               /ApEinfo_revcolor = "green"
               /ApEinfo_graphicformat = "arrow_data {{0 1 2 0 0 -1} { } 0}
               width 5 offset 0"

misc_feature   1 . . . 203
               /label = ADH1 transcriptional terminator
               /ApEinfo_fwdcolor = "#ffec 1f"
               /ApEinfo_revcolor = "green"
               /ApEinfo_graphicformat = "arrow_data {{0 1 2 0 0 -1} { } 0}
               width 5 offset 0"

misc_feature   216 . . . 508
               /label = tetO*7
               /ApEinfo_fwdcolor = "cyan"
               /ApEinfo_revcolor = "green"
               /ApEinfo_graphicformat = "arrow_data {{0 1 2 0 0 -1} { } 0}
               width 5 offset 0"

misc_feature   356 . . . 373
               /label = tetOmin
               /ApEinfo_fwdcolor = "#ff05 1a"
               /ApEinfo_revcolor = "green"
               /ApEinfo_graphicformat = "arrow_data {{0 1 2 0 0 -1} { } 0}
               width 5 offset 0"
```

-continued

| LOCUS SEQ_ID_NO_24_Tab 667 bp ds-DNA circular 04-DEC-2016 |
|---|

```
misc_feature    216 . . . 228
                /label = fw
                /ApEinfo_fwdcolor = "#8b7aff"
                /ApEinfo_revcolor = "green"
                /ApEinfo_graphicformat = "arrow_data {{0 1 2 0 0 -1} { } 0}
                width 5 offset 0"

misc_feature    384 . . . 396
                /label = fw(1)
                /ApEinfo_label = "fw"
                /ApEinfo_fwdcolor = "#9480ff"
                /ApEinfo_revcolor = "green"
                /ApEinfo_graphicformat = "arrow_data {{0 1 2 0 0 -1} { } 0}
                width 5 offset 0"

misc_feature    509 . . . 520
                /label = Adapter_XmaI-FseI
                /ApEinfo_fwdcolor = "#fffefb"
                /ApEinfo_revcolor = "green"
                /ApEinfo_graphicformat = "arrow_data {{0 1 2 0 0 -1} { } 0}
                width 5 offset 0"

misc_feature    229 . . . 247
                /label = tetOmin(1)
                /ApEinfo_label = "tetOmin"
                /ApEinfo_fwdcolor = "#ff2222"
                /ApEinfo_revcolor = "green"
                /ApEinfo_graphicformat = "arrow_data {{0 1 2 0 0 -1} { } 0}
                width 5 offset 0"

misc_feature    300 . . . 312
                /label = fw(2)
                /ApEinfo_label = "fw"
                /ApEinfo_fwdcolor = "#6e79ff"
                /ApEinfo_revcolor = "green"
                /ApEinfo_graphicformat = "arrow_data {{0 1 2 0 0 -1} { } 0}
                width 5 offset 0"

misc_feature    426 . . . 438
                /label = fw(3)
                /ApEinfo_label = "fw"
                /ApEinfo_fwdcolor = "#9990ff"
                /ApEinfo_revcolor = "green"
                /ApEinfo_graphicformat = "arrow_data {{0 1 2 0 0 -1} { } 0}
                width 5 offset 0"

misc_feature    272 . . . 289
                /label = tetOmin(2)
                /ApEinfo_label = "tetOmin"
                /ApEinfo_fwdcolor = "#ff1527"
                /ApEinfo_revcolor = "green"
                /ApEinfo_graphicformat = "arrow_data {{0 1 2 0 0 -1} { } 0}
                width 5 offset 0"

misc_feature    342 . . . 355
                /label = fw(4)
                /ApEinfo_label = "fw"
                /ApEinfo_fwdcolor = "#7f67ff"
                /ApEinfo_revcolor = "green"
                /ApEinfo_graphicformat = "arrow_data {{0 1 2 0 0 -1} { } 0}
                width 5 offset 0"

misc_feature    468 . . . 480
                /label = fw(5)
                /ApEinfo_label = "fw"
                /ApEinfo_fwdcolor = "#9568ff"
                /ApEinfo_revcolor = "green"
                /ApEinfo_graphicformat = "arrow_data {{0 1 2 0 0 -1} { } 0}
                width 5 offset 0"

misc_feature    204 . . . 215
                /label = Adapter_FseI-XmaI
                /ApEinfo_fwdcolor = "#fffbf4"
                /ApEinfo_revcolor = "green"
                /ApEinfo_graphicformat = "arrow_data {{0 1 2 0 0 -1} { } 0}
                width 5 offset 0"
```

```
LOCUS SEQ_ID_NO_24_Tab 667 bp ds-DNA circular 04-DEC-2016

misc_feature   313 . . . 331
               /label = tetOmin(3)
               /ApEinfo_label = "tetOmin"
               /ApEinfo_fwdcolor = "#ff0e26"
               /ApEinfo_revcolor = "green"
               /ApEinfo_graphicformat = "arrow_data {{0 1 2 0 0 -1} { } 0}
               width 5 offset 0"

misc_feature   481 . . . 499
               /label = tetOmin(4)
               /ApEinfo_label = "tetOmin"
               /ApEinfo_fwdcolor = "#ff0f1e"
               /ApEinfo_revcolor = "green"
               /ApEinfo_graphicformat = "arrow_data {{0 1 2 0 0 -1} { } 0}
               width 5 offset 0"

misc_feature   258 . . . 271
               /label = fw(6)
               /ApEinfo_label = "fw"
               /ApEinfo_fwdcolor = "#8172ff"
               /ApEinfo_revcolor = "green"
               /ApEinfo_graphicformat = "arrow_data {{0 1 2 0 0 -1} { } 0}
               width 5 offset 0"

misc_feature   221 . . . 257
               /label = Native Tet0 of E. coli
               /ApEinfo_fwdcolor = "#f1beff"
               /ApEinfo_revcolor = "green"
               /ApEinfo_graphicformat = "arrow_data {{0 1 2 0 0 -1} { } 0}
               width 5 offset 0"

misc_feature   397 . . . 415
               /label = tetOmin(5)
               /ApEinfo_label = "tetOmin"
               /ApEinfo_fwdcolor = "#ff020e"
               /ApEinfo_revcolor = "green"
               /ApEinfo_graphicformat = "arrow_data {{0 1 2 0 0 -1} { } 0}
               width 5 offset 0"

misc_feature   439 . . . 457
               /label = tetOmin(6)
               /ApEinfo_label = "tetOmin"
               /ApEinfo_fwdcolor = "#ff1919"
               /ApEinfo_revcolor = "green"
               /ApEinfo_graphicformat = "arrow_data {{0 1 2 0 0 -1} { } 0}
               width 5 offset 0"

misc_feature   216 . . . 508
               /label = tetR operator
               /ApEinfo_fwdcolor = "#ff0000"
               /ApEinfo_revcolor = "#ff0000"
               /ApEinfo_graphicformat = "arrow_data {{0 1 2 0 0 -1} { } 0}
               width 5 offset 0"

ORIGIN
  1            cacttctaaa taagcgaatt tcttatgatt tatgattttt attattaaat aagttataaa

 61            aaaaataagt gtatacaaat tttaaagtga ctcttaggtt ttaaaacgaa aattcttgtt

121            cttgagtaac tctttcctgt aggtcaggtt gctttctcag gtatagcatg aggtcgctct

181            tattgaccac acctctaccg gcaggccggc ccgggtcgag tttaccactc cctatcagtg

241            atagagaaaa gtgaaagtcg agtttaccac tccctatcag tgatagagaa aagtgaaagt

301            cgagtttacc actccctatc agtgatagag aaaagtgaaa gtcgagttta ccactcccta

361            tcagtgatag agaaaagtga aagtcgagtt taccactccc tatcagtgat agagaaaagt

421            gaaagtcgag tttaccactc cctatcagtg atagagaaaa gtgaaagtcg agtttaccac

481            tccctatcag tgatagagaa aagtgaaacc cgggccggcc tatggcatgc atgtgctctg

541            tatgtatata aaactcttgt tttcttcttt tctctaaata ttctttcctt atacattagg

601            tcctttgtag cataaattac tatacttcta tagacacgca aacacaaata cacacactaa
```

| LOCUS SEQ_ID_NO_24_Tab 667 bp ds-DNA circular 04-DEC-2016 |
|---|

661 attaATA (SEQ ID NO: 24; Table 4; tetOpr (=ADH1tr-tetO operator-CYC1pr) in pSIB498)
//

| LOCUS SEQ_ID_NO_25_Tab 711 bp ds-DNA circular 04-DEC-2016 |
|---|

DEFINITION .

ACCESSION

VERSION

SOURCE .

ORGANISM .

COMMENT

COMMENT

COMMENT ApEinfo: methylated:1

FEATURES Location/Qualifiers misc_feature 559 . . . 684
/label = VP16
/ApEinfo_fwdcolor = "#2109ff"
/ApEinfo_revcolor = "#2109ff"
/ApEinfo_graphicformat = "arrow_data {{0 1 2 0 0 -1} { } 0}
width 5 offset 0"

misc_feature 685 . . . 708
/label = NLS (SV40)
/ApEinfo_fwdcolor = "#ff7b78"
/ApEinfo_revcolor = "#ff7b78"
/ApEinfo_graphicformat = "arrow_data {{0 1 2 0 0 -1} { } 0}
width 5 offset 0"

misc_feature 1 . . . 558
/label = CamR_*Pseudomonas putida* BAA03510
/ApEinfo_fwdcolor = "cyan"
/ApEinfo_revcolor = "cyan"
/ApEinfo_graphicformat = "arrow_data {{0 1 2 0 0 -1} { } 0}
width 5 offset 0"

misc_feature 709 . . . 711
/label = Stop codon
/ApEinfo_fwdcolor = "#ff0000"
/ApEinfo_revcolor = "#ff0000"
/ApEinfo_graphicformat = "arrow_data {{0 1 2 0 0 -1} { } 0}
width 5 offset 0"

ORIGIN
1 ATGGACATCA AGCAATCTTT GTTGCACGCT GCTATGAGAT TGTTGTCTGC TAAGGGTCGC

61 GACGGTGCTA CCATGCGACC AATCTGTGCT GAAGTTGGTG TTACCCCACC AACCTTGTAC

121 CACCACTACG GTGACTTGCA AGGTTTGCAC AAGGCTGCTA TCGACGAAAC CTACAGACAA

181 GTTGCTGAAG CTTACCACGG TGGTACCGAA GAAAGAGGTC CATTGAAGGG TATCCGCGAC

241 GGTTGGGCTA CCTTCTTGCA ATTCGCTTAC TCTGAACCAA ACATGTGTAG AATGTTGGTT

301 CAACACATCA TGGCTGGTGA ACCACCATCT ATGGTTGCTG ACACCTTGAG AGGTGTTGCT

361 GACGACTTGG CTCAATTCCA CGCTCAAGGT AGATTGACCT TCCCACCAAG AGAAGCTGCT

421 CAATTGTTGT GGATGGGTGC TTTGGGTGCT TTGACCTACG CTTTGTCTAG AGAAGGTGCT

481 GGTTACACCC AAGACTTGGC TTTGCAAAAG GCTAAGTTGG ACATCACCTT GGTTGCTTTG

541 TTCAACATCG AAGAAGAAgg gccggccGAC GCTTTGGACG ACTTCGACTT GGACATGTTG

-continued

| LOCUS SEQ_ID_NO_25_Tab 711 bp ds-DNA circular 04-DEC-2016 |  |
|---|---|
| 601 | CCTGCAGATG CACTTGATGA TTTTGATCTT GATATGCTTC CAGCAGACGC ATTGGATGAC |
| 661 | TTTGACCTTG ACATGCTTCC TGGTATGCCA AAGAAGAAGA GAAAGGTATG A<br>(SEQ ID NO: 25; Table 4 camTA (=camR-VP16-NLS) in pSIB859) |
| // |  |

| LOCUS SEQ_ID_NO_27_Tab 577 bp ds-DNA circular 04-DEC-2016 |  |
|---|---|
| DEFINITION . |  |
| ACCESSION |  |
| VERSION |  |
| SOURCE . |  |
| ORGANISM . |  |
| COMMENT |  |
| COMMENT |  |
| COMMENT | ApEinfo: methylated:1 |
| FEATURES | Location/Qualifiers |
| misc_feature | 204 . . . 207<br>/label = acceptor<br>/ApEinfo_fwdcolor = "cyan"<br>/ApEinfo_revcolor = "green"<br>/ApEinfo_graphicformat = "arrow_data {{0 1 2 -1} { } 0}<br>width 5 offset 0" |
| misc_feature | 431 . . . 434<br>/label = acceptor(1)<br>/ApEinfo_label = "acceptor"<br>/ApEinfo_fwdcolor = "#00ffff"<br>/ApEinfo_revcolor = "green"<br>/ApEinfo_graphicformat = "arrow_data {{0 1 2 -1} { } 0}<br>width 5 offset 0" |
| misc_feature | 396 . . . 427<br>/label = CamO core<br>/ApEinfo_fwdcolor = "#ff2f14"<br>/ApEinfo_revcolor = "green"<br>/ApEinfo_graphicformat = "arrow_data {{0 1 2 -1} { } 0}<br>width 5 offset 0" |
| misc_feature | 208 . . . 239<br>/label = CamO core(1)<br>/ApEinfo_label = "CamO core"<br>/ApEinfo_fwdcolor = "#ff2f14"<br>/ApEinfo_revcolor = "green"<br>/ApEinfo graphicformat = "arrow_data {{0 1 2 -1} { } 0}<br>width 5 offset 0" |
| misc_feature | 284 . . . 315<br>/label = CamO core(2)<br>/ApEinfo_label = "CamO core"<br>/ApEinfo_fwdcolor = "#ff2f14"<br>/ApEinfo_revcolor = "green"<br>/ApEinfo_graphicformat = "arrow_data {{0 1 2 -1} { } 0}<br>width 5 offset 0" |
| misc_feature | 1 . . . 203<br>/label = ADH1 transcriptional terminator<br>/ApEinfo_fwdcolor = "#ffec1f"<br>/ApEinfo_revcolor = "green"<br>/ApEinfo_graphicformat = "arrow_data {{0 1 2 -1} { } 0}<br>width 5 offset 0" |
| misc_feature | 432 . . . 574<br>/gene = "pCYC1"<br>/product = "CYC1 TATA region" |

-continued

```
LOCUS SEQ_ID_NO_27_Tab 577 bp ds-DNA circular 04-DEC-2016

                /label = CYC1 TATA region
                /ApEinfo_fwdcolor = "pink"
                /ApEinfo_revcolor = "pink"
                /ApEinfo_graphicformat = "arrow_data {{0 1 2 -1} { } 0}
                width 5 offset 0"

misc_feature    359 . . . 390
                /label = CamO core(3)
                /ApEinfo_label = "CamO core"
                /ApEinfo_fwdcolor = "#ff2f14"
                /ApEinfo_revcolor = "green"
                /ApEinfo_graphicformat = "arrow_data {{0 1 2 -1} { } 0}
                width 5 offset 0"

misc_feature    246 . . . 277
                /label = CamO core(4)
                /ApEinfo_label = "CamO core"
                /ApEinfo_fwdcolor = "#ff2f14"
                /ApEinfo_revcolor = "green"
                /ApEinfo_graphicformat = "arrow_data {{0 1 2 -1} { } 0}
                width 5 offset 0"

misc_feature    322 . . . 353
                /label = CamO core(5)
                /ApEinfo_label = "CamO core"
                /ApEinfo_fwdcolor = "#ff2f14"
                /ApEinfo_revcolor = "green"
                /ApEinfo_graphicformat = "arrow_data {{0 1 2 -1} { } 0}
                width 5 offset 0"

misc_feature    432 . . . 577
                /label = ScCYC1 promoter
                /ApEinfo_fwdcolor = "#1dff0f"
                /ApEinfo_revcolor = "green"
                /ApEinfo_graphicformat = "arrow_data {{0 1 2 -1} { } 0}
                width 5 offset 0"

misc_feature    208 . . . 430
                /label = camR operator
                /ApEinfo_fwdcolor = "#ff8040"
                /ApEinfo_revcolor = "#ff8040"
                /ApEinfo_graphicformat = "arrow_data {{0 1 2 -1} { } 0}
                width 5 offset 0"

ORIGIN
  1             cacttctaaa taagcgaatt tcttatgatt tatgattttt attattaaat aagttataaa

 61             aaaaataagt gtatacaaat tttaaagtga ctcttaggtt ttaaaacgaa aattcttgtt

121             cttgagtaac tctttcctgt aggtcaggtt gctttctcag gtatagcatg aggtcgctct

181             tattgaccac acctctaccg gcaaggtCAG GCTCTATATC TGCGATATAC TGAGCATATC

241             CCCCCCAGGC TCTATATCTG CGATATACTG AGCATATCCC CCCCAGGCTC TATATCTGCG

301             ATATACTGAG CATATCCCCC CCAGGCTCTA TATCTGCGAT ATACTGAGCA TATCCCCCCA

361             GGCTCTATAT CTGCGATATA CTGAGCATAT CCCCCCAGGC TCTATATCTG CGATATACTG

421             AGCATATCCC aatggcatgc atgtgctctg tatgtatata aaactcttgt tttcttcttt

481             tctctaaata ttctttcctt atacattagg tcctttgtag cataaattac tatacttcta

541             tagacacgca aacacaaata cacacactaa attaATA (SEQ ID NO: 27;
                Table 4 camPr (=ADH1tr-camR operator-CYC1pr) in pSIB859)
//
```

```
LOCUS SEQ_ID_NO_28_Tab 747 bp ds-DNA circular 04-DEC-2016

DEFINITION .

ACCESSION

VERSION
```

-continued

```
LOCUS SEQ_ID_NO_28_Tab 747 bp ds-DNA circular 04-DEC-2016

SOURCE .

ORGANISM .

COMMENT

COMMENT

COMMENT        ApEinfo: methylated:1

FEATURES       Location/Qualifiers

misc_feature   1 . . . 618
               /label = mutated TetR
               /ApEinfo_fwdcolor = "cyan"
               /ApEinfo_revcolor = "green"
               /ApEinfo_graphicformat = "arrow_data {{0 1 2 0 0 -1} { } 0}
               width 5 offset 0"

misc_feature   619 . . . 744
               /label = VP16
               /ApEinfo_fwdcolor = "#ff1fdd"
               /ApEinfo_revcolor = "green"
               /ApEinfo_graphicformat = "arrow_data {{0 1 2 0 0 -1} { } 0}
               width 5 offset 0"

misc_feature   745 . . . 747
               /label = Stop codon
               /ApEinfo_fwdcolor = "#ff8080"
               /ApEinfo_revcolor = "#ff8080"
               /ApEinfo_graphicformat = "arrow_data {{0 1 2 0 0 -1} { } 0}
               width 5 offset 0"

ORIGIN
  1            ATGAGTAGAT TGGACAAGTC TAAGGTTATC AACGGTGCTT TGGAATTGTT GAACGGTGTT

 61            GGTATCGAAG GTTTGACCAC CAGAAAGTTG GCTCAAAAGT TGGGTGTTGA ACAACCAACC

121            TTGTACTGGC ACGTTAAGAA CAAGAGAGCT TTGTTGGACG CTTTGCCAAT CGAAATGTTG

181            GACAGACACC ACACCCACTT CTGTCCATTG GAAGGTGAAT CTTGGCAAGA CTTCTTGAGA

241            AACAACGCTA AGTCTTTCAG ATGTGCTTTG CTCTCTCACC GCGACGGTGC TAAGGTTCAC

301            TTGGGAACCA GACCAACCGA AAAGCAATAC GAAACCTTGG AAAACCAATT GGCTTTCTTG

361            TGTCAACAAG GTTTCTCTTT GGAAAACGCT TTGTACGCTT TGTCTGCTGT TGGTCACTTC

421            ACCTTGGGTT GTGTTTTGGA AGAACAAGAA CACCAAGTTG CTAAGGAAGA AAGAGAAACC

481            CCAACCACCG ACTCTATGCC ACCATTGCTC AGACAAGCTA TCGAATTGTT CGACAGACAA

541            GGTGCTGAAC CAGCTTTCTT GTTCGGTTTG GAATTGATCA TCTGTGGTTT GGAAAAGCAA

601            TTGAAGTGTG AATCTGGTGG GCCGGCCGAC GCTTTGGACG ACTTCGACTT GGACATGTTG

661            CCAGCTGACG CTTTGGACGA CTTCGACTTG GACATGTTGC CAGCTGACGC TTTGGACGAC

721            TTCGACTTGG ACATGTTGCC AGGTTGA (SEQ ID NO: 28; Table 4 rtTA
               (=mutated tetR-VP16) in pSIB499)
//
```

```
LOCUS SIB027 partial 881 bp ds-DNA linear 30-SEP-2013

DEFINITION .

ACCESSION

VERSION

SOURCE .

ORGANISM .
```

-continued

```
LOCUS SIB027 partial 881 bp ds-DNA linear 30-SEP-2013

COMMENT

COMMENT        ApEinfo: methylated:1

FEATURES       Location/Qualifiers

misc_feature   12 . . . 871
               /label = ScTDHpr
               /ApEinfo_fwdcolor = #baff87
               /ApEinfo_revcolor = #baff87
               /ApEinfo_graphicformat = arrow_data {{0 1 2 0 0 -1} { } 0}
               width 5 offset 0

misc_feature   8 . . . 11
               /label = Adapter(CAGT)
               /ApEinfo_fwdcolor = #ff1916
               /ApEinfo_revcolor = #ff1916
               /ApEinfo_graphicformat = arrow_data {{0 1 2 0 0 -1} { } 0}
               width 5 offset 0

misc_feature   871 . . . 874
               /label = Adapter(AATG)
               /ApEinfo_fwdcolor = €ff1638
               /ApEinfo_revcolor = €ff1638
               /ApEinfo_graphicformat = arrow_data {{0 1 2 0 0 -1} { } 0}
               width 5 offset 0

ORIGIN
  1            GGTCTCacag tCTCGATGGA TTAGTTTCTC ACAGGTAACA TAACAAAAAC CAAGAAAAGC

 61            CCGCTTCTGA AAACTACAGT TGACTTGTAT GCTAAAGGGC CAGACTAATG GGAGGAGAAA

121            AAGAAACGAA TGTATATGCT CATTTACACT CTATATCACC ATATGGAGGA TAAGTTGGGC

181            TGAGCTTCTG ATCCAATTTA TTCTATCCAT TAGTTGCTGA TATGTCCCAC CAGCCAACAC

241            TTGATAGTAT CTACTCGCCA TTCACTTCCA GCAGCGCCAG TAGGGTTGTT GAGCTTAGTA

301            AAAATGTGCG CACCACAAGC CTACATGACT CCACGTCACA TGAAACCACA CCGTGGGGCC

361            TTGTTGCGCT AGGAATAGGA TATGCGACGA AGACGCTTCT GCTTAGTAAC CACACCACAT

421            TTTCAGGGGG TCGATCTGCT TGCTTCCTTT ACTGTCACGA GCGGCCCATA ATCGCGCTTT

481            TTTTTTAAAA GGCGCGAGAC AGCAAACAGG AAGCTCGGGT TTCAACCTTC GGAGTGGTCG

541            CAGATCTGGA GACTGGATCT TTACAATACA GTAAGGCAAG CCACCATCTG CTTCTTAGGT

601            GCATGCGACG GTATCCACGT GCAGAACAAC ATAGTCTGAA GAAGGGGGGG AGGAGCATGT

661            TCATTCTCTG TAGCAGTAAG AGCTTGGTGA TAATGACCAA AACTGGAGTC TCGAAATCAT

721            ATAAATAGAC AATATATTTT CACACAATGA GATTTGTAGT ACAGTTCTAT TCTCTCTCTT

781            GCATAAATAA GAAATTCATC AAGAACTTGG TTTGATATTT CACCAACACA CACAAAAAAC

841            AGTACTTCAC TAAATTTACA CACAAAACAA AatgaGAGAC C (SEQ ID NO: 30;
               Table 4 yGG-TDH 1pr in pSIB027)
//
```

```
LOCUS SEQ_ID_NO_31_Tab 792 bp ds-DNA linear 04-DEC-2016

DEFINITION .

ACCESSION

VERSION

SOURCE .

ORGANISM .

COMMENT
```

-continued

```
LOCUS SEQ_ID_NO_31_Tab 792 bp ds-DNA linear 04-DEC-2016

COMMENT         ApEinfo: methylated:1

FEATURES        Location/Qualifiers

misc_feature    12 . . . 781
                /gene = "CMV-P"
                /product = "CMV promotor"
                /label = CMV promoter
                /ApEinfo_fwdcolor = "#fffea3"
                /ApEinfo_revcolor = "#fffea3"
                /ApEinfo_graphicformat = "arrow_data {{0 1 2 0 0 -1} { } 0}
                width 5 offset 0"

misc_feature    704 . . . 704
                /label = G->T (to disrupt BsmBI)
                /ApEinfo_fwdcolor = "cyan"
                /ApEinfo_revcolor = "cyan"
                /ApEinfo_graphicformat "arrow_data {{0 1 2 0 0 -1} { } 0}
                width 5 offset 0"

misc_feature    8 . . . 11
                /label = Acceptor (CAGT)
                /ApEinfo_fwdcolor = "cyan"
                /ApEinfo_revcolor = "cyan"
                /ApEinfo_graphicformat "arrow_data {{0 1 2 0 0 -1} { } 0}
                width 5 offset 0"

misc_feature    782 . . . 785
                /label = Acceptor (AATG)
                /ApEinfo_fwdcolor = "cyan"
                /ApEinfo_revcolor = "cyan"
                /ApEinfo_graphicformat "arrow_data {{0 1 2 0 0 -1} { } 0}
                width 5 offset 0"

ORIGIN
  1             GGTCTCacag tgagcttggc ccattgcata cgttgtatcc atatcataat atgtacattt

 61             atattggctc atgtccaaca ttaccgccat gttgacattg attattgact agttattaat

121             agtaatcaat tacggggtca ttagttcata gcccatatat ggagttccgc gttacataac

181             ttacggtaaa tggcccgcct ggctgaccgc ccaacgaccc ccgcccattg acgtcaataa

241             tgacgtatgt tcccatagta acgccaatag ggactttcca ttgacgtcaa tgggtggagt

301             atttacggta aactgcccac ttggcagtac atcaagtgta tcatatgcca agtacgcccc

361             ctattgacgt caatgacggt aaatggcccg cctggcatta tgcccagtac atgaccttat

421             gggactttcc tacttggcag tacatctacg tattagtcat cgctattacc atggtgatgc

481             ggttttggca gtacatcaat gggcgtggat agcggtttga ctcacgggga tttccaagtc

541             tccaccccat tgacgtcaat gggagtttgt tttggcacca aaatcaacgg gactttccaa

601             aatgtcgtaa caactccgcc ccattgacgc aaatgggcgg taggcgtgta cggtgggagg

661             tctatataag cagagctcgt ttagtgaacc gtcagatcgc ctgTagacgc catccacgct

721             gttttgacct ccatagaaga caccgggacc gatccagcct ccgcggcccg aattaattca

781             tAatgaGAGA CC (SEQ ID NO: 31; Table 4 yGG-mutated CMVpr in
                pSIB237)
//
```

```
LOCUS SEQ_ID_NO_32_Tab 725 bp ds-DNA linear 04-DEC-2016

DEFINITION .

ACCESSION

VERSION
```

-continued

```
LOCUS SEQ_ID_NO_32_Tab 725 bp ds-DNA linear 04-DEC-2016

SOURCE .

ORGANISM .

COMMENT

COMMENT         ApEinfo: methylated:1

FEATURES        Location/Qualifiers

misc_feature    12 . . . 718
                /label = ScGSH1tr
                /ApEinfo_fwdcolor = "#96ff9b"
                /ApEinfo_revcolor = "green"
                /ApEinfo_graphicformat = "arrow_data {{0 1 2 0 0 -1} { } 0}
                width 5 offset 0"

misc_feature    715 . . . 718
                /label = adapter
                /ApEinfo_fwdcolor = "#ff304b"
                /ApEinfo_revcolor = "#ff304b"
                /ApEinfo_graphicformat = "arrow_data {{0 1 2 0 0 -1} { } 0}
                width 5 offset 0/

misc_feature    8 . . . 11
                /label = adapter(1)
                /ApEinfo_label = "adapter"
                /ApEinfo_fwdcolor = "#ff0000"
                /ApEinfo_revcolor = "#ff0000"
                /ApEinfo_graphicformat = "arrow_data {{0 1 2 0 0 -1} { } 0}
                width 5 offset 0"

ORIGIN
  1             GGTCTCgtga gACTCCTTTT ACTTCGGTTG TGAAAGAAAG TTGACATTAT CGATTTGGGT

 61             GACACGGTGA TTGAAAAAGC AACGACCAGT ATTATACCTC TTTTTTTTAT TATTCAGTTT

121             ATATTTTTGC AAGTGATCTT AAGCATTTCT ACACAAACTT ATGCCAACGT GACCATTTAT

181             TATTTTATAT AGCAAAAAAA AATGAGGGGC CTTGCAGAAC AATTGTTGCG AGTTTCTAAT

241             AACAAGCACG TAGAATATTG GCCATTTAAT TTTTCTCTTC AATTTATAGA ATGGTTGTGT

301             TAGTGACAAA AAGAATATTC TTCCCCGCCA GGACTCGAAC CTGGAATCTC CTGGTTCGTA

361             GCCAGACGCC GTGACCATTG GGCCACGAGG AACAAGAATA TAAAGATCTC TGAGGGCAAG

421             GTATGCCTAT GTCGCAATAA AATGTTTGTT CCTGCGCAAA AGTAAAGTTC TATTAATATA

481             CAACTACACA GTTATCGGTT CACACTATTC GATAGTTGTA AAAACCATTT TGATAAAGAT

541             ATAACAAGGC GTTTATTAAG GACATTTTTG CTACAAGTCG TGAAGTATTG ATTGTAGGCG

601             ATCGTTGGTA ACTTTCTCCA TATCGGAATA TTCAATATTG AACTCACCCC TCCCTTGCGA

661             TAAGCTCCTT AGCTTATTGG TGTAGGTGGT AATTTCCCTT AGTGGCACTT TCGCTTTTcG

721             AGACC (SEQ ID NO: 32; Table 4 yGG-ScGSH 1tr in pSIB031)
//
```

```
LOCUS SEQ_ID_NO_33_Tab 748 bp ds-DNA linear 04-DEC-2016

DEFINITION .

ACCESSION

VERSION

SOURCE .

ORGANISM .

COMMENT
```

-continued

LOCUS SEQ_ID_NO_33_Tab 748 bp ds-DNA linear 04-DEC-2016

COMMENT

COMMENT ApEinfo: methylated:1

FEATURES Location/Qualifiers misc_feature 8 . . . 11
/label = Adapter
/ApEinfo_fwdcolor = "#ff0000"
/ApEinfo_revcolor = "#ff0000"
/ApEinfo_graphicformat = "arrow_data {{0 1 2 0 0 -1} { } 0}
width 5 offset 0"

misc_feature 738 . . . 741
/label = adapter
/ApEinfo_fwdcolor = "#ff0000"
/ApEinfo_revcolor = "#ff0000"
/ApEinfo_graphicformat = "arrow_data {{0 1 2 0 0 -1} { } 0}
width 5 offset 0"

misc_feature 12 . . . 741
/label = mutated ScSTR1tr (BsmBI-free)
/ApEinfo_fwdcolor = "#afffdd"
/ApEinfo_revcolor = "#afffdd"
/ApEinfo_graphicformat = "arrow_data {{0 1 2 0 0 -1} { } 0}
width 5 offset 0"

ORIGIN
1 GGTCTCgtga gTCGCCAGTG CCAtGTtTCT GCCTTCGACC GGACCTTTTT AAGTACGATA

61 AATATCCTTT TATAAATATA TAGTCTAAAA TATCCATTAA TACTGTGCTC AATCAATCGT

121 GTTAGATGAT TTAGTTTTTT CCAAATCGTT ATTATAGTGC AGAAGTAGTA TACATAAAGG

181 CATATGCATG CGATTTGGAA GTAACGCTCG CCGTAGACAA GTAAGAATGC CTGCTGTCTT

241 GAGAACCAGG TCCAAAGAAT CCTCTATAGA GCAGAAGCCT GCTTCCAGAA CTAGAACGAG

301 ATCAAGAAGG GGCAAGCGTG GTCGTGACGA TGATGATGAT GACGACGATG AGGAAAGCGA

361 TGATGCATAC GATGAAGTAG GTAATGACTA TGACGAGTAT GCTTCAAGAG CGAAGCTGGC

421 CACCAATAGG CCCTTCGAAA TAGTCGCGGG ACTGCCTGCT AGTGTGGAGC TGCCCAACTA

481 TAACTCTTCG CTTACTCATC CGCAATCAAT TAAAAATTCT GGGGTGCTTT ACGACTCTCT

541 GGTCAGTTCC AGAAGAACCT GGGTTCAGGG TGAGATGTTT GAACTGTATT GGCGAAGACC

601 TAAGAAAATT GTTAGTGAAT CTACCCCAGC AGCGACGGAG AGTCCAACAT CTGGAACGAT

661 TCCTTTGATT CGAGATAAGA TGCAGAAAAT GTGCGATTGT GTAATGAGTG GAGGTCCTCA

721 CACGTTCAAA GTTAGACTTT TgGAGACC (SEQ ID NO: 33; Table 4
yGG-mutated STR1tr in pSIB206)
//

LOCUS SEQ_ID_NO_34_Tab 573 bp ds-DNA linear 04-DEC-2016

DEFINITION .

ACCESSION

VERSION

SOURCE .

ORGANISM .

COMMENT

COMMENT

COMMENT ApEinfo: methylated:1

-continued

```
LOCUS SEQ_ID_NO_34_Tab 573 bp ds-DNA linear 04-DEC-2016

FEATURES        Location/Qualifiers

misc_feature    1 . . . 6
                /label = BsaI
                /ApEinfo_fwdcolor = "cyan"
                /ApEinfo_revcolor = "cyan"
                /ApEinfo_graphicformat = "arrow_data {{0 1 2 0 0 -1} { } 0}
                width 5 offset 0"

misc_feature    568 . . . 573
                /label = BsaI(1)
                /ApEinfo_label = "BsaI"
                /ApEinfo_fwdcolor = "cyan"
                /ApEinfo_revcolor = "cyan"
                /ApEinfo_graphicformat = "arrow_data {{0 1 2 0 0 -1} { } 0}
                width 5 offset 0"

misc_feature    8 . . . 11
                /label = Adapter
                /ApEinfo_fwdcolor = "#ff0000"
                /ApEinfo_revcolor = "#ff0000"
                /ApEinfo_graphicformat = "arrow_data {{0 1 2 0 0 -1} { } 0}
                width 5 offset 0"

misc_feature    563 . . . 566
                /label = Adapter(1)
                /ApEinfo_label = "Adapter"
                /ApEinfo_fwdcolor = "#ff0000"
                /ApEinfo_revcolor = "#ff0000"
                /ApEinfo_graphicformat = "arrow_data {{0 1 2 0 0 -1} { } 0}
                width 5 offset 0"

misc_feature    12 . . . 562
                /label = SOL3tr
                /ApEinfo_fwdcolor = "#84ff89"
                /ApEinfo_revcolor = "#84ff89"
                /ApEinfo_graphicformat = "arrow_data {{0 1 2 0 0 -1} { } 0}
                width 5 offset 0"

ORIGIN
  1             GGTCTCaTGA GAAAAGACAC ACATGCGAGC TTTCGAACCT CAGATGCTAA TATTACGTGT

 61             TATATATACC AAACTTTATA AAATGACATA GATATTTTAT GCTGTGATAG CTTTCCTGTT

121             ATGGAGAAGC TCTTCTTATT CCCCCTGTCA ACTTTCATAC TCTTGTAGAA TTTCCTTTAT

181             GATAGGTTTA TCGCTTACGA ATTTAGACTT TGATGTGATG GGTTTGGCAC CTGTTCTTTT

241             TCCACAACCT TTGCGTGCCT CATCAATAGC GTTTGATCTG TCGGGAAATT TGTATTTGTA

301             GAGTGCATCC TTGCACATTG TATAGACCCA ATTACGCTCT TCTAACAGGT TCACGAACGA

361             TTTTATTTCA GGAACAGAGC CGATTGTACT TTTTGAACCT ATAATGATCA GCTTGGATTT

421             GGCCCTTGTC ATGGCAACAT TGACTCTTCT TAGCTCTTTC AGCAGCGCTC CTCCATTTAA

481             TTGAGAATTT CTTCTAACCA TGGAAATAAT AATGCACTTT TTGTCACGAC CTTGAAACTG

541             ATCAGCAGTC AAGATCTCTA GCTTTTaGAG ACC (SEQ ID NO: 34; Table 4
                yGG-SOL3tr in pSIB639)
//
```

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system comprising:

an orthologous repressible yeast gene expression construct comprising:

(i) a regulator binding sequence and a target gene sequence, wherein the regulator binding sequence comprises a phlO nucleic acid sequence; and (ii) a transcription transcriptional activator expression construct comprising SEQ ID NO: 11.

2. The system of claim 1, wherein binding of the regulator binding sequence to the transcriptional activator in the absence of DAPG results in expression of the target gene sequence downstream from the regulator binding sequence.

3. The system of claim 2, wherein the repressible gene expression construct further comprises a transcription terminator sequence.

4. The system of claim 3, wherein the transcriptional terminator sequence is located upstream of the regulator binding sequence.

5. The system of claim 3, wherein the transcriptional terminator sequence comprises a nucleic acid sequence encoding alcohol dehydrogenase 1 (ADH1).

6. The system of claim 2, wherein the regulator binding sequence comprises at least one copy of a nucleic acid sequence of phlO, wherein the sequence of phlO comprises SEQ ID NO: 3.

7. The system of claim 1, wherein the regulator binding sequence comprises at least one copy of a nucleic acid sequence of phlO, wherein the sequence of phlO comprises SEQ ID NO: 3.

8. The system of claim 1, wherein the repressible gene expression construct further comprises a promoter downstream from the regulator binding sequence.

9. The system of claim 8, wherein the promoter downstream from the regulator binding sequence lacks an upstream activating sequence.

10. The system of claim 9, wherein the promoter downstream from the regulator binding sequence comprises a cytochrome c isoform 1 (CYC1) promoter.

11. The system of claim 1, wherein the transcription activator expression construct further comprises a sequence encoding at least one VP16 tandem repeat.

12. The system of claim 1, wherein the transcription activator expression construct further comprises a promoter sequence comprising the human cytomegalovirus promoter (CMV).

13. A transcription enhancer expression construct comprising a nucleic acid sequence encoding a PhIF transcription regulator domain operatively linked to a nuclear localization signal (NLS) domain, wherein the transcription enhancer expression construct comprises SEQ ID NO: 11.

14. An isolated recombinantly engineered cell comprising:

an orthologous repressible yeast gene expression construct comprising a regulator binding sequence and a target gene sequence, wherein the regulator binding sequence comprises a phlO nucleic acid sequence; and a transcriptional activator expression construct comprising SEQ ID NO: 11.

* * * * *